(12) United States Patent
Hirano et al.

(10) Patent No.: US 11,396,536 B2
(45) Date of Patent: Jul. 26, 2022

(54) PEPTIDE-HLA COMPLEXES AND METHODS OF PRODUCING SAME

(71) Applicant: UNIVERSITY HEALTH NETWORK, Toronto (CA)

(72) Inventors: Naoto Hirano, Toronto (CA); Munehide Nakatsugawa, Sapporo (JP); Muhammed Aashiq Rahman, Brisbane (AU); Kenji Murata, Toronto (CA)

(73) Assignee: University Health Network, Toronto (CA)

( * ) Notice: Subject to any disclaimer, the term of this patent is extended or adjusted under 35 U.S.C. 154(b) by 557 days.

(21) Appl. No.: 16/095,913

(22) PCT Filed: Apr. 27, 2017

(86) PCT No.: PCT/CA2017/000102
§ 371 (c)(1),
(2) Date: Oct. 23, 2018

(87) PCT Pub. No.: WO2017/185169
PCT Pub. Date: Nov. 2, 2017

(65) Prior Publication Data
US 2019/0345222 A1    Nov. 14, 2019

Related U.S. Application Data

(60) Provisional application No. 62/328,325, filed on Apr. 27, 2016.

(51) Int. Cl.
| | |
|---|---|
| *A61K 38/17* | (2006.01) |
| *C07K 14/00* | (2006.01) |
| *A61K 38/00* | (2006.01) |
| *A61K 39/00* | (2006.01) |
| *C07K 19/00* | (2006.01) |
| *C07K 14/74* | (2006.01) |
| *C07K 7/06* | (2006.01) |

(52) U.S. Cl.
CPC .......... *C07K 14/70539* (2013.01); *C07K 7/06* (2013.01); *C07K 2319/02* (2013.01); *C07K 2319/21* (2013.01)

(58) Field of Classification Search
CPC .......... A61P 35/00; A61P 37/06; A61P 37/04; A61K 38/1774; Y02A 50/30
See application file for complete search history.

(56) References Cited

U.S. PATENT DOCUMENTS

| | | |
|---|---|---|
| 2003/0124613 A1 | 7/2003 | Hildebrand et al. |
| 2010/0168390 A1 | 7/2010 | Brix et al. |

FOREIGN PATENT DOCUMENTS

| | | |
|---|---|---|
| WO | WO-2017185169 A1 | 11/2017 |

OTHER PUBLICATIONS

Rodenko et al., "Generation ofpeptide-MHC class I complexes through UV-mediated ligand exchange". Nature Protocols, 2006, vol. 1(3), pp. 1120-1132.*
Barker et al., "Conditional MHC class I ligands and peptide exchange technology for the human MHC gene porducts HLA-A1, -A3, -AII and-B7". Proc Natl Acad Sci, 2008, vol. 105(10), pp. 3825-3830.*
Saini et al., "Dipeptides catalyze rapid peptide exchange on MHC class I molecules". Proc Natl Acad Sci, 2015, vol. 112(1), pp. 202-207.*
Rodenko et al.,"Generation of peptide-MHC class complexes through UV-mediated ligand exchange".Nature Protocols,2006,vol. 1(3),pp. 1120-1132.*
Bakker et al.,"Conditional MHC classligands and peptide exchange technology for the human MHC gene products HLA-A1,-A3,-AIIand-B7".Proc Natl Acad Sci,2008,vol. 105(10),pp. 3825-3830.*
Saini et al., "Dipeptides catalyze rapid peptide exchange o nMHC class molecules".ProcNatlAcadSci,2015,vol. 112(1),pp. 202-207.*
Kawana-Tachikawa et al., "An efficient and versatile mammalian viral vector system for major histocimpatibility complex class 1/peptide complexes", Journal of Virology, 2002, 76(23): 11982-11988.*
Altman et al., "Phenotypic analysis of antigen-specific T lymphocytes" *Science*, 1996, 274(5284):94-96.
Bakker et al., "Conditional MHC class I ligands and peptide exchange technology for the human MHC gene products HLA-A1, -A3, -A11 and -B7" *Proc Natl Acad Sci*, 2008, 105(10):3825-3830.
Butler et al., "A panel of human cell-based artificial APC enables the expansion of long-lived antigen-specific CD4+ T cells restricted by prevalent HLA-DR allels" *Int Immunol*, 2010, 22(11):863-873.
Butler et al., "Long-lived antitumor CD8+ lymphocytes for adoptive therapy generated using an artificial antigen-presenting cell" *Clin Cancer Res.*, 2007, 13(6):1857-1867.
Chen et al., "Fusion protein linkers: Property, design and functionality" *Adv Drug Deliv Rev.*, 2013, 65(10):1357-1369.
Dolton et al., "More tricks with tetramers: a practical guide to staining T cells with peptide-MHC multimers" *Immunology*, 2015, 146(1):11-22.
Feldman et al., "Adoptive Cell Therapy—Tumor-infiltrating Lymphocytes, T-Cell Receptors, and Chimeric Antigen Receptors," *Semin Oncol*, 2015, 42(4):626-639.
Hirano et al., "Autoantibodies frequently detected in patients with aplastic anemia" *Blood*, 2003, 102(13):4567-4575.

(Continued)

*Primary Examiner* — Barry A Chestnut
(74) *Attorney, Agent, or Firm* — Sterne, Kessler, Goldstein & Fox P.L.L.C.

(57) ABSTRACT

There is provided herein, the use of mammalian derived HLA class I molecule for in vitro peptide exchange. For example, there is provided a method of producing an HLA class I molecule complexed to a pre-selected peptide comprising: (a) providing a mammalian derived HLA class I molecule complexed to an existing peptide; (b) incubating, in vitro, the HLA class I molecule complexed to the existing peptide with the pre-selected peptide, wherein the pre-selected peptide is at a concentration sufficient to replace the existing peptide to produce the HLA class I molecule complexed to the pre-selected peptide; and the HLA class I molecule comprises α1, α2, α3 and β2m domains.

19 Claims, 29 Drawing Sheets

Specification includes a Sequence Listing.

(56) References Cited

OTHER PUBLICATIONS

Hirano et al., "Efficient presentation of naturally processed HLA class I peptides by artificial antigen-presenting cells for the generation of effective antitumor responses" *Clin Cancer Res*, 2006, 12(10:2967-2975.

Hirano et al., "Engagement of CD83 ligand induces prolonged expansion of CD8+ T cells and preferential enrichment for antigen specificity" *Blood*, 2006, 107(4):1528-1536.

Hirano et al., "Identification of an immunogenic CD8+ T-cell epitope derived from gamma-globin, a putative tumor-associated antigen for juvenile myelomonocytic leukemia" *Blood*, 2006, 108(8):2662-2668.

Imataki et al., "IL-21 can supplement suboptical Lck-independent MAPK activation in a STAT-3-dependent manner in human CD8(+) T cells" *J Immunol*, 2012, 188(4)1609-1619.

International Search Report and Written Opinion issued in International Patent Application No. PCT/CA2017/000102, dated Jul. 13, 2017.

Janeway, "Immunobiology: the immune system in health and disease," New York: Garland Science, 2005; 41 pages.

Kagoya et al., "BET bromodomain inhibition enhances T cell persistence and function in adoptive immunotherapy models" *J. Clin. Invest.*, 2016, 126(9):3479-3494.

Kawana-Tachikawa et al., "An efficient and Versatile Mammalian Viral Vector System for Major Histocompatibility Complex Class I/Peptide Complexes" *Journal of Virology*, 2002, 76(23):11982-11988.

Kawase et al., "Alternative splicing due to an intronic SNP in HMSD generates a novel minor histocompatibility antigen" *Blood*, 2007, 110(3):1055-1063.

Klenerman et al., "Tracking T cells with tetramers: new tales from new tools" *Nat Rev Immunol*, 2002, 2(4):263-272.

Laugel et al., "Different T cell receptor affinity thresholds and CD8 coreceptor dependence govern cytotoxic T lymphocyte activation and tetramer binding properties" *J Biol. Chem.*, 2007, 282(33):23799-23810.

Marrack et al., "Evolutionarily conserved amino acids that control TCR-MHC interaction" *Annu Rev Immunol*, 2008, 26:171-203.

Migueles et al., "HLA B*5701 is highly associated with restriction of virus replication in a subgroup of HIV-infected long term nonprogressors" *Proc Natl Acad Sci U.S.A.*, 2000, 97(6):2709-2714.

Nakatsugawa et al., "Specific roles of each TCR hemichain in generating functional chain-centric TCR" *J. Immunol*, 2015, 194(7):3487-3500.

Nguyen et al., "Expansion and characterization of human melanoma tumor-infiltrating lymphocytes (TILs)" *PLoS One*, 2010, 5(11):e13940.

Ochi et al., "Optimization of T-cell reactivity by Exploiting TCR Chain Centricity for the Purpose of Safe and Effective Antitumor TCR Gene Therapy" *Cancer Immunol Res.*, 2015, 3(9):1070-1081.

Parker et al., "Scheme for ranking potential HLA-A2 binding peptides based on independent binding of individual peptide side-chains" *J. Immunol*, 1994, 152(1):163-175.

Robbins et al., "Mining exomic sequencing data to identify mutated antigens recognized by adoptively transferred tumor-reactive T cells" *Nat Med*, 2013, 19(6):747-752.

Rodenko et al., "Generation of peptide-MHC class I complexes through UV-mediated ligand exchange" *Nature Protocols*, 2006, 1(3):1120-1132.

Rossjohn et al., "T cell antigen receptor recognition of antigen-presenting molecules" *Annu Rev Immunol*, 2015, 33:169-200.

Saini et al., "Dipeptides catalyze rapid peptide exchange in MHC class I molecules" *Proc Natl Acad Sci U.S.A.*, 2015, 112(1):202-207.

Tanaka et al., "Induction of HLA-DP4-restricted anti-survivin Th1 and Th2 responses using an artificial antigen-presenting cell" *Clin Cancer Res*, 2011, 17(16):5392-5401.

Truscott et al., "Human Major Histocompatibility Complex (MHC) Class I Molecules with Disulfide Traps Secure Disease-related Antigenic Peptides and Exclude Competitor Peptides" *Journal of Biological Chemistry*, 2008, 283(12):7480-7490.

Uniprot, "UniProtKB—Q16655 (Mar1_Human)" Nov. 1, 1997, URL <https://www.uniprot.org/uniprot/Q16655 >.

Wooldridge et al., "Enhanced immunogenicity of CT1 antigens through mutation of the CD8 binding MHC class I invariant region," *Eur J Immunol*, 2007, 37(5):1323-1333.

Wooldridge et al., "MHC class I molecules with Superenhanced CD8 binding properties bypass the requirement for cognate TCR recognition and nonspecifically activiate CTLs" *J immunol*, 2010, 184(7):3357-3366.

Wooldridge et al., "Tricks with tetramers: how to get the most from multimeric peptide-MHC" *Immunology*, 2009, 126(2):147-164.

Allard, M., et al., "Soluble HLA-I/Peptide Monomers Mediate Antigen-Specific CD8 T Cell Activation through Passive Peptide Exchange with Cell-Bound HLA-I Molecules," *The Journal of Immunology* 192(11):5090-5097, The American Association of Immunologists, Inc., United States (Jun. 2014).

NIH Tetramer Core Facility, "Production Protocols—Class I MHC Tetramer Preparation: Overview," accessed at URL:[https://tetramer.yerkes.emory.edu/support/protocols] on May 21, 2021, 22 pages.

Stevens, J., et al., "Efficient Generation of Major Histocompatibility Complex Class I-Peptide Complexes Using Synthetic Peptide Libraries," *Journal of Biological Chemistry* 273(5):2874-2884, Elsevier Inc. on behalf of American Society for Biochemistry and Molecular Biology, Netherlands (Jan. 1998).

Vitiello, A., et al., "Analysis of the HLA-restricted influenza-specific cytotoxic T lymphocyte response in transgenic mice carrying a chimeric human-mouse class I major histocompatibility complex.," *Journal of Experimental Medicine* 173(4):1007-1015, Rockefeller University Press, United States (Apr. 1991).

\* cited by examiner

| No. | Specimen Code. | HLA-A | HLA-B | HLA-C |
|---|---|---|---|---|
| 1 | M25 | 01:01/02:01 | 07:02/08:01 | 07:01/07:02 |
| 2 | M29 | 02:01/11:01 | 07:02/27:02 | 02:02/07:02 |
| 3 | M31 | 02:01/24:02 | 40:01/44:02 | 03:04/05:01 |
| 4 | M37 | 02:01/24:02 | 14:02/48:01 | 08:02/08:03 |
| 5 | M38 | 02:01/- | 15:01/44:02 | 03:03/05:01 |
| 6 | M40 | 02:01/30:02 | 18:01/45:01 | 05:01/06:02 |
| 7 | M66 | 02:01/32:01 | 07:02/27:05 | 02:02/07:02 |
| 8 | M69 | 02:01/03:01 | 08:01/14:02 | 07:01/08:02 |
| 9 | M96 | 01:01/02:01 | 08:01/51:01 | 07:01/15:02 |

Figure 15

| No. | Specimen Code | HLA-A | HLA-B | HLA-C | Positive A2 dimer Staining (>0.3%) | ELISPOT |
|---|---|---|---|---|---|---|
| 1 | M25 | 01:01/02:01 | 07:02/08:01 | 07:01/07:02 | Wild type MART-1<br>Heteroclitic MART-1 | +<br>+ |
| 2 | M29 | 02:01/11:01 | 07:02/27:02 | 02:02/07:02 | None | NT |
| 3 | M31 | 02:01/24:02 | 40:01/44:02 | 03:04/05:01 | Wild type NY-ESO-1<br>Heteroclitic NY-ESO-1 | +<br>+ |
| 4 | M37 | 02:01/24:02 | 14:02/48:01 | 08:02/08:03 | SSX-2 (41-) | + |
| 5 | M38 | 02:01/- | 15:01/44:02 | 03:03/05:01 | None | NT |
| 6 | M40 | 02:01/30:02 | 18:01/45:01 | 05:01/06:02 | SSX-2 (41-) | + |
| 7 | M66 | 02:01/32:01 | 07:02/27:05 | 02:02/07:02 | gp-100 (154-)<br>gp-100 (209-)<br>gp-100 (280-)<br>Wild type MART-1<br>Heteroclitic MART-1 | +<br>+<br>+<br>+<br>+ |
| 8 | M69 | 02:01/03:01 | 08:01/14:02 | 07:01/08:02 | None | NT |
| 9 | M96 | 01:01/02:01 | 08:01/51:01 | 07:01/15:02 | Wild type MART-1<br>Heteroclitic MART-1 | +<br>+ |

Figure 28

SEQUENCE LISTING

```
<160> NUMBER OF SEQ ID NOS: 122

<210> SEQ ID NO 1
<211> LENGTH: 906
<212> TYPE: DNA
<213> ORGANISM: Homo sapiens

<400> SEQUENCE: 1
atgatgcggc ccatcgtgct ggtgctgctg tttgccacat ctgccctggc cggaagccac    60
```

```
agcatgcggt actttttcac cagcgtgtcc agacccggca gaggcgagcc cagattcatt      120
gccgtgggct acgtggacga cacccagttc gtcagattcg acagcgacgc cgccagccag      180
cggatggaac ctagagcccc ttggatcgag caggaaggcc ccgagtactg ggacggcgag      240
acacggaaag tgaaggccca cagccagacc cacagagtgg atctgggcac cctgcggggc      300
tactacaatc agtctgaggc cggctcccac accgtgcaga ggatgtacgg ctgtgacgtg      360
ggcagcgact ggcggttcct gagaggctac caccagtacg cctacgacgg caaggactat      420
atcgccctga agaggacct gcggagctgg acagccgccg atatggccgc ccagaccacc      480
aagcacaaat gggaagccgc ccacgtggcc gagcagctga gagcttatct ggaaggcacc      540
tgtgtggaat ggctgcggag atacctggaa aacggcaaag agacactgca gcgcacggac      600
gcccccaaaa cgcatatgac tcaccacgct gtctctgacc atgaagccac cctgaggtgc      660
tgggccctga gcttctaccc tgcggagatc acactgacct ggcagcggga tggggaggac      720
cagacccagg acacggagct cgtggagacc aggcctgcag gggatggaac cttccagaag      780
tgggcggctg tggtggtgcc ttctggacag gagcagagat acacctgcca tgtgcagcat      840
gagggtttgc ccaagcccct caccctgaga tgggagccgg cagccacca ccaccatcac      900 cattga                                                                 906

<210> SEQ ID NO 2
<211> LENGTH: 302
<212> TYPE: PRT
<213> ORGANISM: Homo sapiens

<400> SEQUENCE: 2

Met Met Arg Pro Ile Val Leu Val Leu Leu Phe Ala Thr Ser Ala Leu
1               5                   10                  15

Ala Gly Ser His Ser Met Arg Tyr Phe Phe Thr Ser Val Ser Arg Pro
            20                  25                  30

Gly Arg Gly Glu Pro Arg Phe Ile Ala Val Gly Tyr Val Asp Asp Thr
        35                  40                  45

Gln Phe Val Arg Phe Asp Ser Asp Ala Ala Ser Gln Arg Met Glu Pro
    50                  55                  60

Arg Ala Pro Trp Ile Glu Gln Glu Gly Pro Glu Tyr Trp Asp Gly Glu
65                  70                  75                  80

Thr Arg Lys Val Lys Ala His Ser Gln Thr His Arg Val Asp Leu Gly
                85                  90                  95

Thr Leu Arg Gly Tyr Tyr Asn Gln Ser Glu Ala Gly Ser His Thr Val
            100                 105                 110

Gln Arg Met Tyr Gly Cys Asp Val Gly Ser Asp Trp Arg Phe Leu Arg
        115                 120                 125

Gly Tyr His Gln Tyr Ala Tyr Asp Gly Lys Asp Tyr Ile Ala Leu Lys
    130                 135                 140

Glu Asp Leu Arg Ser Trp Thr Ala Ala Asp Met Ala Ala Gln Thr Thr
145                 150                 155                 160

Lys His Lys Trp Glu Ala Ala His Val Ala Glu Gln Leu Arg Ala Tyr
                165                 170                 175

Leu Glu Gly Thr Cys Val Glu Trp Leu Arg Arg Tyr Leu Glu Asn Gly
            180                 185                 190

Lys Glu Thr Leu Gln Arg Thr Asp Ala Pro Lys Thr His Met Thr His
        195                 200                 205

His Ala Val Ser Asp His Glu Ala Thr Leu Arg Cys Trp Ala Leu Ser
```

```
                210             215                 220
Phe Tyr Pro Ala Glu Ile Thr Leu Thr Trp Gln Arg Asp Gly Glu Asp
225                 230                 235                 240

Gln Thr Gln Asp Thr Glu Leu Val Glu Thr Arg Pro Ala Gly Asp Gly
                245                 250                 255

Thr Phe Gln Lys Trp Ala Ala Val Val Pro Ser Gly Gln Glu Gln
            260                 265                 270

Arg Tyr Thr Cys His Val Gln His Glu Gly Leu Pro Lys Pro Leu Thr
        275                 280                 285

Leu Arg Trp Glu Pro Gly Ser His His His His His Glx
    290                 295                 300

<210> SEQ ID NO 3
<211> LENGTH: 906
<212> TYPE: DNA
<213> ORGANISM: Homo sapiens

<400> SEQUENCE: 3
atgatgcggc ccatcgtgct ggtgctgctg tttgccacat ctgccctggc cggaagccac      60
agcatgcggt acttttttcac cagcgtgtcc agacccggca gaggcgagcc cagattcatt    120
gccgtgggct acgtggacga cacccagttc gtcagattcg acagcgacgc cgccagccag    180
cggatggaac ctagagcccc ttggatcgag caggaaggcc ccgagtactg ggacggcgag    240
acacggaaag tgaaggccca cagccagacc cacagagtgg atctgggcac cctgcggggc    300
tactacaatc agtctgaggc cggctcccac accgtgcaga ggatgtacgg ctgtgacgtg    360
ggcagcgact ggcggttcct gagaggctac caccagtacg cctacgacgg caaggactat    420
atcgccctga agaggaccct gcggagctgg acagccgccg atatggccgc ccagaccacc    480
aagcacaaat gggaagccgc ccacgtggcc gagcagctga gagcttatct ggaaggcacc    540
tgtgtggaat ggctgcggag ataccctgga aacggcaaag agacactgca gcgcacagat    600
tccccaaagg cccatgtgac ccatcacagc agacctgaag ataaagtcac cctgaggtgc    660
tgggccctgg gcttctaccc tgctgacatc accctgacct ggcagttgaa tgggaggag    720 ctgatccagg acatggagct gtgtgagacc aggcctgcag gggatggaac cttccagaag    780
tgggcatctg tggtggtgcc tcttgggaag gagcagtatt acacatgcca tgtgtaccat    840
caggggctgc ctgagcccct caccctgaga tgggagccgg gcagccacca ccaccatcac    900
cattga                                                                906

<210> SEQ ID NO 4
<211> LENGTH: 302
<212> TYPE: PRT
<213> ORGANISM: Homo sapiens

<400> SEQUENCE: 4

Met Met Arg Pro Ile Val Leu Val Leu Leu Phe Ala Thr Ser Ala Leu
1               5                   10                  15

Ala Gly Ser His Ser Met Arg Tyr Phe Phe Thr Ser Val Ser Arg Pro
            20                  25                  30

Gly Arg Gly Glu Pro Arg Phe Ile Ala Val Gly Tyr Val Asp Asp Thr
        35                  40                  45

Gln Phe Val Arg Phe Asp Ser Asp Ala Ala Ser Gln Arg Met Glu Pro
    50                  55                  60

Arg Ala Pro Trp Ile Glu Gln Glu Gly Pro Glu Tyr Trp Asp Gly Glu
65                  70                  75                  80
```

```
Thr Arg Lys Val Lys Ala His Ser Gln Thr His Arg Val Asp Leu Gly
            85                  90                  95
Thr Leu Arg Gly Tyr Tyr Asn Gln Ser Glu Ala Gly Ser His Thr Val
            100                 105                 110
Gln Arg Met Tyr Gly Cys Asp Val Gly Ser Asp Trp Arg Phe Leu Arg
            115                 120                 125
Gly Tyr His Gln Tyr Ala Tyr Asp Gly Lys Asp Tyr Ile Ala Leu Lys
            130                 135                 140
Glu Asp Leu Arg Ser Trp Thr Ala Ala Asp Met Ala Ala Gln Thr Thr
145                 150                 155                 160
Lys His Lys Trp Glu Ala Ala His Val Ala Glu Gln Leu Arg Ala Tyr
                165                 170                 175
Leu Glu Gly Thr Cys Val Glu Trp Leu Arg Arg Tyr Leu Glu Asn Gly
                180                 185                 190
Lys Glu Thr Leu Gln Arg Thr Asp Ser Pro Lys Ala His Val Thr His
                195                 200                 205
His Ser Arg Pro Glu Asp Lys Val Thr Leu Arg Cys Trp Ala Leu Gly
            210                 215                 220
Phe Tyr Pro Ala Asp Ile Thr Leu Thr Trp Gln Leu Asn Gly Glu Glu
225                 230                 235                 240
Leu Ile Gln Asp Met Glu Leu Val Glu Thr Arg Pro Ala Gly Asp Gly
                245                 250                 255
Thr Phe Gln Lys Trp Ala Ser Val Val Val Pro Leu Gly Lys Glu Gln
                260                 265                 270
Tyr Tyr Thr Cys His Val Tyr His Gln Gly Leu Pro Glu Pro Leu Thr
                275                 280                 285
Leu Arg Trp Glu Pro Gly Ser His His His His His Glx
            290                 295                 300

<210> SEQ ID NO 5
<211> LENGTH: 906
<212> TYPE: DNA
<213> ORGANISM: Homo sapiens

<400> SEQUENCE: 5
atgatgcggc ccatcgtgct ggtgctgctg tttgccacat ctgccctggc cggaagccac     60
agcatgcggt actttttcac cagcgtgtcc agacccggca gaggcgagcc cagattcatt    120
gccgtgggct acgtggacga cacccagttc gtcagattcg acagcgacgc cgccagccag    180
cggatggaac ctagagcccc ttggatcgag caggaaggcc ccgagtactg gacggcgag     240
acacggaaag tgaaggccca gccagacc cacagagtgg atctgggcac cctgcggggc     300
tactacaatc agtctgaggc cggctcccac accgtgcaga ggatgtacgg ctgtgacgtg    360
ggcagcgact ggcggttcct gagaggctac cacgagtacg cctacgacgg caaggactat    420
atcgccctga agaggaccct gcggagctgg acagccgccg atatggccgc ccagaccacc    480
aagcacaaat gggaagccgc ccacgtggcc gagcagctga gcttatct ggaaggcacc     540
tgtgtggaat ggctgcggag atacctggaa aacggcaaag agacactgca gcgcacagat    600
tccccaaagg cccatgtgac ccatcacagc agacctgaag ataaagtcac ctgaggtgc     660
tgggccctgg gcttctaccc tgctgacatc accctgacct ggcagttgaa tggggaggag    720
ctgatccagg acatggagct tgtggagacc aggcctgcag gggatggaac cttccagaag    780
tgggcatctg tggtggtgcc tcttgggaag gagcagtatt acacatgcca tgtgtaccat    840
```

-continued cagggggctgc ctgagcccct caccctgaga tgggagccgg gcagccacca ccaccatcac   900
cattga   906

<210> SEQ ID NO 6
<211> LENGTH: 302
<212> TYPE: PRT
<213> ORGANISM: Homo sapiens

<400> SEQUENCE: 6

Met Met Arg Pro Ile Val Leu Val Leu Leu Phe Ala Thr Ser Ala Leu
1               5                   10                  15

Ala Gly Ser His Ser Met Arg Tyr Phe Phe Thr Ser Val Ser Arg Pro
            20                  25                  30

Gly Arg Gly Glu Pro Arg Phe Ile Ala Val Gly Tyr Val Asp Asp Thr
        35                  40                  45

Gln Phe Val Arg Phe Asp Ser Asp Ala Ala Ser Gln Arg Met Glu Pro
    50                  55                  60

Arg Ala Pro Trp Ile Glu Gln Glu Gly Pro Glu Tyr Trp Asp Gly Glu
65                  70                  75                  80

Thr Arg Lys Val Lys Ala His Ser Gln Thr His Arg Val Asp Leu Gly
                85                  90                  95

Thr Leu Arg Gly Tyr Tyr Asn Gln Ser Glu Ala Gly Ser His Thr Val
            100                 105                 110

Gln Arg Met Tyr Gly Cys Asp Val Gly Ser Asp Trp Arg Phe Leu Arg
        115                 120                 125

Gly Tyr His Glu Tyr Ala Tyr Asp Gly Lys Asp Tyr Ile Ala Leu Lys
    130                 135                 140

Glu Asp Leu Arg Ser Trp Thr Ala Ala Asp Met Ala Ala Gln Thr Thr
145                 150                 155                 160

Lys His Lys Trp Glu Ala Ala His Val Ala Glu Gln Leu Arg Ala Tyr
                165                 170                 175

Leu Glu Gly Thr Cys Val Glu Trp Leu Arg Arg Tyr Leu Glu Asn Gly
            180                 185                 190

Lys Glu Thr Leu Gln Arg Thr Asp Ser Pro Lys Ala His Val Thr His
        195                 200                 205

His Ser Arg Pro Glu Asp Lys Val Thr Leu Arg Cys Trp Ala Leu Gly
    210                 215                 220

Phe Tyr Pro Ala Asp Ile Thr Leu Thr Trp Gln Leu Asn Gly Glu Glu
225                 230                 235                 240

Leu Ile Gln Asp Met Glu Leu Val Glu Thr Arg Pro Ala Gly Asp Gly
                245                 250                 255

Thr Phe Gln Lys Trp Ala Ser Val Val Val Pro Leu Gly Lys Glu Gln
            260                 265                 270

Tyr Tyr Thr Cys His Val Tyr His Gln Gly Leu Pro Glu Pro Leu Thr
        275                 280                 285

Leu Arg Trp Glu Pro Gly Ser His His His His His Glx
    290                 295                 300

<210> SEQ ID NO 7
<211> LENGTH: 906
<212> TYPE: DNA
<213> ORGANISM: Homo sapiens

<400> SEQUENCE: 7
atgatgcggc ccatcgtgct ggtgctgctg tttgccacat ctgccctggc cggctcccac   60

```
tccatgaggt atttctccac atccgtgtcc cggcccggcc gcgggagcc ccgcttcatc    120 gccgtgggct acgtggacga cacgcagttc gtgcggttcg acagcgacgc cgcgagccag    180
aggatggagc cgcgggcgcc gtggatagag caggaggggc cggagtattg ggacgaggag    240
acagggaaag tgaaggccca ctcacagact gaccgagaga acctgcggat cgcgctccgc    300
tactacaacc agagcgaggc cggttctcac accctccaga tgatgtttgg ctgcgacgtg    360 gggtcgacg gcgcttcct ccgcgggtac caccagtacg cctacgacgg caaggattac    420
atcgccctga agaggacct gcgctcttgg accgcggcgg acatggcggc tcagatcacc    480
aagcgcaagt gggaggcggc ccatgtggcg gagcagcaga gagcctacct ggagggcacg    540
tgcgtggacg ggctccgcag atacctggag aacgggaagg agacgctgca gcgcacggac    600 cccccaaga cacatatgac ccaccacccc atctctgacc atgaggccac tctgagatgc    660
tgggccctgg gcttctaccc tgcggagatc acactgacct ggcagcggga tggggaggac    720
cagacccagg acacggagct tgtggagacc aggcctgcag gggatggaac cttccagaag    780
tgggcagctg tggtggtacc ttctggagag gagcagagat acacctgcca tgtgcagcat    840
gagggtctgc ccaagcccct caccctgaga tgggagccgg cagccacca ccaccatcac    900 cattga                                                                906
```

```
<210> SEQ ID NO 8
<211> LENGTH: 302
<212> TYPE: PRT
<213> ORGANISM: Homo sapiens

<400> SEQUENCE: 8

Met Met Arg Pro Ile Val Leu Val Leu Leu Phe Ala Thr Ser Ala Leu
1               5                   10                  15

Ala Gly Ser His Ser Met Arg Tyr Phe Ser Thr Ser Val Ser Arg Pro
            20                  25                  30

Gly Arg Gly Glu Pro Arg Phe Ile Ala Val Gly Tyr Val Asp Asp Thr
        35                  40                  45

Gln Phe Val Arg Phe Asp Ser Asp Ala Ala Ser Gln Arg Met Glu Pro
    50                  55                  60

Arg Ala Pro Trp Ile Glu Gln Glu Gly Pro Glu Tyr Trp Asp Glu Glu
65                  70                  75                  80

Thr Gly Lys Val Lys Ala His Ser Gln Thr Asp Arg Glu Asn Leu Arg
                85                  90                  95

Ile Ala Leu Arg Tyr Tyr Asn Gln Ser Glu Ala Gly Ser His Thr Leu
            100                 105                 110

Gln Met Met Phe Gly Cys Asp Val Gly Ser Asp Gly Arg Phe Leu Arg
        115                 120                 125

Gly Tyr His Gln Tyr Ala Tyr Asp Gly Lys Asp Tyr Ile Ala Leu Lys
    130                 135                 140

Glu Asp Leu Arg Ser Trp Thr Ala Ala Asp Met Ala Ala Gln Ile Thr
145                 150                 155                 160

Lys Arg Lys Trp Glu Ala Ala His Val Ala Glu Gln Gln Arg Ala Tyr
                165                 170                 175

Leu Glu Gly Thr Cys Val Asp Gly Leu Arg Arg Tyr Leu Glu Asn Gly
            180                 185                 190

Lys Glu Thr Leu Gln Arg Thr Asp Pro Pro Lys Thr His Met Thr His
        195                 200                 205

His Pro Ile Ser Asp His Glu Ala Thr Leu Arg Cys Trp Ala Leu Gly
    210                 215                 220
```

-continued

```
Phe Tyr Pro Ala Glu Ile Thr Leu Thr Trp Gln Arg Asp Gly Glu Asp
225                 230                 235                 240

Gln Thr Gln Asp Thr Glu Leu Val Glu Thr Arg Pro Ala Gly Asp Gly
            245                 250                 255

Thr Phe Gln Lys Trp Ala Ala Val Val Val Pro Ser Gly Glu Glu Gln
        260                 265                 270

Arg Tyr Thr Cys His Val Gln His Glu Gly Leu Pro Lys Pro Leu Thr
    275                 280                 285

Leu Arg Trp Glu Pro Gly Ser His His His His His Glx
290                 295                 300
```

<210> SEQ ID NO 9
<211> LENGTH: 906
<212> TYPE: DNA
<213> ORGANISM: Homo sapiens

<400> SEQUENCE: 9

```
atgatgcggc ccatcgtgct ggtgctgctg tttgccacat ctgccctggc cggctcccac     60
tccatgaggt atttctccac atccgtgtcc cggcccggcc gcgggagcc ccgcttcatc    120
gccgtgggct acgtggacga cacgcagttc gtgcggttcg acagcgacgc cgcgagccag    180
aggatggagc cgcgggcgcc gtggatagag caggaggggc cggagtattg ggacgaggag    240
acagggaaag tgaaggccca ctcacagact gaccgagaga acctgcggat cgcgctccgc    300
tactacaacc agagcgaggc cggttctcac accctccaga tgatgtttgg ctgcgacgtg    360
gggtcggacg gcgcttcct ccgcgggtac caccagtacg cctacgacgg caaggattac    420
atcgccctga agaggacct gcgctcttgg accgcggcgg acatggcggc tcagatcacc    480
aagcgcaagt gggaggcggc ccatgtggcg agcagcaga gagcctacct ggagggcacg    540
tgcgtggacg ggctccgcag atacctggag aacgggaagg agacgctgca gcgcacagat    600
tccccaaagg cccatgtgac ccatcacagc agacctgaag ataaagtcac cctgaggtgc    660
tgggccctgg gcttctaccc tgctgacatc accctgacct ggcagttgaa tggggaggag    720
ctgatccagg acatggagct tgtggagacc aggcctgcag gggatggaac cttccagaag    780
tgggcatctg tggtggtgcc tcttgggaag gagcagtatt acacatgcca tgtgtaccat    840
caggggctgc ctgagcccct caccctgaga tgggagccgg cagccacca ccaccatcac    900
cattga                                                              906
```

<210> SEQ ID NO 10
<211> LENGTH: 302
<212> TYPE: PRT
<213> ORGANISM: Homo sapiens

<400> SEQUENCE: 10

```
Met Met Arg Pro Ile Val Leu Val Leu Leu Phe Ala Thr Ser Ala Leu
1               5                   10                  15

Ala Gly Ser His Ser Met Arg Tyr Phe Ser Thr Ser Val Ser Arg Pro
            20                  25                  30

Gly Arg Gly Glu Pro Arg Phe Ile Ala Val Gly Tyr Val Asp Asp Thr
        35                  40                  45

Gln Phe Val Arg Phe Asp Ser Asp Ala Ala Ser Gln Arg Met Glu Pro
    50                  55                  60

Arg Ala Pro Trp Ile Glu Gln Glu Gly Pro Glu Tyr Trp Asp Glu Glu
65              70                  75                  80
```

Thr Gly Lys Val Lys Ala His Ser Gln Thr Asp Arg Glu Asn Leu Arg
                85                  90                  95

Ile Ala Leu Arg Tyr Tyr Asn Gln Ser Glu Ala Gly Ser His Thr Leu
            100                 105                 110

Gln Met Met Phe Gly Cys Asp Val Gly Ser Asp Gly Arg Phe Leu Arg
            115                 120                 125

Gly Tyr His Gln Tyr Ala Tyr Asp Gly Lys Asp Tyr Ile Ala Leu Lys
        130                 135                 140

Glu Asp Leu Arg Ser Trp Thr Ala Ala Asp Met Ala Ala Gln Ile Thr
145                 150                 155                 160

Lys Arg Lys Trp Glu Ala Ala His Val Ala Glu Gln Gln Arg Ala Tyr
                165                 170                 175

Leu Glu Gly Thr Cys Val Asp Gly Leu Arg Arg Tyr Leu Glu Asn Gly
            180                 185                 190

Lys Glu Thr Leu Gln Arg Thr Asp Ser Pro Lys Ala His Val Thr His
        195                 200                 205

His Ser Arg Pro Glu Asp Lys Val Thr Leu Arg Cys Trp Ala Leu Gly
    210                 215                 220

Phe Tyr Pro Ala Asp Ile Thr Leu Thr Trp Gln Leu Asn Gly Glu Glu
225                 230                 235                 240

Leu Ile Gln Asp Met Glu Leu Val Glu Thr Arg Pro Ala Gly Asp Gly
                245                 250                 255

Thr Phe Gln Lys Trp Ala Ser Val Val Pro Leu Gly Lys Glu Gln
            260                 265                 270

Tyr Tyr Thr Cys His Val Tyr His Gln Gly Leu Pro Glu Pro Leu Thr
        275                 280                 285

Leu Arg Trp Glu Pro Gly Ser His His His His His Glx
    290                 295                 300

<210> SEQ ID NO 11
<211> LENGTH: 906
<212> TYPE: DNA
<213> ORGANISM: Homo sapiens

<400> SEQUENCE: 11

```
atgatgcggc ccatcgtgct ggtgctgctg tttgccacat ctgccctggc cggctcccac      60
tccatgaggt atttctccac atccgtgtcc cggcccggcc gcggggagcc ccgcttcatc     120
gccgtgggct acgtggacga cacgcagttc gtgcggttcg acagcgacgc cgcgagccag     180
aggatggagc gcgggcgcc gtggatagag caggagggc ggagtattg ggacgaggag        240 acagggaaag tgaaggccca ctcacagact gaccgagaga acctgcggat cgcgctccgc     300
tactacaacc agagcgaggc cggttctcac accctccaga tgatgtttgg ctgcgacgtg     360
gggtcggacg gcgcttcct ccgcgggtac cacgagtacg cctacgacgg caaggattac      420
atcgccctga agaggaccct cgctcttgg accgcggcgg acatggcggc tcagatcacc      480
aagcgcaagt gggaggcggc ccatgtggcg gagcagcaga gagcctacct ggagggcacg     540
tgcgtggacg ggctccgcag ataccctgag aacgggaagg agacgctgca gcgcacagat     600
tccccaaagg cccatgtgac ccatcacagc agacctgaag ataaagtcac cctgaggtgc     660
tgggccctgg gcttctaccc tgctgacatc accctgacct ggcagttgaa tggggaggag     720
ctgatccagg acatggagct gtggagacc aggcctgcag gggatggaac cttccagaag     780
tgggcatctg tggtggtgcc tcttgggaag gagcagtatt acacatgcca tgtgtaccat     840
caggggctgc ctgagcccct caccctgaga tgggagccgg gcagccacca ccaccatcac     900
``` cattga                                                                906

<210> SEQ ID NO 12
<211> LENGTH: 302
<212> TYPE: PRT
<213> ORGANISM: Homo sapiens

<400> SEQUENCE: 12

Met Met Arg Pro Ile Val Leu Val Leu Leu Phe Ala Thr Ser Ala Leu
1               5                   10                  15

Ala Gly Ser His Ser Met Arg Tyr Phe Ser Thr Ser Val Ser Arg Pro
            20                  25                  30

Gly Arg Gly Glu Pro Arg Phe Ile Ala Val Gly Tyr Val Asp Asp Thr
        35                  40                  45

Gln Phe Val Arg Phe Asp Ser Asp Ala Ala Ser Gln Arg Met Glu Pro
    50                  55                  60

Arg Ala Pro Trp Ile Glu Gln Glu Gly Pro Glu Tyr Trp Asp Glu Glu
65                  70                  75                  80

Thr Gly Lys Val Lys Ala His Ser Gln Thr Asp Arg Glu Asn Leu Arg
                85                  90                  95

Ile Ala Leu Arg Tyr Tyr Asn Gln Ser Glu Ala Gly Ser His Thr Leu
            100                 105                 110

Gln Met Met Phe Gly Cys Asp Val Gly Ser Asp Gly Arg Phe Leu Arg
        115                 120                 125

Gly Tyr His Glu Tyr Ala Tyr Asp Gly Lys Asp Tyr Ile Ala Leu Lys
    130                 135                 140

Glu Asp Leu Arg Ser Trp Thr Ala Ala Asp Met Ala Ala Gln Ile Thr
145                 150                 155                 160

Lys Arg Lys Trp Glu Ala Ala His Val Ala Glu Gln Gln Arg Ala Tyr
                165                 170                 175

Leu Glu Gly Thr Cys Val Asp Gly Leu Arg Arg Tyr Leu Glu Asn Gly
            180                 185                 190

Lys Glu Thr Leu Gln Arg Thr Asp Ser Pro Lys Ala His Val Thr His
        195                 200                 205

His Ser Arg Pro Glu Asp Lys Val Thr Leu Arg Cys Trp Ala Leu Gly
    210                 215                 220

Phe Tyr Pro Ala Asp Ile Thr Leu Thr Trp Gln Leu Asn Gly Glu Glu
225                 230                 235                 240

Leu Ile Gln Asp Met Glu Leu Val Glu Thr Arg Pro Ala Gly Asp Gly
                245                 250                 255

Thr Phe Gln Lys Trp Ala Ser Val Val Val Pro Leu Gly Lys Glu Gln
            260                 265                 270

Tyr Tyr Thr Cys His Val Tyr His Gln Gly Leu Pro Glu Pro Leu Thr
        275                 280                 285

Leu Arg Trp Glu Pro Gly Ser His His His His His Glx
    290                 295                 300

<210> SEQ ID NO 13
<211> LENGTH: 906
<212> TYPE: DNA
<213> ORGANISM: Homo sapiens

<400> SEQUENCE: 13
atgatgcggc ccatcgtgct ggtgctgctg tttgccacat ctgccctggc cggctcccac     60
tccatgaggt atttctacac cgccatgtcc cggcccggcc gcggggagcc ccgcttcatc    120

```
gcagtgggct acgtggacga cacccagttc gtgaggttcg acagcgacgc cgcgagtccg    180
aggacggagc cccgggcgcc atggatagag caggaggggc cggagtattg ggaccggaac    240
acacagatct tcaagaccaa cacacagact taccgagaga gcctgcggaa cctgcgcggc    300
tactacaacc agagcgaggc cgggtctcac atcatccaga ggatgtatgg ctgcgacctg    360
gggcccgacg gcgcctcct ccgcgggcat gacgagtccg cctacgacgg caaggattac    420
atcgccctga cgaggaccct gagctcctgg accgcggcgg acaccgcggc tcagatcacc    480
cagcgcaagt gggaggcggc ccgtgtggcg gagcagctga gagcctacct ggagggcctg    540
tgcgtggagt ggctccgcag atacctggag aacgggaagg agacgctgca gcgcacagat    600
tccccaaagg cccatgtgac ccatcacagc agacctgaag ataaagtcac cctgaggtgc    660
tgggccctgg gcttctaccc tgctgacatc accctgacct ggcagttgaa tgggga ggag    720 ctgatccagg acatggagct tgtggagacc aggcctgcag gggatggaac cttccagaag    780
tgggcatctg tggtggtgcc tcttgggaag gagcagtatt acacatgcca tgtgtaccat    840
caggggctgc ctgagcccct caccctgaga tgggagccgg gcagccacca ccaccatcac    900
cattga                                                                906
```

<210> SEQ ID NO 14
<211> LENGTH: 302
<212> TYPE: PRT
<213> ORGANISM: Homo sapiens

<400> SEQUENCE: 14

```
Met Met Arg Pro Ile Val Leu Val Leu Leu Phe Ala Thr Ser Ala Leu
1               5                   10                  15

Ala Gly Ser His Ser Met Arg Tyr Phe Tyr Thr Ala Met Ser Arg Pro
            20                  25                  30

Gly Arg Gly Glu Pro Arg Phe Ile Ala Val Gly Tyr Val Asp Asp Thr
        35                  40                  45

Gln Phe Val Arg Phe Asp Ser Asp Ala Ala Ser Pro Arg Thr Glu Pro
    50                  55                  60

Arg Ala Pro Trp Ile Glu Gln Glu Gly Pro Glu Tyr Trp Asp Arg Asn
65                  70                  75                  80

Thr Gln Ile Phe Lys Thr Asn Thr Gln Thr Tyr Arg Glu Ser Leu Arg
                85                  90                  95

Asn Leu Arg Gly Tyr Tyr Asn Gln Ser Glu Ala Gly Ser His Ile Ile
            100                 105                 110

Gln Arg Met Tyr Gly Cys Asp Leu Gly Pro Asp Gly Arg Leu Leu Arg
        115                 120                 125

Gly His Asp Glu Ser Ala Tyr Asp Gly Lys Asp Tyr Ile Ala Leu Asn
    130                 135                 140

Glu Asp Leu Ser Ser Trp Thr Ala Ala Asp Thr Ala Ala Gln Ile Thr
145                 150                 155                 160

Gln Arg Lys Trp Glu Ala Ala Arg Val Ala Glu Gln Leu Arg Ala Tyr
                165                 170                 175

Leu Glu Gly Leu Cys Val Glu Trp Leu Arg Arg Tyr Leu Glu Asn Gly
            180                 185                 190

Lys Glu Thr Leu Gln Arg Thr Asp Ser Pro Lys Ala His Val Thr His
        195                 200                 205

His Ser Arg Pro Glu Asp Lys Val Thr Leu Arg Cys Trp Ala Leu Gly
    210                 215                 220
```

```
Phe Tyr Pro Ala Asp Ile Thr Leu Thr Trp Gln Leu Asn Gly Glu Glu
225                 230                 235                 240

Leu Ile Gln Asp Met Glu Leu Val Glu Thr Arg Pro Ala Gly Asp Gly
            245                 250                 255

Thr Phe Gln Lys Trp Ala Ser Val Val Val Pro Leu Gly Lys Glu Gln
        260                 265                 270

Tyr Tyr Thr Cys His Val Tyr His Gln Gly Leu Pro Glu Pro Leu Thr
    275                 280                 285

Leu Arg Trp Glu Pro Gly Ser His His His His His Glx
    290                 295                 300
```

<210> SEQ ID NO 15
<211> LENGTH: 906
<212> TYPE: DNA
<213> ORGANISM: Homo sapiens

<400> SEQUENCE: 15

```
atgatgcggc ccatcgtgct ggtgctgctg tttgccacat ctgccctggc cggcagccac      60
agcatgcggt acttccacac cagcgtgtcc agacccggaa gaggcgagcc cagattcatc     120
accgtgggct acgtggacga caccctgttc gtcagattcg acagcgacgc caccagcccc     180
cggaaagaac ctagagcccc ttggatcgag caggaaggcc ccgagtactg ggacagagag     240
acacagatca gcaagaccaa cacccagacc tacagagaga cctgcggaa cctgcggggc     300
tactacaatc agagcgaggc cggctctcac accctgcagt ctatgtacgg ctgcgacgtg     360
ggccccgatg cagactgct gagaggccac aacgagtacg cctacgacgg caaggactat     420
atcgccctga cgaggacct gcggagctgg acagccgccg atacagccgc ccagatcacc     480
cagagaaagt gggaggccgc cagagtggcc gaacagctga gagcctatct ggaaggcgag     540
tgcgtggaat ggctgcggag atacctggaa aacggcaaag agacactgca gcgcacagat     600
tccccaaagg cccatgtgac ccatcacagc agacctgaag ataaagtcac cctgaggtgc     660
tgggccctgg gcttctaccc tgctgacatc accctgacct ggcagttgaa tggggaggag     720
ctgatccagg acatggagct gtgtgagacc aggcctgcag gggatggaac cttccagaag     780
tgggcatctg tggtggtgcc tcttgggaag gagcagtatt acacatgcca tgtgtaccat     840
caggggctgc ctgagcccct caccctgaga tgggagccgg cagccacca ccaccatcac     900
cattga                                                                906
```

<210> SEQ ID NO 16
<211> LENGTH: 302
<212> TYPE: PRT
<213> ORGANISM: Homo sapiens

<400> SEQUENCE: 16

```
Met Met Arg Pro Ile Val Leu Val Leu Leu Phe Ala Thr Ser Ala Leu
1               5                   10                  15

Ala Gly Ser His Ser Met Arg Tyr Phe His Thr Ser Val Ser Arg Pro
            20                  25                  30

Gly Arg Gly Glu Pro Arg Phe Ile Thr Val Gly Tyr Val Asp Asp Thr
        35                  40                  45

Leu Phe Val Arg Phe Asp Ser Asp Ala Thr Ser Pro Arg Lys Glu Pro
    50                  55                  60

Arg Ala Pro Trp Ile Glu Gln Glu Gly Pro Glu Tyr Trp Asp Arg Glu
65                  70                  75                  80

Thr Gln Ile Ser Lys Thr Asn Thr Gln Thr Tyr Arg Glu Ser Leu Arg
```

```
                     85                  90                  95
Asn Leu Arg Gly Tyr Tyr Asn Gln Ser Glu Ala Gly Ser His Thr Leu
                100                 105                 110

Gln Ser Met Tyr Gly Cys Asp Val Gly Pro Asp Gly Arg Leu Leu Arg
            115                 120                 125

Gly His Asn Glu Tyr Ala Tyr Asp Gly Lys Asp Tyr Ile Ala Leu Asn
        130                 135                 140

Glu Asp Leu Arg Ser Trp Thr Ala Ala Asp Thr Ala Ala Gln Ile Thr
145                 150                 155                 160

Gln Arg Lys Trp Glu Ala Ala Arg Val Ala Glu Gln Leu Arg Ala Tyr
                165                 170                 175

Leu Glu Gly Glu Cys Val Glu Trp Leu Arg Arg Tyr Leu Glu Asn Gly
                180                 185                 190

Lys Glu Thr Leu Gln Arg Thr Asp Ser Pro Lys Ala His Val Thr His
                195                 200                 205

His Ser Arg Pro Glu Asp Lys Val Thr Leu Arg Cys Trp Ala Leu Gly
        210                 215                 220

Phe Tyr Pro Ala Asp Ile Thr Leu Thr Trp Gln Leu Asn Gly Glu Glu
225                 230                 235                 240

Leu Ile Gln Asp Met Glu Leu Val Glu Thr Arg Pro Ala Gly Asp Gly
                245                 250                 255

Thr Phe Gln Lys Trp Ala Ser Val Val Pro Leu Gly Lys Glu Gln
            260                 265                 270

Tyr Tyr Thr Cys His Val Tyr His Gln Gly Leu Pro Glu Pro Leu Thr
            275                 280                 285

Leu Arg Trp Glu Pro Gly Ser His His His His His Glx
        290                 295                 300

<210> SEQ ID NO 17
<211> LENGTH: 906
<212> TYPE: DNA
<213> ORGANISM: Homo sapiens

<400> SEQUENCE: 17
atgatgaggc ccatcgtgct ggtgctgctg ttcgccacat ctgccctggc cggcagccac      60
agcatgcggt acttttacac cgccatgagc agacccggca gaggcgagcc cagattcatc     120
accgtgggct acgtggacga caccctgttc gtcagattcg acagcgacgc caccagcccc     180
cggaaagaac ctagagcccc ttggatcgag caggaaggcc ccgagtactg ggacagagag     240
acacagatca gcaagaccaa cacccagacc tacagagaga cctgcggac cgccctgcgg     300 tactacaatc agtctgaggc cggctcccac atcatccagc ggatgtacgg ctgtgacgtg     360
ggccccgatg cagactgct gagaggctac gacgagtacg cctacgacgg caaggactat     420
atcgccctga cgaggacct gagcagctgg acagccgccg atacagccgc ccagatcacc     480
cagagaaagt gggaggccgc cagagtggcc gagcaggata gagcctatct ggaaggcctg     540
tgcgtggaaa gcctgcggag atacctggaa aacggcaaag agacactgca gcgcacagat     600
tccccaaagg cccatgtgac ccatcacagc agacctgaag ataaagtcac cctgaggtgc     660
tgggccctgg gcttctaccc tgctgacatc accctgacct ggcagttgaa tggggaggag     720
ctgatccagg acatggagct tgtggagacc aggcctgcag gggatggaac cttccagaag     780
tgggcatctg tggtggtgcc tcttgggaag gagcagtatt acacatgcca tgtgtaccat     840 cagggggctgc ctgagcccct caccctgaga tgggagccgg gcagccacca ccaccatcac     900
``` cattga                                                                                        906

<210> SEQ ID NO 18
<211> LENGTH: 302
<212> TYPE: PRT
<213> ORGANISM: Homo sapiens

<400> SEQUENCE: 18

Met Met Arg Pro Ile Val Leu Val Leu Leu Phe Ala Thr Ser Ala Leu
1               5                   10                  15

Ala Gly Ser His Ser Met Arg Tyr Phe Tyr Thr Ala Met Ser Arg Pro
            20                  25                  30

Gly Arg Gly Glu Pro Arg Phe Ile Thr Val Gly Tyr Val Asp Asp Thr
        35                  40                  45

Leu Phe Val Arg Phe Asp Ser Asp Ala Thr Ser Pro Arg Lys Glu Pro
    50                  55                  60

Arg Ala Pro Trp Ile Glu Gln Glu Gly Pro Glu Tyr Trp Asp Arg Glu
65                  70                  75                  80

Thr Gln Ile Ser Lys Thr Asn Thr Gln Thr Tyr Arg Glu Asn Leu Arg
                85                  90                  95

Thr Ala Leu Arg Tyr Tyr Asn Gln Ser Glu Ala Gly Ser His Ile Ile
            100                 105                 110

Gln Arg Met Tyr Gly Cys Asp Val Gly Pro Asp Gly Arg Leu Leu Arg
        115                 120                 125

Gly Tyr Asp Glu Tyr Ala Tyr Asp Gly Lys Asp Tyr Ile Ala Leu Asn
    130                 135                 140

Glu Asp Leu Ser Ser Trp Thr Ala Ala Asp Thr Ala Ala Gln Ile Thr
145                 150                 155                 160

Gln Arg Lys Trp Glu Ala Ala Arg Val Ala Glu Gln Asp Arg Ala Tyr
                165                 170                 175

Leu Glu Gly Leu Cys Val Glu Ser Leu Arg Arg Tyr Leu Glu Asn Gly
            180                 185                 190

Lys Glu Thr Leu Gln Arg Thr Asp Ser Pro Lys Ala His Val Thr His
        195                 200                 205

His Ser Arg Pro Glu Asp Lys Val Thr Leu Arg Cys Trp Ala Leu Gly
    210                 215                 220

Phe Tyr Pro Ala Asp Ile Thr Leu Thr Trp Gln Leu Asn Gly Glu Glu
225                 230                 235                 240

Leu Ile Gln Asp Met Glu Leu Val Glu Thr Arg Pro Ala Gly Asp Gly
                245                 250                 255

Thr Phe Gln Lys Trp Ala Ser Val Val Val Pro Leu Gly Lys Glu Gln
            260                 265                 270

Tyr Tyr Thr Cys His Val Tyr His Gln Gly Leu Pro Glu Pro Leu Thr
        275                 280                 285

Leu Arg Trp Glu Pro Gly Ser His His His His His Glx
    290                 295                 300

<210> SEQ ID NO 19
<211> LENGTH: 906
<212> TYPE: DNA
<213> ORGANISM: Homo sapiens

<400> SEQUENCE: 19
atgatgcggc ccatcgtgct ggtgctgctg tttgccacat ctgccctggc cggcagccac        60
agcatgcggt acttttacac cagcgtgtcc agacccggca gaggcgagcc cagattcatc       120

```
agcgtgggct acgtggacga cacccagttc gtcagattcg acagcgacgc cgccagcccc    180
agagaggaac ctagagcccc ttggatcgag caggaaggcc ccgagtactg ggaccggaac    240
acccagatct acaaggccca gcccagacc gacagagaga gcctgagaaa cctgcgggc     300
```

```
agcgtgggct acgtggacga cacccagttc gtcagattcg acagcgacgc cgccagcccc    180
agagaggaac ctagagcccc ttggatcgag caggaaggcc ccgagtactg ggaccggaac    240
acccagatct acaaggccca gcccagacc  gacagagaga gcctgagaaa cctgcggggc    300
tactacaacc agagcgaggc cggctctcac accctgcagt ctatgtacgg ctgcgacgtg    360
ggccccgatg gcagactgct gagaggccac gatgagtacg cctacgacgg caaggactat    420
atcgccctga cgaggacct  gcggagctgg acagccgccg atacagccgc ccagatcacc    480
cagagaaagt gggaggccgc cagagaggcc gaacagagaa gggcctatct ggaaggcgag    540
tgcgtggaat ggctgcggag atacctggaa aatggcaagg acaagctgga acgcacagat    600
tccccaaagg cccatgtgac ccatcacagc agacctgaag ataaagtcac cctgaggtgc    660
tgggccctgg gcttctaccc tgctgacatc acccctgacct ggcagttgaa tggggaggag    720
ctgatccaga catggagct  tgtggagacc aggcctgcag gggatggaac cttccagaag    780
tgggcatctg tggtggtgcc tcttgggaag gagcagtatt acacatgcca tgtgtaccat    840
cagggggctgc ctgagcccct caccctgaga tgggagccgg cagccacca ccaccatcac    900
cattga                                                                906
```

<210> SEQ ID NO 20
<211> LENGTH: 302
<212> TYPE: PRT
<213> ORGANISM: Homo sapiens

<400> SEQUENCE: 20

```
Met Met Arg Pro Ile Val Leu Val Leu Leu Phe Ala Thr Ser Ala Leu
 1               5                  10                  15

Ala Gly Ser His Ser Met Arg Tyr Phe Tyr Thr Ser Val Ser Arg Pro
                20                  25                  30

Gly Arg Gly Glu Pro Arg Phe Ile Ser Val Gly Tyr Val Asp Asp Thr
            35                  40                  45

Gln Phe Val Arg Phe Asp Ser Asp Ala Ala Ser Pro Arg Glu Glu Pro
        50                  55                  60

Arg Ala Pro Trp Ile Glu Gln Glu Gly Pro Glu Tyr Trp Asp Arg Asn
65                  70                  75                  80

Thr Gln Ile Tyr Lys Ala Gln Ala Gln Thr Asp Arg Glu Ser Leu Arg
                85                  90                  95

Asn Leu Arg Gly Tyr Tyr Asn Gln Ser Glu Ala Gly Ser His Thr Leu
            100                 105                 110

Gln Ser Met Tyr Gly Cys Asp Val Gly Pro Asp Gly Arg Leu Leu Arg
        115                 120                 125

Gly His Asp Glu Tyr Ala Tyr Asp Gly Lys Asp Tyr Ile Ala Leu Asn
    130                 135                 140

Glu Asp Leu Arg Ser Trp Thr Ala Ala Asp Thr Ala Ala Gln Ile Thr
145                 150                 155                 160

Gln Arg Lys Trp Glu Ala Ala Arg Glu Ala Glu Gln Arg Arg Ala Tyr
                165                 170                 175

Leu Glu Gly Glu Cys Val Glu Trp Leu Arg Arg Tyr Leu Glu Asn Gly
            180                 185                 190

Lys Asp Lys Leu Glu Arg Thr Asp Ser Pro Lys Ala His Val Thr His
        195                 200                 205

His Ser Arg Pro Glu Asp Lys Val Thr Leu Arg Cys Trp Ala Leu Gly
    210                 215                 220

Phe Tyr Pro Ala Asp Ile Thr Leu Thr Trp Gln Leu Asn Gly Glu Glu
```

```
                225                 230                 235                 240
Leu Ile Gln Asp Met Glu Leu Val Glu Thr Arg Pro Ala Gly Asp Gly
                    245                 250                 255

Thr Phe Gln Lys Trp Ala Ser Val Val Val Pro Leu Gly Lys Glu Gln
                260                 265                 270

Tyr Tyr Thr Cys His Val Tyr His Gln Gly Leu Pro Glu Pro Leu Thr
            275                 280                 285

Leu Arg Trp Glu Pro Gly Ser His His His His His Glx
        290                 295                 300

<210> SEQ ID NO 21
<211> LENGTH: 906
<212> TYPE: DNA
<213> ORGANISM: Homo sapiens

<400> SEQUENCE: 21
atgatgcggc ccatcgtgct ggtgctgctg tttgccacat ctgccctggc cggcagccac      60
agcatgcggt actttgacac cgccatgagc agacccggca gaggcgagcc agattcatc     120 agcgtgggct acgtggacga cacccagttc gtcagattcg acagcgacgc cgccagcccc    180
agagaggaac ctagagcccc ttggatcgag caggaaggcc ccgagtactg ggaccggaac    240
acccagatct tcaagaccaa tacccagacc gacagagaga gcctgcggaa cctgcggggc    300
tactacaatc agagcgaggc cggctctcac accctgcagt ctatgtacgg ctgcgacgtg    360
ggccccgatg gcagactgct gagaggccac aacgagtacg cctacgacgg caaggactat    420
atcgccctga cgaggacct gcggagctgg acagccgccg atacagccgc ccagatcacc    480
cagagaaagt gggaggccgc cagagtggcc gagcaggata gagcctacct ggaaggcacc    540
tgtgtggaat ggctgcggag atacctggaa aatggcaagg acaccctgga acgcacagat    600
tccccaaagg cccatgtgac ccatcacagc agacctgaag ataaagtcac cctgaggtgc    660 tgggcccctgg gcttctaccc tgctgacatc accctgacct ggcagttgaa tgggggaggag    720 ctgatccagg acatggagct tgtggagacc aggcctgcag gggatggaac cttccagaag    780
tgggcatctg tggtggtgcc tcttgggaag gagcagtatt acacatgcca tgtgtaccat    840
caggggctgc ctgagcccct caccctgaga tgggagccgg gcagccacca ccaccatcac    900
cattga                                                              906

<210> SEQ ID NO 22
<211> LENGTH: 302
<212> TYPE: PRT
<213> ORGANISM: Homo sapiens

<400> SEQUENCE: 22

Met Met Arg Pro Ile Val Leu Val Leu Leu Phe Ala Thr Ser Ala Leu
1               5                   10                  15

Ala Gly Ser His Ser Met Arg Tyr Phe Asp Thr Ala Met Ser Arg Pro
            20                  25                  30

Gly Arg Gly Glu Pro Arg Phe Ile Ser Val Gly Tyr Val Asp Asp Thr
        35                  40                  45

Gln Phe Val Arg Phe Asp Ser Asp Ala Ala Ser Pro Arg Glu Glu Pro
    50                  55                  60

Arg Ala Pro Trp Ile Glu Gln Glu Gly Pro Glu Tyr Trp Asp Arg Asn
65                  70                  75                  80

Thr Gln Ile Phe Lys Thr Asn Thr Gln Thr Asp Arg Glu Ser Leu Arg
                85                  90                  95
```

```
Asn Leu Arg Gly Tyr Tyr Asn Gln Ser Glu Ala Gly Ser His Thr Leu
                100                 105                 110

Gln Ser Met Tyr Gly Cys Asp Val Gly Pro Asp Gly Arg Leu Leu Arg
            115                 120                 125

Gly His Asn Glu Tyr Ala Tyr Asp Gly Lys Asp Tyr Ile Ala Leu Asn
        130                 135                 140

Glu Asp Leu Arg Ser Trp Thr Ala Ala Asp Thr Ala Ala Gln Ile Thr
145                 150                 155                 160

Gln Arg Lys Trp Glu Ala Ala Arg Val Ala Glu Gln Asp Arg Ala Tyr
                165                 170                 175

Leu Glu Gly Thr Cys Val Glu Trp Leu Arg Arg Tyr Leu Glu Asn Gly
            180                 185                 190

Lys Asp Thr Leu Glu Arg Thr Asp Ser Pro Lys Ala His Val Thr His
        195                 200                 205

His Ser Arg Pro Glu Asp Lys Val Thr Leu Arg Cys Trp Ala Leu Gly
    210                 215                 220

Phe Tyr Pro Ala Asp Ile Thr Leu Thr Trp Gln Leu Asn Gly Glu Glu
225                 230                 235                 240

Leu Ile Gln Asp Met Glu Leu Val Glu Thr Arg Pro Ala Gly Asp Gly
                245                 250                 255

Thr Phe Gln Lys Trp Ala Ser Val Val Val Pro Leu Gly Lys Glu Gln
            260                 265                 270

Tyr Tyr Thr Cys His Val Tyr His Gln Gly Leu Pro Glu Pro Leu Thr
        275                 280                 285

Leu Arg Trp Glu Pro Gly Ser His His His His His Glx
    290                 295                 300

<210> SEQ ID NO 23
<211> LENGTH: 906
<212> TYPE: DNA
<213> ORGANISM: Homo sapiens

<400> SEQUENCE: 23
atgatgcggc ccatcgtgct ggtgctgctg tttgccacaa gcgccctggc ctgctctcac    60
agcatgcgct atttttacac ggcagttagt cggcctggga ggggtgagcc gagattcatt   120
gctgtaggct acgtagacga cactcaattt gtacagttcg actcagacgc tgcttcaccg   180
cgaggagagc ccagggcacc ctgggtagaa caagaagggc ccgaatactg ggatcgagaa   240
acccagaagt ataagaggca agcacaaact gatcgggtca acttgagaaa actgcgaggc   300
tactataatc aaagtgaggc aggatcccat acacttcaga ggatgtatgg ctgcgacctt   360
ggtccagatg gccggctcct cagagggtat aacgaatttg catacgacgg aaggattac    420 atagctctca atgaggacct tagatcatgg acggcagcgg ataaggcagc ccaaattact   480
caaaggaaat gggaggcggc ccgagaagca gagcagagaa gagcctacct ggaaggtaca   540
tgcgtggagt ggcttcggcg ctatctcgaa aacggtaaaa agacattgca acgcacagat   600
tccccaaagg cccatgtgac ccatcacagc agacctgaag ataaagtcac cctgaggtgc   660
tgggccctgg gcttctaccc tgctgacatc accctgacct ggcagttgaa tggggaggag   720
ctgatccagg acatggagct tgtggagacc aggcctgcag ggatggaac cttccagaag   780 tgggcatctg tggtggtgcc tcttgggaag gagcagtatt acacatgcca tgtgtaccat   840
caggggctgc ctgagcccct caccctgaga tgggagccgg gcagccacca ccaccatcac   900
cattga                                                              906
```

<210> SEQ ID NO 24
<211> LENGTH: 302
<212> TYPE: PRT
<213> ORGANISM: Homo sapiens

<400> SEQUENCE: 24

Met Met Arg Pro Ile Val Leu Val Leu Leu Phe Ala Thr Ser Ala Leu
1               5                   10                  15

Ala Cys Ser His Ser Met Arg Tyr Phe Tyr Thr Ala Val Ser Arg Pro
            20                  25                  30

Gly Arg Gly Glu Pro Arg Phe Ile Ala Val Gly Tyr Val Asp Asp Thr
        35                  40                  45

Gln Phe Val Gln Phe Asp Ser Asp Ala Ala Ser Pro Arg Gly Glu Pro
    50                  55                  60

Arg Ala Pro Trp Val Glu Gln Glu Gly Pro Glu Tyr Trp Asp Arg Glu
65                  70                  75                  80

Thr Gln Lys Tyr Lys Arg Gln Ala Gln Thr Asp Arg Val Asn Leu Arg
                85                  90                  95

Lys Leu Arg Gly Tyr Tyr Asn Gln Ser Glu Ala Gly Ser His Thr Leu
            100                 105                 110

Gln Arg Met Tyr Gly Cys Asp Leu Gly Pro Asp Gly Arg Leu Leu Arg
        115                 120                 125

Gly Tyr Asn Glu Phe Ala Tyr Asp Gly Lys Asp Tyr Ile Ala Leu Asn
    130                 135                 140

Glu Asp Leu Arg Ser Trp Thr Ala Ala Asp Lys Ala Ala Gln Ile Thr
145                 150                 155                 160

Gln Arg Lys Trp Glu Ala Ala Arg Glu Ala Glu Gln Arg Arg Ala Tyr
                165                 170                 175

Leu Glu Gly Thr Cys Val Glu Trp Leu Arg Arg Tyr Leu Glu Asn Gly
            180                 185                 190

Lys Lys Thr Leu Gln Arg Thr Asp Ser Pro Lys Ala His Val Thr His
        195                 200                 205

His Ser Arg Pro Glu Asp Lys Val Thr Leu Arg Cys Trp Ala Leu Gly
    210                 215                 220

Phe Tyr Pro Ala Asp Ile Thr Leu Thr Trp Gln Leu Asn Gly Glu Glu
225                 230                 235                 240

Leu Ile Gln Asp Met Glu Leu Val Glu Thr Arg Pro Ala Gly Asp Gly
                245                 250                 255

Thr Phe Gln Lys Trp Ala Ser Val Val Val Pro Leu Gly Lys Glu Gln
            260                 265                 270

Tyr Tyr Thr Cys His Val Tyr His Gln Gly Leu Pro Glu Pro Leu Thr
        275                 280                 285

Leu Arg Trp Glu Pro Gly Ser His His His His His Glx
    290                 295                 300

<210> SEQ ID NO 25
<211> LENGTH: 906
<212> TYPE: DNA
<213> ORGANISM: Homo sapiens

<400> SEQUENCE: 25
atgatgcggc ccatcgtgct ggtgctgctg tttgccacaa gcgccctggc ctgcagccac    60
agcatgcggt actttgacac cgccgtgtcc agacccggaa gaggcgagcc cagattcatc   120
agcgtgggct acgtggacga cacccagttc gtcagattcg acagcgacgc cgccagcccc   180

```
agaggcgaac ctagagcacc ttgggtggaa caggaaggcc ccgagtactg ggacagagag    240
acacagaact acaagcggca ggcccaggcc gacagagtgt ccctgagaaa cctgcgggc     300 tactacaacc agagcgagga cggcagccac accctgcaga gaatgtacgg ctgtgacctg    360
ggccccgatg gcagactgct gagaggctac gatgagagcg cctacgacgg caaggactat    420
atcgccctga acgaggacct gcggagctgg acagccgccg atacagccgc ccagatcacc    480
cagagaaaac tggaagccgc cagagccgcc gagcagctga gagcttatct ggaaggcacc    540
tgtgtggaat ggctgcggag atacctggaa aacggcaaag agacactgca gcgcacagat    600
tccccaaagg cccatgtgac ccatcacagc agacctgaag ataaagtcac cctgaggtgc    660
tgggccctgg gcttctaccc tgctgacatc accctgacct ggcagttgaa tggggaggag    720
ctgatccagg acatggagct gtggagacc aggcctgcag gggatggaac cttccagaag    780
tgggcatctg tggtggtgcc tcttgggaag gagcagtatt acacatgcca tgtgtaccat    840
caggggctgc ctgagcccct caccctgaga tgggagccgg cagccacca ccaccatcac    900 cattga                                                               906
```

```
<210> SEQ ID NO 26
<211> LENGTH: 302
<212> TYPE: PRT
<213> ORGANISM: Homo sapiens

<400> SEQUENCE: 26

Met Met Arg Pro Ile Val Leu Val Leu Leu Phe Ala Thr Ser Ala Leu
1               5                   10                  15

Ala Cys Ser His Ser Met Arg Tyr Phe Asp Thr Ala Val Ser Arg Pro
                20                  25                  30

Gly Arg Gly Glu Pro Arg Phe Ile Ser Val Gly Tyr Val Asp Asp Thr
            35                  40                  45

Gln Phe Val Arg Phe Asp Ser Asp Ala Ala Ser Pro Arg Gly Glu Pro
        50                  55                  60

Arg Ala Pro Trp Val Glu Gln Glu Gly Pro Glu Tyr Trp Asp Arg Glu
65                  70                  75                  80

Thr Gln Asn Tyr Lys Arg Gln Ala Gln Ala Asp Arg Val Ser Leu Arg
                85                  90                  95

Asn Leu Arg Gly Tyr Tyr Asn Gln Ser Glu Asp Gly Ser His Thr Leu
            100                 105                 110

Gln Arg Met Tyr Gly Cys Asp Leu Gly Pro Asp Gly Arg Leu Leu Arg
        115                 120                 125

Gly Tyr Asp Glu Ser Ala Tyr Asp Gly Lys Asp Tyr Ile Ala Leu Asn
    130                 135                 140

Glu Asp Leu Arg Ser Trp Thr Ala Ala Asp Thr Ala Ala Gln Ile Thr
145                 150                 155                 160

Gln Arg Lys Leu Glu Ala Ala Arg Ala Ala Glu Gln Leu Arg Ala Tyr
                165                 170                 175

Leu Glu Gly Thr Cys Val Glu Trp Leu Arg Arg Tyr Leu Glu Asn Gly
            180                 185                 190

Lys Glu Thr Leu Gln Arg Thr Asp Ser Pro Lys Ala His Val Thr His
        195                 200                 205

His Ser Arg Pro Glu Asp Lys Val Thr Leu Arg Cys Trp Ala Leu Gly
    210                 215                 220

Phe Tyr Pro Ala Asp Ile Thr Leu Thr Trp Gln Leu Asn Gly Glu Glu
225                 230                 235                 240
```

```
Leu Ile Gln Asp Met Glu Leu Val Glu Thr Arg Pro Ala Gly Asp Gly
                245                 250                 255

Thr Phe Gln Lys Trp Ala Ser Val Val Pro Leu Gly Lys Glu Gln
            260                 265                 270

Tyr Tyr Thr Cys His Val Tyr His Gln Gly Leu Pro Glu Pro Leu Thr
        275                 280                 285

Leu Arg Trp Glu Pro Gly Ser His His His His His Glx
        290                 295                 300
```

<210> SEQ ID NO 27
<211> LENGTH: 906
<212> TYPE: DNA
<213> ORGANISM: Homo sapiens

<400> SEQUENCE: 27

```
atgatgcggc ccatcgtgct ggtgctgctg tttgccacat ctgccctggc ctgcagccac     60
agcatgcggt actttgacac cgccgtgtcc agacccggaa gaggcgagcc cagattcatc    120
agcgtgggct acgtggacga cacccagttc gtcagattcg acagcgacgc cgccagcccc    180
agaggcgaac ctagagcacc ttgggtggaa caggaaggcc ccgagtactg ggacagagag    240
acacagaagt acaagcggca gggccaggcc gacagagtgt ccctgagaaa cctgcggggc    300
tactacaacc agagcgagga cggcagccac accctgcaga gaatgagcgg ctgtgacctg    360
ggccccgatg cagactgct gagaggctac gatgagagcg cctacgacgg caaggactat    420
atcgccctga cgaggacct gcggagctgg acagccgccg atacagccgc ccagatcacc    480
cagagaaaac tggaagccgc cagagccgcc gagcagctga gagcttatct ggaaggcacc    540
tgtgtggaat ggctgcggag atacctggaa aacggcaaag agacactgca gcgcacagat    600
tccccaaagg cccatgtgac ccatcacagc agacctgaag ataaagtcac cctgaggtgc    660
tgggccctgg gcttctaccc tgctgacatc accctgacct ggcagttgaa tgggaggag    720
ctgatccagg acatggagct tgtggagacc aggcctgcag gggatggaac cttccagaag    780
tgggcatctg tggtggtgcc tcttgggaag gagcagtatt acacatgcca tgtgtaccat    840
cagggggctgc ctgagcccct caccctgaga tgggagccgg cagccacca ccaccatcac    900
cattga                                                               906
```

<210> SEQ ID NO 28
<211> LENGTH: 302
<212> TYPE: PRT
<213> ORGANISM: Homo sapiens

<400> SEQUENCE: 28

```
Met Met Arg Pro Ile Val Leu Val Leu Leu Phe Ala Thr Ser Ala Leu
1               5                   10                  15

Ala Cys Ser His Ser Met Arg Tyr Phe Asp Thr Ala Val Ser Arg Pro
            20                  25                  30

Gly Arg Gly Glu Pro Arg Phe Ile Ser Val Gly Tyr Val Asp Asp Thr
        35                  40                  45

Gln Phe Val Arg Phe Asp Ser Asp Ala Ala Ser Pro Arg Gly Glu Pro
    50                  55                  60

Arg Ala Pro Trp Val Glu Gln Glu Gly Pro Glu Tyr Trp Asp Arg Glu
65                  70                  75                  80

Thr Gln Lys Tyr Lys Arg Gln Ala Gln Ala Asp Arg Val Ser Leu Arg
                85                  90                  95
```

-continued

```
Asn Leu Arg Gly Tyr Tyr Asn Gln Ser Glu Asp Gly Ser His Thr Leu
            100                 105                 110

Gln Arg Met Ser Gly Cys Asp Leu Gly Pro Asp Gly Arg Leu Leu Arg
        115                 120                 125

Gly Tyr Asp Glu Ser Ala Tyr Asp Gly Lys Asp Tyr Ile Ala Leu Asn
    130                 135                 140

Glu Asp Leu Arg Ser Trp Thr Ala Ala Asp Thr Ala Ala Gln Ile Thr
145                 150                 155                 160

Gln Arg Lys Leu Glu Ala Ala Arg Ala Ala Glu Gln Leu Arg Ala Tyr
                165                 170                 175

Leu Glu Gly Thr Cys Val Glu Trp Leu Arg Arg Tyr Leu Glu Asn Gly
            180                 185                 190

Lys Glu Thr Leu Gln Arg Thr Asp Ser Pro Lys Ala His Val Thr His
        195                 200                 205

His Ser Arg Pro Glu Asp Lys Val Thr Leu Arg Cys Trp Ala Leu Gly
    210                 215                 220

Phe Tyr Pro Ala Asp Ile Thr Leu Thr Trp Gln Leu Asn Gly Glu Glu
225                 230                 235                 240

Leu Ile Gln Asp Met Glu Leu Val Glu Thr Arg Pro Ala Gly Asp Gly
                245                 250                 255

Thr Phe Gln Lys Trp Ala Ser Val Val Val Pro Leu Gly Lys Glu Gln
            260                 265                 270

Tyr Tyr Thr Cys His Val Tyr His Gln Gly Leu Pro Glu Pro Leu Thr
        275                 280                 285

Leu Arg Trp Glu Pro Gly Ser His His His His His His Glx
    290                 295                 300
```

<210> SEQ ID NO 29
<211> LENGTH: 906
<212> TYPE: DNA
<213> ORGANISM: Homo sapiens

<400> SEQUENCE: 29

```
atgatgaggc ccatcgtgct ggtgctgctg ttcgccacat ctgccctggc ctgcagccac      60
agcatgcggt acttttacac cgccgtgtcc agacccggca gaggcgagcc tagattcatt     120
gccgtgggct acgtggacga cacccagttc gtcagattcg acagcgacgc cgccagcccc     180
agaggggaac ctagagcacc ttgggtggaa caggaaggcc ccgagtactg ggacagagag     240
acacagaagt acaagcggca ggcccagacc gaccgggtgt ccctgagaaa cctgcggggc     300
tactacaacc agagcgaggc cggctctcac accctgcagt ggatgtacgg ctgcgacctg     360
ggccctgatg gcagactgct gagaggctac gacgagtccg cctacgacgg caaggactat     420
atcgccctga acgaggacct gcggagctgg acagccgccg atacagccgc ccagatcacc     480
cagagaaagt gggaagccgc cagagccgcc gagcagcaga gagcttatct ggaaggcacc     540
tgtgtggaat ggctgcggag atacctggaa aacggcaaag agacactgca gcgcacagat     600
tccccaaagg cccatgtgac ccatcacagc agacctgaag ataaagtcac cctgaggtgc     660
tgggccctgg gcttctaccc tgctgacatc accctgacct ggcagttgaa tggggaggag     720
ctgatccagg acatggagct tgtggagacc aggcctgcag gggatggaac cttccagaag     780
tgggcatctg tggtggtgcc tcttgggaag gagcagtatt acacatgcca tgtgtaccat     840
caggggctgc ctgagcccct caccctgaga tgggagccgg gcagccacca ccaccatcac     900
cattga                                                                906
```

<210> SEQ ID NO 30
<211> LENGTH: 302
<212> TYPE: PRT
<213> ORGANISM: Homo sapiens

<400> SEQUENCE: 30

```
Met Met Arg Pro Ile Val Leu Val Leu Leu Phe Ala Thr Ser Ala Leu
1               5                   10                  15
Ala Cys Ser His Ser Met Arg Tyr Phe Tyr Thr Ala Val Ser Arg Pro
            20                  25                  30
Gly Arg Gly Glu Pro Arg Phe Ile Ala Val Gly Tyr Val Asp Asp Thr
        35                  40                  45
Gln Phe Val Arg Phe Asp Ser Asp Ala Ala Ser Pro Arg Gly Glu Pro
    50                  55                  60
Arg Ala Pro Trp Val Glu Gln Glu Gly Pro Glu Tyr Trp Asp Arg Glu
65                  70                  75                  80
Thr Gln Lys Tyr Lys Arg Gln Ala Gln Thr Asp Arg Val Ser Leu Arg
                85                  90                  95
Asn Leu Arg Gly Tyr Tyr Asn Gln Ser Glu Ala Gly Ser His Thr Leu
            100                 105                 110
Gln Trp Met Tyr Gly Cys Asp Leu Gly Pro Asp Gly Arg Leu Leu Arg
        115                 120                 125
Gly Tyr Asp Glu Ser Ala Tyr Asp Gly Lys Asp Tyr Ile Ala Leu Asn
    130                 135                 140
Glu Asp Leu Arg Ser Trp Thr Ala Ala Asp Thr Ala Ala Gln Ile Thr
145                 150                 155                 160
Gln Arg Lys Trp Glu Ala Ala Arg Ala Ala Glu Gln Arg Ala Tyr
                165                 170                 175
Leu Glu Gly Thr Cys Val Glu Trp Leu Arg Arg Tyr Leu Glu Asn Gly
            180                 185                 190
Lys Glu Thr Leu Gln Arg Thr Asp Ser Pro Lys Ala His Val Thr His
        195                 200                 205
His Ser Arg Pro Glu Asp Lys Val Thr Leu Arg Cys Trp Ala Leu Gly
    210                 215                 220
Phe Tyr Pro Ala Asp Ile Thr Leu Thr Trp Gln Leu Asn Gly Glu Glu
225                 230                 235                 240
Leu Ile Gln Asp Met Glu Leu Val Glu Thr Arg Pro Ala Gly Asp Gly
                245                 250                 255
Thr Phe Gln Lys Trp Ala Ser Val Val Val Pro Leu Gly Lys Glu Gln
            260                 265                 270
Tyr Tyr Thr Cys His Val Tyr His Gln Gly Leu Pro Glu Pro Leu Thr
        275                 280                 285
Leu Arg Trp Glu Pro Gly Ser His His His His His Glx
    290                 295                 300
```

<210> SEQ ID NO 31
<211> LENGTH: 906
<212> TYPE: DNA
<213> ORGANISM: Homo sapiens

<400> SEQUENCE: 31
atgatgcggc ccatcgtgct ggtgctgctg tttgccacat ctgccctggc cggctcccac    60
tccatgaggt atttctacac cgccatgtcc cggcccggcc gcggggagcc ccgcttcatc   120
gcagtgggct acgtggacga cacccagttc gtgaggttcg acagcgacgc cgcgagtccg   180

-continued

```
aggacggagc cccgggcgcc atggatagag caggaggggc cggagtattg ggaccggaac    240
acacagatct tcaagaccaa cacacagact taccgagaga gcctgcggaa cctgcgcggc    300
tactacaacc agagcgaggc cgggtctcac atcatccaga ggatgtatgg ctgcgacctg    360
gggcccgacg gccgcctcct ccgcgggcat gaccagtccg cctacgacgg caaggattac    420
atcgccctga acgaggacct gagctcctgg accgcggcgg acaccgcggc tcagatcacc    480
cagcgcaagt gggaggcggc ccgtgtggcg gagcagctga gagcctacct ggagggcctg    540
tgcgtggagt ggctccgcag atacctggag aacgggaagg agacgctgca gcgcgcggac    600
cccccaaaga cacacgtgac ccaccacccc gtctctgacc atgaggccac cctgaggtgc    660
tgggccctgg gcttctaccc tgcggagatc acactgacct ggcagcggga tggcgaggac    720
caaactcagg acactgagct tgtggagacc agaccagcag agatagaac cttccagaag    780 tgggcagctg tggtggtgcc ttctggagaa gagcagagat acacatgcca tgtacagcat    840
gaggggctgc ccaagcccct caccctgaga tgggagccgg gcagccacca ccaccatcac    900
cattga                                                              906
```

<210> SEQ ID NO 32
<211> LENGTH: 302
<212> TYPE: PRT
<213> ORGANISM: Homo sapiens

<400> SEQUENCE: 32

```
Met Met Arg Pro Ile Val Leu Val Leu Leu Phe Ala Thr Ser Ala Leu
1               5                   10                  15

Ala Gly Ser His Ser Met Arg Tyr Phe Tyr Thr Ala Met Ser Arg Pro
                20                  25                  30

Gly Arg Gly Glu Pro Arg Phe Ile Ala Val Gly Tyr Val Asp Asp Thr
            35                  40                  45

Gln Phe Val Arg Phe Asp Ser Asp Ala Ala Ser Pro Arg Thr Glu Pro
        50                  55                  60

Arg Ala Pro Trp Ile Glu Gln Glu Gly Pro Glu Tyr Trp Asp Arg Asn
65                  70                  75                  80

Thr Gln Ile Phe Lys Thr Asn Thr Gln Thr Tyr Arg Glu Ser Leu Arg
                85                  90                  95

Asn Leu Arg Gly Tyr Tyr Asn Gln Ser Glu Ala Gly Ser His Ile Ile
            100                 105                 110

Gln Arg Met Tyr Gly Cys Asp Leu Gly Pro Asp Gly Arg Leu Leu Arg
        115                 120                 125

Gly His Asp Gln Ser Ala Tyr Asp Gly Lys Asp Tyr Ile Ala Leu Asn
    130                 135                 140

Glu Asp Leu Ser Ser Trp Thr Ala Ala Asp Thr Ala Ala Gln Ile Thr
145                 150                 155                 160

Gln Arg Lys Trp Glu Ala Ala Arg Val Ala Glu Gln Leu Arg Ala Tyr
                165                 170                 175

Leu Glu Gly Leu Cys Val Glu Trp Leu Arg Arg Tyr Leu Glu Asn Gly
            180                 185                 190

Lys Glu Thr Leu Gln Arg Ala Asp Pro Pro Lys Thr His Val Thr His
        195                 200                 205

His Pro Val Ser Asp His Glu Ala Thr Leu Arg Cys Trp Ala Leu Gly
    210                 215                 220

Phe Tyr Pro Ala Glu Ile Thr Leu Thr Trp Gln Arg Asp Gly Glu Asp
225                 230                 235                 240
```

Gln Thr Gln Asp Thr Glu Leu Val Glu Thr Arg Pro Ala Gly Asp Arg
            245                 250                 255

Thr Phe Gln Lys Trp Ala Ala Val Val Pro Ser Gly Glu Glu Gln
        260                 265                 270

Arg Tyr Thr Cys His Val Gln His Glu Gly Leu Pro Lys Pro Leu Thr
    275                 280                 285

Leu Arg Trp Glu Pro Gly Ser His His His His His Glx
        290                 295                 300

<210> SEQ ID NO 33
<211> LENGTH: 906
<212> TYPE: DNA
<213> ORGANISM: Homo sapiens

<400> SEQUENCE: 33
atgatgcggc ccatcgtgct ggtgctgctg tttgccacat ctgccctggc cggctcccac      60
tccatgaggt atttctacac cgccatgtcc cggcccggcc gcggggagcc ccgcttcatc     120
gcagtgggct acgtggacga cacccagttc gtgaggttcg acagcgacgc cgcgagtccg     180
aggacggagc cccgggcgcc atggatagag caggaggggc cggagtattg gaccggaac      240
acacagatct tcaagaccaa cacacagact taccgagaga gcctgcggaa cctgcgcggc     300
tactacaacc agagcgaggc cgggtctcac atcatccaga ggatgtatgg ctgcgacctg     360
gggcccgacg gcgcctcct ccgcgggcat gaccagtccg cctacgacgg caaggattac      420
atcgccctga cgaggacct gagctcctgg accgcggcgg acaccgcggc tcagatcacc      480
cagcgcaagt gggaggcggc ccgtgtggcg gagcagctga gagcctacct ggagggcctg     540
tgcgtggagt ggctccgcag atacctggag aacgggaagg agacgctgca gcgcacagat     600
tccccaaagg cccatgtgac ccatcacagc agacctgaag ataaagtcac cctgaggtgc     660
tgggccctgg gcttctaccc tgctgacatc accctgacct ggcagttgaa tggggaggag     720
ctgatccagg acatggagct tgtggagacc aggcctgcag gggatggaac cttccagaag     780
tgggcatctg tggtggtgcc tcttgggaag gagcagtatt acacatgcca tgtgtaccat     840
caggggctgc ctgagcccct caccctgaga tgggagccgg cagccacca ccaccatcac     900
cattga                                                                906

<210> SEQ ID NO 34
<211> LENGTH: 302
<212> TYPE: PRT
<213> ORGANISM: Homo sapiens

<400> SEQUENCE: 34

Met Met Arg Pro Ile Val Leu Val Leu Leu Phe Ala Thr Ser Ala Leu
1               5                   10                  15

Ala Gly Ser His Ser Met Arg Tyr Phe Tyr Thr Ala Met Ser Arg Pro
            20                  25                  30

Gly Arg Gly Glu Pro Arg Phe Ile Ala Val Gly Tyr Val Asp Asp Thr
        35                  40                  45

Gln Phe Val Arg Phe Asp Ser Asp Ala Ala Ser Pro Arg Thr Glu Pro
    50                  55                  60

Arg Ala Pro Trp Ile Glu Gln Glu Gly Pro Glu Tyr Trp Asp Arg Asn
65                  70                  75                  80

Thr Gln Ile Phe Lys Thr Asn Thr Gln Thr Tyr Arg Glu Ser Leu Arg
                85                  90                  95

Asn Leu Arg Gly Tyr Tyr Asn Gln Ser Glu Ala Gly Ser His Ile Ile

```
            100                 105                 110
Gln Arg Met Tyr Gly Cys Asp Leu Gly Pro Asp Gly Arg Leu Leu Arg
        115                 120                 125

Gly His Asp Gln Ser Ala Tyr Asp Gly Lys Asp Tyr Ile Ala Leu Asn
    130                 135                 140

Glu Asp Leu Ser Ser Trp Thr Ala Ala Asp Thr Ala Ala Gln Ile Thr
145                 150                 155                 160

Gln Arg Lys Trp Glu Ala Ala Arg Val Ala Glu Gln Leu Arg Ala Tyr
                165                 170                 175

Leu Glu Gly Leu Cys Val Glu Trp Leu Arg Arg Tyr Leu Glu Asn Gly
            180                 185                 190

Lys Glu Thr Leu Gln Arg Thr Asp Ser Pro Lys Ala His Val Thr His
        195                 200                 205

His Ser Arg Pro Glu Asp Lys Val Thr Leu Arg Cys Trp Ala Leu Gly
    210                 215                 220

Phe Tyr Pro Ala Asp Ile Thr Leu Thr Trp Gln Leu Asn Gly Glu Glu
225                 230                 235                 240

Leu Ile Gln Asp Met Glu Leu Val Glu Thr Arg Pro Ala Gly Asp Gly
                245                 250                 255

Thr Phe Gln Lys Trp Ala Ser Val Val Val Pro Leu Gly Lys Glu Gln
            260                 265                 270

Tyr Tyr Thr Cys His Val Tyr His Gln Gly Leu Pro Glu Pro Leu Thr
        275                 280                 285

Leu Arg Trp Glu Pro Gly Ser His His His His His Glx
    290                 295                 300

<210> SEQ ID NO 35
<211> LENGTH: 9
<212> TYPE: PRT
<213> ORGANISM: Artificial Sequence
<220> FEATURE:
<223> OTHER INFORMATION: Peptide fragment

<400> SEQUENCE: 35

Val Leu Asp Phe Ala Pro Pro Gly Ala
1               5

<210> SEQ ID NO 36
<211> LENGTH: 9
<212> TYPE: PRT
<213> ORGANISM: Artificial Sequence
<220> FEATURE:
<223> OTHER INFORMATION: Peptide fragment

<400> SEQUENCE: 36

Arg Met Phe Pro Asn Ala Pro Tyr Leu
1               5

<210> SEQ ID NO 37
<211> LENGTH: 9
<212> TYPE: PRT
<213> ORGANISM: Artificial Sequence
<220> FEATURE:
<223> OTHER INFORMATION: Peptide fragment

<400> SEQUENCE: 37

Ser Leu Gly Glu Gln Gln Tyr Ser Val
1               5

<210> SEQ ID NO 38
```

```
<211> LENGTH: 9
<212> TYPE: PRT
<213> ORGANISM: Artificial Sequence
<220> FEATURE:
<223> OTHER INFORMATION: Peptide fragment

<400> SEQUENCE: 38

Cys Met Thr Trp Asn Gln Met Asn Leu
1               5

<210> SEQ ID NO 39
<211> LENGTH: 9
<212> TYPE: PRT
<213> ORGANISM: Artificial Sequence
<220> FEATURE:
<223> OTHER INFORMATION: Peptide fragment

<400> SEQUENCE: 39

Tyr Met Ala Pro Asp Cys Arg Phe Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Peptide fragment

<400> SEQUENCE: 40

Arg Leu Gly Tyr Phe Pro Ser Ser Ile
1               5

<210> SEQ ID NO 41
<211> LENGTH: 9
<212> TYPE: PRT
<213> ORGANISM: Artificial Sequence
<220> FEATURE:
<223> OTHER INFORMATION: Peptide fragment

<400> SEQUENCE: 41

Leu Gln Leu Glu Glu Leu Glu Lys Val
1               5

<210> SEQ ID NO 42
<211> LENGTH: 9
<212> TYPE: PRT
<213> ORGANISM: Artificial Sequence
<220> FEATURE:
<223> OTHER INFORMATION: Peptide fragment

<400> SEQUENCE: 42

Glu Leu Thr Glu Ala Arg Val Gln Val
1               5

<210> SEQ ID NO 43
<211> LENGTH: 9
<212> TYPE: PRT
<213> ORGANISM: Artificial Sequence
<220> FEATURE:
<223> OTHER INFORMATION: Peptide fragment

<400> SEQUENCE: 43

Phe Leu Gly Asp Thr His Ser Ser Ile
1               5

<210> SEQ ID NO 44
<211> LENGTH: 9
```

```
<212> TYPE: PRT
<213> ORGANISM: Artificial Sequence
<220> FEATURE:
<223> OTHER INFORMATION: Peptide fragment

<400> SEQUENCE: 44

Ile Leu Ala Tyr Thr Glu Asp Glu Val
1               5

<210> SEQ ID NO 45
<211> LENGTH: 10
<212> TYPE: PRT
<213> ORGANISM: Artificial Sequence
<220> FEATURE:
<223> OTHER INFORMATION: Peptide fragment

<400> SEQUENCE: 45

Phe Leu Glu Glu Ile Lys Glu Gln Glu Val
1               5                   10

<210> SEQ ID NO 46
<211> LENGTH: 9
<212> TYPE: PRT
<213> ORGANISM: Artificial Sequence
<220> FEATURE:
<223> OTHER INFORMATION: Peptide fragment

<400> SEQUENCE: 46

Phe Met Ala Phe Val Ala Met Val Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Peptide fragment

<400> SEQUENCE: 47

Leu Leu Asp Glu Ala Thr Ser Ala Leu
1               5

<210> SEQ ID NO 48
<211> LENGTH: 9
<212> TYPE: PRT
<213> ORGANISM: Artificial Sequence
<220> FEATURE:
<223> OTHER INFORMATION: Peptide fragment

<400> SEQUENCE: 48

Val Leu Asn Gly Thr Val His Pro Val
1               5

<210> SEQ ID NO 49
<211> LENGTH: 9
<212> TYPE: PRT
<213> ORGANISM: Artificial Sequence
<220> FEATURE:
<223> OTHER INFORMATION: Peptide fragment

<400> SEQUENCE: 49

Val Leu Leu Ser Pro Arg Trp Glu Leu
1               5

<210> SEQ ID NO 50
<211> LENGTH: 9
<212> TYPE: PRT
```

<213> ORGANISM: Artificial Sequence
<220> FEATURE:
<223> OTHER INFORMATION: Peptide fragment

<400> SEQUENCE: 50

Phe Leu Trp Asp Ala Tyr Phe Ser Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Peptide fragment

<400> SEQUENCE: 51

Trp Leu Ala Leu Ser Ala Ser Trp Leu
1               5

<210> SEQ ID NO 52
<211> LENGTH: 9
<212> TYPE: PRT
<213> ORGANISM: Artificial Sequence
<220> FEATURE:
<223> OTHER INFORMATION: Peptide fragment

<400> SEQUENCE: 52

Leu Leu Leu Pro Gly Ile Tyr Thr Val
1               5

<210> SEQ ID NO 53
<211> LENGTH: 9
<212> TYPE: PRT
<213> ORGANISM: Artificial Sequence
<220> FEATURE:
<223> OTHER INFORMATION: Peptide fragment

<400> SEQUENCE: 53

Lys Leu Phe Gln Lys Leu Ala Lys Val
1               5

<210> SEQ ID NO 54
<211> LENGTH: 9
<212> TYPE: PRT
<213> ORGANISM: Artificial Sequence
<220> FEATURE:
<223> OTHER INFORMATION: Peptide fragment

<400> SEQUENCE: 54

Tyr Leu His Thr Asn Cys Phe Glu Ile
1               5

<210> SEQ ID NO 55
<211> LENGTH: 9
<212> TYPE: PRT
<213> ORGANISM: Artificial Sequence
<220> FEATURE:
<223> OTHER INFORMATION: Peptide fragment

<400> SEQUENCE: 55

Phe Leu Ser Asn Phe Pro Phe Ser Leu
1               5

<210> SEQ ID NO 56
<211> LENGTH: 9
<212> TYPE: PRT
<213> ORGANISM: Artificial Sequence

```
<220> FEATURE:
<223> OTHER INFORMATION: Peptide fragment

<400> SEQUENCE: 56

Ala Leu Ala Ile Gly Leu Trp Gly Leu
1               5

<210> SEQ ID NO 57
<211> LENGTH: 9
<212> TYPE: PRT
<213> ORGANISM: Artificial Sequence
<220> FEATURE:
<223> OTHER INFORMATION: Peptide fragment

<400> SEQUENCE: 57

Ala Leu Cys Glu Asn Thr Cys Leu Leu
1               5

<210> SEQ ID NO 58
<211> LENGTH: 9
<212> TYPE: PRT
<213> ORGANISM: Artificial Sequence
<220> FEATURE:
<223> OTHER INFORMATION: Peptide fragment

<400> SEQUENCE: 58

Leu Leu Tyr Pro Gly Tyr Ala Met Val
1               5

<210> SEQ ID NO 59
<211> LENGTH: 9
<212> TYPE: PRT
<213> ORGANISM: Artificial Sequence
<220> FEATURE:
<223> OTHER INFORMATION: Peptide fragment

<400> SEQUENCE: 59

Gly Leu Tyr Thr Leu Leu Ser Gly Val
1               5

<210> SEQ ID NO 60
<211> LENGTH: 9
<212> TYPE: PRT
<213> ORGANISM: Artificial Sequence
<220> FEATURE:
<223> OTHER INFORMATION: Peptide fragment

<400> SEQUENCE: 60

Ala Val Phe Met Tyr Val Phe Tyr Leu
1               5

<210> SEQ ID NO 61
<211> LENGTH: 9
<212> TYPE: PRT
<213> ORGANISM: Artificial Sequence
<220> FEATURE:
<223> OTHER INFORMATION: Peptide fragment

<400> SEQUENCE: 61

Leu Met Asp Asp Thr Leu Ser Pro Val
1               5

<210> SEQ ID NO 62
<211> LENGTH: 9
<212> TYPE: PRT
<213> ORGANISM: Artificial Sequence
<220> FEATURE:
```

<223> OTHER INFORMATION: Peptide fragment

<400> SEQUENCE: 62

Leu Gln Met Ala Asn Thr Leu Pro Val
1               5

<210> SEQ ID NO 63
<211> LENGTH: 9
<212> TYPE: PRT
<213> ORGANISM: Artificial Sequence
<220> FEATURE:
<223> OTHER INFORMATION: Peptide fragment

<400> SEQUENCE: 63

Leu Leu Ser Ser Val Ser Pro Gly Ala
1               5

<210> SEQ ID NO 64
<211> LENGTH: 9
<212> TYPE: PRT
<213> ORGANISM: Artificial Sequence
<220> FEATURE:
<223> OTHER INFORMATION: Peptide fragment

<400> SEQUENCE: 64

Ser Gln Phe Val Phe Ser Phe Pro Val
1               5

<210> SEQ ID NO 65
<211> LENGTH: 9
<212> TYPE: PRT
<213> ORGANISM: Artificial Sequence
<220> FEATURE:
<223> OTHER INFORMATION: Peptide fragment

<400> SEQUENCE: 65

Gln Leu Leu Gln Phe Glu Ser Gln Val
1               5

<210> SEQ ID NO 66
<211> LENGTH: 9
<212> TYPE: PRT
<213> ORGANISM: Artificial Sequence
<220> FEATURE:
<223> OTHER INFORMATION: Peptide fragment

<400> SEQUENCE: 66

Phe Leu Ala His Ser Ala Gly Tyr Ile
1               5

<210> SEQ ID NO 67
<211> LENGTH: 9
<212> TYPE: PRT
<213> ORGANISM: Artificial Sequence
<220> FEATURE:
<223> OTHER INFORMATION: Peptide fragment

<400> SEQUENCE: 67

Phe Leu Asp Arg Phe Leu Ser Cys Met
1               5

<210> SEQ ID NO 68
<211> LENGTH: 11
<212> TYPE: PRT
<213> ORGANISM: Artificial Sequence
<220> FEATURE:
<223> OTHER INFORMATION: Peptide fragment

<400> SEQUENCE: 68

Ser Leu Ile Ala Ala Ala Ala Phe Cys Leu Ala
1               5                   10

<210> SEQ ID NO 69
<211> LENGTH: 9
<212> TYPE: PRT
<213> ORGANISM: Artificial Sequence
<220> FEATURE:
<223> OTHER INFORMATION: Peptide fragment

<400> SEQUENCE: 69

Met Leu Ala Val Ile Ser Cys Ala Val
1               5

<210> SEQ ID NO 70
<211> LENGTH: 11
<212> TYPE: PRT
<213> ORGANISM: Artificial Sequence
<220> FEATURE:
<223> OTHER INFORMATION: Peptide fragment

<400> SEQUENCE: 70

Met Leu Met Ala Gln Glu Ala Leu Ala Phe Leu
1               5                   10

<210> SEQ ID NO 71
<211> LENGTH: 9
<212> TYPE: PRT
<213> ORGANISM: Artificial Sequence
<220> FEATURE:
<223> OTHER INFORMATION: Peptide fragment

<400> SEQUENCE: 71

Lys Val Leu Glu Tyr Val Ile Lys Val
1               5

<210> SEQ ID NO 72
<211> LENGTH: 10
<212> TYPE: PRT
<213> ORGANISM: Artificial Sequence
<220> FEATURE:
<223> OTHER INFORMATION: Peptide fragment

<400> SEQUENCE: 72

Tyr Leu Gln Leu Val Phe Gly Ile Glu Val
1               5                   10

<210> SEQ ID NO 73
<211> LENGTH: 9
<212> TYPE: PRT
<213> ORGANISM: Artificial Sequence
<220> FEATURE:
<223> OTHER INFORMATION: Peptide fragment

<400> SEQUENCE: 73

Phe Leu Trp Gly Pro Arg Ala Leu Val
1               5

<210> SEQ ID NO 74
<211> LENGTH: 9
<212> TYPE: PRT
<213> ORGANISM: Artificial Sequence
<220> FEATURE:
<223> OTHER INFORMATION: Peptide fragment

```
<400> SEQUENCE: 74

Lys Val Ala Glu Leu Val His Phe Leu
1               5

<210> SEQ ID NO 75
<211> LENGTH: 10
<212> TYPE: PRT
<213> ORGANISM: Artificial Sequence
<220> FEATURE:
<223> OTHER INFORMATION: Peptide fragment

<400> SEQUENCE: 75

Gly Val Tyr Asp Gly Arg Glu His Thr Val
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Peptide fragment

<400> SEQUENCE: 76

Ala Leu Ser Val Met Gly Val Tyr Val
1               5

<210> SEQ ID NO 77
<211> LENGTH: 9
<212> TYPE: PRT
<213> ORGANISM: Artificial Sequence
<220> FEATURE:
<223> OTHER INFORMATION: Peptide fragment

<400> SEQUENCE: 77

Gly Leu Tyr Asp Gly Met Glu His Leu
1               5

<210> SEQ ID NO 78
<211> LENGTH: 9
<212> TYPE: PRT
<213> ORGANISM: Artificial Sequence
<220> FEATURE:
<223> OTHER INFORMATION: Peptide fragment

<400> SEQUENCE: 78

Phe Leu Trp Gly Pro Arg Ala Leu Val
1               5

<210> SEQ ID NO 79
<211> LENGTH: 10
<212> TYPE: PRT
<213> ORGANISM: Artificial Sequence
<220> FEATURE:
<223> OTHER INFORMATION: Peptide fragment

<400> SEQUENCE: 79

Ile Leu Phe Gly Ile Ser Leu Arg Glu Val
1               5                   10

<210> SEQ ID NO 80
<211> LENGTH: 9
<212> TYPE: PRT
<213> ORGANISM: Artificial Sequence
<220> FEATURE:
<223> OTHER INFORMATION: Peptide fragment

<400> SEQUENCE: 80
```

```
Lys Val Val Glu Phe Leu Ala Met Leu
1               5

<210> SEQ ID NO 81
<211> LENGTH: 11
<212> TYPE: PRT
<213> ORGANISM: Artificial Sequence
<220> FEATURE:
<223> OTHER INFORMATION: Peptide fragment

<400> SEQUENCE: 81

Met Leu Met Ala Gln Glu Ala Leu Ala Phe Leu
1               5                   10

<210> SEQ ID NO 82
<211> LENGTH: 9
<212> TYPE: PRT
<213> ORGANISM: Artificial Sequence
<220> FEATURE:
<223> OTHER INFORMATION: Peptide fragment

<400> SEQUENCE: 82

Lys Ala Ser Glu Lys Ile Phe Tyr Val
1               5

<210> SEQ ID NO 83
<211> LENGTH: 9
<212> TYPE: PRT
<213> ORGANISM: Artificial Sequence
<220> FEATURE:
<223> OTHER INFORMATION: Peptide fragment

<400> SEQUENCE: 83

Arg Gln Lys Lys Ile Arg Ile Gln Leu
1               5

<210> SEQ ID NO 84
<211> LENGTH: 9
<212> TYPE: PRT
<213> ORGANISM: Artificial Sequence
<220> FEATURE:
<223> OTHER INFORMATION: Peptide fragment

<400> SEQUENCE: 84

Ile Met Ile Gly Val Leu Val Gly Val
1               5

<210> SEQ ID NO 85
<211> LENGTH: 9
<212> TYPE: PRT
<213> ORGANISM: Artificial Sequence
<220> FEATURE:
<223> OTHER INFORMATION: Peptide fragment

<400> SEQUENCE: 85

Lys Thr Trp Gly Gln Tyr Trp Gln Val
1               5

<210> SEQ ID NO 86
<211> LENGTH: 10
<212> TYPE: PRT
<213> ORGANISM: Artificial Sequence
<220> FEATURE:
<223> OTHER INFORMATION: Peptide fragment

<400> SEQUENCE: 86
```

Ala Met Leu Gly Thr His Thr Met Glu Val
1               5                   10

<210> SEQ ID NO 87
<211> LENGTH: 9
<212> TYPE: PRT
<213> ORGANISM: Artificial Sequence
<220> FEATURE:
<223> OTHER INFORMATION: Peptide fragment

<400> SEQUENCE: 87

Met Leu Gly Thr His Thr Met Glu Val
1               5

<210> SEQ ID NO 88
<211> LENGTH: 9
<212> TYPE: PRT
<213> ORGANISM: Artificial Sequence
<220> FEATURE:
<223> OTHER INFORMATION: Peptide fragment

<400> SEQUENCE: 88

Ile Thr Asp Gln Val Pro Phe Ser Val
1               5

<210> SEQ ID NO 89
<211> LENGTH: 9
<212> TYPE: PRT
<213> ORGANISM: Artificial Sequence
<220> FEATURE:
<223> OTHER INFORMATION: Peptide fragment

<400> SEQUENCE: 89

Tyr Leu Glu Pro Gly Pro Val Thr Ala
1               5

<210> SEQ ID NO 90
<211> LENGTH: 10
<212> TYPE: PRT
<213> ORGANISM: Artificial Sequence
<220> FEATURE:
<223> OTHER INFORMATION: Peptide fragment

<400> SEQUENCE: 90

Leu Leu Asp Gly Thr Ala Thr Leu Arg Leu
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Peptide fragment

<400> SEQUENCE: 91

Val Leu Tyr Arg Tyr Gly Ser Phe Ser Val
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Peptide fragment

<400> SEQUENCE: 92

Ser Leu Ala Asp Thr Asn Ser Leu Ala Val 1               5                  10

<210> SEQ ID NO 93
<211> LENGTH: 9
<212> TYPE: PRT
<213> ORGANISM: Artificial Sequence
<220> FEATURE:
<223> OTHER INFORMATION: Peptide fragment

<400> SEQUENCE: 93

Arg Leu Met Lys Gln Asp Phe Ser Val
1               5

<210> SEQ ID NO 94
<211> LENGTH: 9
<212> TYPE: PRT
<213> ORGANISM: Artificial Sequence
<220> FEATURE:
<223> OTHER INFORMATION: Peptide fragment

<400> SEQUENCE: 94

Arg Leu Pro Arg Ile Phe Cys Ser Cys
1               5

<210> SEQ ID NO 95
<211> LENGTH: 9
<212> TYPE: PRT
<213> ORGANISM: Artificial Sequence
<220> FEATURE:
<223> OTHER INFORMATION: Peptide fragment

<400> SEQUENCE: 95

Ser Leu Ser Lys Ile Leu Asp Thr Val
1               5

<210> SEQ ID NO 96
<211> LENGTH: 9
<212> TYPE: PRT
<213> ORGANISM: Artificial Sequence
<220> FEATURE:
<223> OTHER INFORMATION: Peptide fragment

<400> SEQUENCE: 96

Ser Val Tyr Asp Phe Phe Val Trp Leu
1               5

<210> SEQ ID NO 97
<211> LENGTH: 9
<212> TYPE: PRT
<213> ORGANISM: Artificial Sequence
<220> FEATURE:
<223> OTHER INFORMATION: Peptide fragment

<400> SEQUENCE: 97

Thr Leu Asp Ser Gln Val Met Ser Leu
1               5

<210> SEQ ID NO 98
<211> LENGTH: 9
<212> TYPE: PRT
<213> ORGANISM: Artificial Sequence
<220> FEATURE:
<223> OTHER INFORMATION: Peptide fragment

<400> SEQUENCE: 98

Met Leu Leu Ala Val Leu Tyr Cys Leu
1               5

```
<210> SEQ ID NO 99
<211> LENGTH: 10
<212> TYPE: PRT
<213> ORGANISM: Artificial Sequence
<220> FEATURE:
<223> OTHER INFORMATION: Peptide fragment

<400> SEQUENCE: 99

Cys Leu Leu Trp Ser Phe Gln Thr Ser Ala
1               5                   10

<210> SEQ ID NO 100
<211> LENGTH: 9
<212> TYPE: PRT
<213> ORGANISM: Artificial Sequence
<220> FEATURE:
<223> OTHER INFORMATION: Peptide fragment

<400> SEQUENCE: 100

Tyr Met Asp Gly Thr Met Ser Gln Val
1               5

<210> SEQ ID NO 101
<211> LENGTH: 9
<212> TYPE: PRT
<213> ORGANISM: Artificial Sequence
<220> FEATURE:
<223> OTHER INFORMATION: Peptide fragment

<400> SEQUENCE: 101

Leu Leu Asn Ala Phe Thr Val Thr Val
1               5

<210> SEQ ID NO 102
<211> LENGTH: 9
<212> TYPE: PRT
<213> ORGANISM: Artificial Sequence
<220> FEATURE:
<223> OTHER INFORMATION: Peptide fragment

<400> SEQUENCE: 102

Lys Val His Pro Val Ile Trp Ser Leu
1               5

<210> SEQ ID NO 103
<211> LENGTH: 10
<212> TYPE: PRT
<213> ORGANISM: Artificial Sequence
<220> FEATURE:
<223> OTHER INFORMATION: Peptide fragment

<400> SEQUENCE: 103

Leu Met Leu Gln Asn Ala Leu Thr Thr Met
1               5                   10

<210> SEQ ID NO 104
<211> LENGTH: 9
<212> TYPE: PRT
<213> ORGANISM: Artificial Sequence
<220> FEATURE:
<223> OTHER INFORMATION: Peptide fragment

<400> SEQUENCE: 104

Leu Leu Gly Ala Thr Cys Met Phe Val
1               5
```

<210> SEQ ID NO 105
<211> LENGTH: 9
<212> TYPE: PRT
<213> ORGANISM: Artificial Sequence
<220> FEATURE:
<223> OTHER INFORMATION: Peptide fragment

<400> SEQUENCE: 105

Ala Leu Leu Glu Ile Ala Ser Cys Leu
1               5

<210> SEQ ID NO 106
<211> LENGTH: 8
<212> TYPE: PRT
<213> ORGANISM: Artificial Sequence
<220> FEATURE:
<223> OTHER INFORMATION: Peptide fragment

<400> SEQUENCE: 106

Val Leu Phe Tyr Leu Gly Gln Tyr
1               5

<210> SEQ ID NO 107
<211> LENGTH: 9
<212> TYPE: PRT
<213> ORGANISM: Artificial Sequence
<220> FEATURE:
<223> OTHER INFORMATION: Peptide fragment

<400> SEQUENCE: 107

Leu Leu Gly Arg Asn Ser Phe Glu Val
1               5

<210> SEQ ID NO 108
<211> LENGTH: 9
<212> TYPE: PRT
<213> ORGANISM: Artificial Sequence
<220> FEATURE:
<223> OTHER INFORMATION: Peptide fragment

<400> SEQUENCE: 108

Arg Met Pro Glu Ala Ala Pro Pro Val
1               5

<210> SEQ ID NO 109
<211> LENGTH: 9
<212> TYPE: PRT
<213> ORGANISM: Artificial Sequence
<220> FEATURE:
<223> OTHER INFORMATION: Peptide fragment

<400> SEQUENCE: 109

Val Leu Asp Gly Leu Asp Val Leu Leu
1               5

<210> SEQ ID NO 110
<211> LENGTH: 10
<212> TYPE: PRT
<213> ORGANISM: Artificial Sequence
<220> FEATURE:
<223> OTHER INFORMATION: Peptide fragment

<400> SEQUENCE: 110

Ser Leu Tyr Ser Phe Pro Glu Pro Glu Ala
1               5                   10

```
<210> SEQ ID NO 111
<211> LENGTH: 10
<212> TYPE: PRT
<213> ORGANISM: Artificial Sequence
<220> FEATURE:
<223> OTHER INFORMATION: Peptide fragment

<400> SEQUENCE: 111

Ala Leu Tyr Val Asp Ser Leu Phe Phe Leu
1               5                   10

<210> SEQ ID NO 112
<211> LENGTH: 9
<212> TYPE: PRT
<213> ORGANISM: Artificial Sequence
<220> FEATURE:
<223> OTHER INFORMATION: Peptide fragment

<400> SEQUENCE: 112

Ser Leu Leu Gln His Leu Ile Gly Leu
1               5

<210> SEQ ID NO 113
<211> LENGTH: 9
<212> TYPE: PRT
<213> ORGANISM: Artificial Sequence
<220> FEATURE:
<223> OTHER INFORMATION: Peptide fragment

<400> SEQUENCE: 113

Ala Trp Ile Ser Lys Pro Pro Gly Val
1               5

<210> SEQ ID NO 114
<211> LENGTH: 10
<212> TYPE: PRT
<213> ORGANISM: Artificial Sequence
<220> FEATURE:
<223> OTHER INFORMATION: Peptide fragment

<400> SEQUENCE: 114

Ser Ala Trp Ile Ser Lys Pro Pro Gly Val
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Peptide fragment

<400> SEQUENCE: 115

Glu Leu Thr Leu Gly Glu Phe Leu Lys Leu
1               5                   10

<210> SEQ ID NO 116
<211> LENGTH: 9
<212> TYPE: PRT
<213> ORGANISM: Artificial Sequence
<220> FEATURE:
<223> OTHER INFORMATION: Peptide fragment

<400> SEQUENCE: 116

Arg Leu Val Asp Asp Phe Leu Leu Val
1               5

<210> SEQ ID NO 117
```

```
<211> LENGTH: 9
<212> TYPE: PRT
<213> ORGANISM: Artificial Sequence
<220> FEATURE:
<223> OTHER INFORMATION: Peptide fragment

<400> SEQUENCE: 117

Ala Ala Gly Ile Gly Ile Leu Thr Val
1               5

<210> SEQ ID NO 118
<211> LENGTH: 10
<212> TYPE: PRT
<213> ORGANISM: Artificial Sequence
<220> FEATURE:
<223> OTHER INFORMATION: Peptide fragment

<400> SEQUENCE: 118

Glu Leu Ala Gly Ile Gly Ile Leu Thr Val
1               5                   10

<210> SEQ ID NO 119
<211> LENGTH: 9
<212> TYPE: PRT
<213> ORGANISM: Artificial Sequence
<220> FEATURE:
<223> OTHER INFORMATION: Peptide fragment

<400> SEQUENCE: 119

Ser Leu Leu Met Trp Ile Thr Gln Cys
1               5

<210> SEQ ID NO 120
<211> LENGTH: 9
<212> TYPE: PRT
<213> ORGANISM: Artificial Sequence
<220> FEATURE:
<223> OTHER INFORMATION: Peptide fragment

<400> SEQUENCE: 120

Ser Leu Leu Met Trp Ile Thr Gln Val
1               5

<210> SEQ ID NO 121
<211> LENGTH: 9
<212> TYPE: PRT
<213> ORGANISM: Artificial Sequence
<220> FEATURE:
<223> OTHER INFORMATION: Peptide fragment

<400> SEQUENCE: 121

Ile Leu Lys Glu Pro Val His Gly Val
1               5

<210> SEQ ID NO 122
<211> LENGTH: 9
<212> TYPE: PRT
<213> ORGANISM: Artificial Sequence
<220> FEATURE:
<223> OTHER INFORMATION: Peptide fragment

<400> SEQUENCE: 122

Leu Leu Phe Gly Tyr Pro Val Tyr Val
1               5
```

PEPTIDE-HLA COMPLEXES AND METHODS OF PRODUCING SAME

CROSS-REFERENCE TO RELATED APPLICATIONS

This application is a national phase application under 35 U.S.C. § 371 of International Application No. PCT/CA2017/000102 filed 27 Apr. 2017, which claims priority to U.S. Provisional Application No. 62/328,325 filed 27 Apr. 2016. The entire contents of each of the above-referenced disclosures is specifically incorporated by reference herein without disclaimer.

FIELD OF THE INVENTION

The invention relates to the field of human leukocyte antigen (HLA) class I molecules and, more specifically, to methods of producing HLA class I molecules complexed with a peptide.

BACKGROUND OF THE INVENTION

Analysis of antigen-specific T-cells using flow cytometry with peptide-MHC (pMHC) multimers has been established as a standard technique in immunology[1,2]. These reagents enable the tracking and phenotypic analysis of antigen-specific T cells during immune responses associated with infection, autoimmunity, GVHD, and cancer.

αβ T-cell antigen receptors (TCRs) in T cells recognize peptide antigens presented by MHC class I or II molecules on the cell surface[3,4]. The interaction between TCR and pMHC is so weak that monomeric soluble pMHC in general cannot stably associate with the cell surface of T cells bearing a cognate TCR. pMHC multimers in the form of avidin-biotin-based pMHC tetramers were first introduced by Mark Davis' group in 1996 and immediately transformed the analysis of antigen-specific T cells[5]. pMHC multimers have been used in numerous studies and several commercial vendors, such as BD BioSciences™, ProImmune™, Immudex™, and TC Matrix™, sell pMHC multimers in various forms. pMHC multimers can be used in association with a combination of antibodies specific for other cell surface molecules[6]. Accordingly, simultaneous staining of TCR and immunoaccessory molecules allows the classification of antigen-specific T cells into various phenotypically distinct subsets.

Such phenotyping can be used to characterize antigen-specific T cells in terms of their antigen exposure, effector function, and status.

*Escherichia coli* expression is the preferred method for production of MHC class I proteins and can provide large quantities of highly purified protein (tetramer.yerkes.emory.edu/support/protocols). Unlike class II molecules, most class I molecules are unstable as empty without peptide in the groove. Therefore, in virtually all cases, MHC class I molecules are loaded with synthetic peptide of interest, where the class I expression process is coupled to a peptide-loading process to produce complete pMHC complex. There are some known issues with the bacterial system. For some HLA class I genes, such as HLA-B alleles, pHLA production using bacteria is difficult partly because of poor refolding[8,9]. Although glycosylation on class I protein is not necessary for the interaction between pMHC and cognate TCR, lack of sugar moieties on bacterially expressed MHC class I proteins may have a negative impact on their stability. Furthermore, bacterially expressed and in vitro refolded pMHC proteins may not have exactly the same higher structure as those produced in mammalians and refolded in vivo. Although in vitro peptide exchange of generated complete pMHC proteins is possible, it requires multiple complicated steps[10-12]. Therefore, high-throughput production of pMHC proteins is labor-intensive, cumbersome, and not widely available. Finally, it has been shown that the pMHC-TCR affinity required for pMHC multimer binding exceeds that required for T cell activation[13]. The observed difference in affinity threshold means that current pMHC tetramer staining cannot detect all antigen-specific T cells, especially with those with low affinity. Failure to stain all cognate T cells expressing TCR with a broad range of affinity is likely to be a serious issue when pMHC multimers are used to stain self antigen-specific T associated with immune responses in autoimmunity and cancer, which tend to express lower affinity TCRs.

SUMMARY OF INVENTION

According to one aspect, there is provided a method of producing an HLA class I molecule complexed to a pre-selected peptide by providing a mammalian derived HLA class I molecule complexed first to an existing peptide. The HLA class I molecule complexed to the existing peptide is then incubated, in vitro, with the pre-selected peptide at a concentration sufficient to replace the existing peptide, thereby producing the HLA class I molecule complexed to the pre-selected peptide. The HLA class I molecule comprises α1, α2, α3 and β2m domains.

According to a further aspect, there is provided a kit for producing an HLA class I molecule complexed to a pre-selected peptide, comprising a mammalian derived HLA class I molecule complexed to an existing peptide and instructions corresponding to the method described above. In some embodiments, the kit further comprises the pre-selected peptide.

According to a further aspect, there is provided a polypeptide comprising the α1, α2 and α3 domain of an HLA class I molecule, a signal peptide at the N terminus and a 6×His tag joined by a GS linker at the C terminus.

According to a further aspect, there is provided a nucleic acid encoding the polypeptide described above.

According to a further aspect, there is provided a vector comprising the nucleic acid described above.

According to a further aspect, there is provided a mammalian cell transfected with the vector described above.

According to a further aspect, there is provided a compound comprising the polypeptide described above complexed with a β2m domain.

According to a further aspect, there is provided a multimer of at least two of the compounds described above.

In an aspect, the method of screening/selecting in a population of T-cells for antigen specific T-cells that recognize pre-selected peptide antigens, the method comprising: providing a mammalian-derived HLA class I molecule complexed to the pre-selected peptides; screening the population of T-cells for antigen specific T-cells that bind the mammalian-derived HLA class I molecule complexed to the pre-selected peptides.

BRIEF DESCRIPTION OF FIGURES

Embodiments of the invention may best be understood by referring to the following description and accompanying drawings. In the drawings:

FIG. 15 shows A2$^+$ melanoma TILs.

FIG. 28 shows an A2 dimer staining summary.

DETAILED DESCRIPTION

We have developed a novel technology which enables high throughput production of mammalian-derived peptide/HLA class I (pHLA) multimers that can stain low affinity TCRs. One example application of this technology is the generation of personalized pHLA reagents which enables high-throughput measurement of antitumor T cell responses in cancer patients.

According to one aspect, there is provided a method of producing an HLA class I molecule complexed to a pre-selected peptide by providing a mammalian derived HLA class I molecule complexed first to an existing peptide. The HLA class I molecule complexed to the existing peptide is then incubated, in vitro, with the pre-selected peptide at a concentration sufficient to replace the existing peptide, thereby producing the HLA class I molecule complexed to the pre-selected peptide. The HLA class I molecule comprises α1, α2, α3 and β2m domains. In some embodiments, the HLA class I molecule is soluble.

Human Leukocyte Antigen

The HLA system is a gene complex encoding the major histocompatibility complex (MHC) proteins in humans. These cell-surface proteins are responsible for the regulation of the immune system in humans. HLA genes are highly polymorphic, and different classes have different functions. HLA class I genes encoding MHC class I molecules function to display or present peptide fragments of non-self or self proteins from within the cell to cytotoxic T cells.

Figure 1:
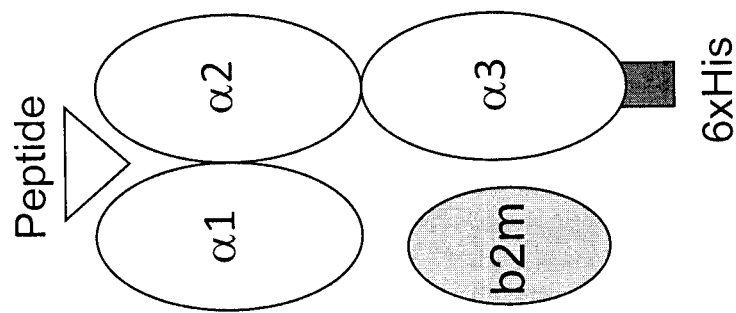
FIG. 1 shows a schematic representation of the general structure of an HLA class I molecule complexed with a peptide.

As used herein, the expression "HLA class I molecule" refers to a protein molecule derived from the expression of wild type or variant HLA class I genes encoding MHC class I molecules. A schematic representation of the general structure of an HLA class I molecule, including its α1, α2, α3 and β2m domains, is depicted in FIG. 1.

The schematic representation also illustrates a peptide complexed to the HLA class I molecule. As used herein, the expression "peptide" refers to peptide fragments that are capable of complexing with the HLA class I molecule and are displayed or presented by the HLA class I molecule. Such peptides have been well described in the art. In general, these particular peptides are about 8-15 amino acids in length but can also vary from between 8-10, 7-11, or 6-12 amino acids in length.

For some HLA class I genes, pHLA production using bacteria is difficult partly because of poor refolding. Furthermore, bacterially expressed and in vitro refolded pMHC proteins may not have exactly the same higher structure as those produced in mammalians and refolded in vivo. As used herein, the expression "mammalian derived" refers to production of molecules utilizing mammalian cell systems which are well known in the art, such as human cell lines (for example, Hela, HEK293, HEK293T and their derivatives), monkey cell lines (for example, CV-1, COS and their derivatives), mouse cell line (for example, NIH3T3 and their derivatives, NS-1 and their derivatives), hamster cell lines (for example, BHK, CHO and their derivatives). In one embodiment, human cell lines are used. In one example, HEK 293T cell lines can be used. The HLA class I molecule complexed to the existing peptide is produced by a mammalian cell transfected with a soluble HLA class I molecule, wherein the β2m domain may be endogenous or exogenous. In preferred embodiments, the β2m domain is exogenous and encoded on a second vector.

In some embodiments, the soluble HLA class I molecule comprises a signal peptide directing secretion of the HLA class I molecule outside of the mammalian cell. In other embodiments, the soluble HLA class I molecule complexed to the existing peptide is provided in the supernatant of a culture of the mammalian cells.

HLA Class I Genes

The HLA class I genes is a family of genes. The HLA class I molecule can be HLA-A, HLA-B, HLA-C, HLA-E, HLA-F, or HLA-G.

As used herein, "HLA-A" refers to a protein molecule derived from the expression of an HLA-A gene. "HLA-B" refers to a protein molecule derived from the expression of an HLA-B gene. "HLA-C" refers to a protein molecule derived from the expression of an HLA-C gene. "HLA-D" refers to a protein molecule derived from the expression of an HLA-D gene. "HLA-E" refers to a protein molecule derived from the expression of an HLA-E gene. "HLA-F" refers to a protein molecule derived from the expression of an HLA-F gene. "HLA-G" refers to a protein molecule derived from the expression of an HLA-G gene. All of the genes HLA-A to HLA-G are part of the HLA class I family of genes.

Amino Acid Sequences of the HLA Class I Molecule

The HLA class I molecule may have a number of amino acid sequence variants.

In some embodiments, the α3 domain of the HLA class I molecule is the mouse Kb α3 domain (designated Kb)). In other embodiments, in the α2 domain of the HLA class I molecule, Gln has been replaced with Glu at position 115 (designated Q115E).

Exemplary HLA class I molecules include but are not limited to the following.

The HLA class I molecule may be HLA-A and comprises the α1, α2 and α3 domains of any of SEQ ID NOs. 6 or 12. In other embodiments, the HLA-A α1, α2 and α3 domains may be wildtype as in SEQ ID NOs. 2 or 14 respectively. Additionally, in yet other embodiments, the α1 and α2 domains are wildtype and the α3 domain of the HLA class I molecule is the mouse Kb α3 domain as in SEQ ID NOs. 4 or 10 respectively. Any combination of the foregoing is also possible.

The HLA class I molecule can be HLA-B and comprises the α1, α2 and α3 domains of any of SEQ ID NOs. 14, 16, 18, 20, or 22. As with exemplary HLA-A molecules, the α1, α2 and α3 domains may be wildtype, or be select variants, such as Kb and Q115E, or any combinations thereof.

The HLA class I molecule can be HLA-C and comprises the α1, α2 and α3 domains of any of SEQ ID NOs. 24, 26, 28, or 30. As with exemplary HLA-A molecules, the α1, α2 and α3 domains may be wildtype, or be select variants, such as Kb and Q115E, or any combinations thereof.

In yet other embodiments, the HLA class I molecule comprises the α1, α2 and α3 domains described herein with a β2m domain.

Multimers

The HLA class I molecule may also be multimerized. According to a further aspect, the method described above further comprises multimerizing the HLA class I molecules, preferably into one of dimers, trimers, tetramers and pentamers.

In some embodiments, the HLA class I molecules are dimerized using an antibody that recognizes a corresponding tag on HLA class I molecule. In further embodiments, the tag is a 6×His tag at the C' end of the α3 domain, preferably connected by a flexible linker, more preferably a GS linker. Other suitable tags for antibody binding are known in the art. Examples of acceptable tags are numerous and include AviTag, Calmodulin-tag, polyglutamate tag, His-tag, Myc-tag, and VSV-tag. Examples of acceptable flexible linkers are numerous; see for example Chen et al, *Adv Drug Deliv Rev.* 2013 Oct. 15; 65(10): 1357-1369.

Kits and Reagents

According to a further aspect, there is provided a kit for producing an HLA class I molecule complexed to a pre-selected peptide, comprising a mammalian derived HLA class I molecule complexed to an existing peptide and instructions corresponding to the method described above. In some embodiments, the kit further comprises the pre-selected peptide.

According to a further aspect, there is provided a polypeptide comprising the α1, α2 and α3 domain of an HLA class I molecule, a signal peptide at the N terminus and a 6×His tag joined by a GS linker at the C terminus. In some embodiments, the polypeptide is SEQ ID NO. 2, 4, 6, 8, 10, 12, 14, 16, 18, 20, 22, 24, 26, 28, or 30.

According to a further aspect, there is provided a nucleic acid encoding the polypeptide described above.

According to a further aspect, there is provided a vector comprising the nucleic acid described above.

According to a further aspect, there is provided a mammalian cell transfected with the vector described above. In some embodiments, the mammalian cell further comprises a second vector encoding β2m.

According to a further aspect, there is provided a compound comprising the polypeptide described above complexed with a β2m domain.

According to a further aspect, there is provided a multimer of at least two of the compounds described above. In some embodiments, the at least two compounds are dimerized by an antibody recognizing the 6×His tag.

The following examples are illustrative of various aspects of the invention, and do not limit the broad aspects of the invention as disclosed herein.

T-Cell Screening and Selection, Including Tumor-Infiltrating Lymphocytes

It is known that HLA class I molecules complexed to a pre-selected peptide can be used to screen/select for T-cells that recognize said peptide antigen through its T-cell receptor. Advantageously, the mammalian derived HLA class I molecules described herein allow the skilled person to swap out an existing (or holder) peptide with a pre-selected peptide of interest. This was not possible with existing bacteria-derived HLA class I molecules. Rather, the existing bacteria-derived HLA class I molecules had to be produced, denatured and then re-folded with the peptide antigen of interest.

The present mammalian-derived HLA class I molecules therefore represent a streamlined and more flexible procedure to easily produce molecules that can present a peptide antigen. For example, the present mammalian-derived HLA class I molecules can be pre-made, the holder peptide being swapped before use. Further, the present mammalian-derived HLA class I molecules are likely more representative of a natural HLA class I molecules as they do not have to be refolded and are glycosylated.

Accordingly, in an aspect, the method of screening/selecting in a population of T-cells for antigen specific T-cells that recognize pre-selected peptide antigens, the method comprising: providing a mammalian-derived HLA class I molecule complexed to the pre-selected peptides; screening the population of T-cells for antigen specific T-cells that bind the mammalian-derived HLA class I molecule complexed to the pre-selected peptides.

In some embodiments, the method further comprises first providing a mammalian-derived HLA class I molecule complexed to a holder peptide; incubating, in vitro, the HLA class I molecule complexed to the holder peptide with the pre-selected peptide, wherein the pre-selected peptide is at a concentration sufficient to replace the existing peptide to produce the HLA class I molecule complexed to the pre-selected peptide.

In some embodiments, the mammalian-derived HLA class I molecule complexed to the pre-selected peptide is prepared using the method of described herein.

In some embodiments, the screening comprises flow cytometry.

In some embodiments, the HLA class I molecule complexed to the holder peptide comprises any one of SEQ ID NO. 2, 4, 6, 8, 10, 12, 14, 16, 18, 20, 22, 24, 26, 28, or 30, preferably with a β2m domain.

In some embodiments, the HLA class I molecule complexed to the holder peptide comprises the polypeptide described herein, preferably with a β2m domain.

In some embodiments, the method may be used to screen/select for T-Cell populations associated with a cancer. Cancer may include adrenal cancer, anal cancer, bile duct cancer, bladder cancer, bone cancer, brain/cns tumors, breast cancer, castleman disease, cervical cancer, colon/rectum cancer, endometrial cancer, esophagus cancer, ewing family of tumors, eye cancer, gallbladder cancer, gastrointestinal carcinoid tumors, gastrointestinal stromal tumor (gist), gestational trophoblastic disease, hodgkin disease, kaposi sarcoma, kidney cancer, laryngeal and hypopharyngeal cancer, leukemia (acute lymphocytic, acute myeloid, chronic lymphocytic, chronic myeloid, chronic myelomonocytic), liver cancer, lung cancer (non-small cell, small cell, lung carcinoid tumor), lymphoma, lymphoma of the skin, malignant mesothelioma, multiple myeloma, myelodysplastic syndrome, nasal cavity and paranasal sinus cancer, nasopharyngeal cancer, neuroblastoma, non-hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma—adult soft tissue cancer, skin cancer (basal and squamous cell, melanoma, merkel cell), small intestine cancer, stomach cancer, testicular cancer, thymus cancer, thyroid cancer, uterine sarcoma, vaginal cancer, vulvar cancer, waldenstrom macroglobulinemia, or wilms tumor.

In some embodiments, the antigen specific T-cells that recognize pre-selected peptide antigens are tumor-infiltrating lymphocytes.

In some embodiments, the pre-selected peptide antigens are associated with cancer.

EXAMPLES

Materials and Methods

Peptides

Synthetic peptides were purchased from ProImmune, Genway Biotech, and GenScript. Peptides used were A2-restricted heteroclitic MART1$_{26\text{-}35}$ (ELAGIGILTV), heteroclitic NY-ESO-1$_{157\text{-}165}$ (SLLMWITQV), A24-restricted heteroclitic WT1$_{235\text{-}243}$ (CYTWNQMNL), B35-restricted wild-type EBNA-1$_{407\text{-}417}$ (HPVGEADYFEY) peptides, B44-restricted wild-type EBNA-6$_{281\text{-}290}$ (EENLLDFVRF), C7-restricted wild-type MAGE-A1$_{289\text{-}297}$ (RVRFFFPSL), and C7-restricted wild-type MAGE-A12$_{170\text{-}178}$ (VRIGHLYIL) peptides. A2 peptides used to stain TILs are listed in Table 1 below.

TABLE 1

A2 peptides tested

| | Name | Sequence | SEQ ID NO. |
|---|---|---|---|
| 1 | WT1 (37-) | VLDFAPPGA | 35 |
| 2 | WT1 (126-) | RMFPNAPYL | 36 |
| 3 | WT1 (87-) | SLGEQQYSV | 37 |
| 4 | WT1 (235-) | CMTWNQMNL | 38 |
| 5 | MIA (54-) | YMAPDCRFL | 39 |
| 6 | MIA (99-) | RLGYFPSSI | 40 |
| 7 | ALX1 (142-) | LQLEELEKV | 41 |
| 8 | ALX1 (170-) | ELTEARVQV | 42 |
| 9 | GAPDHS (358-) | FLGDTHSSI | 43 |
| 10 | GAPDH2 (345-) | ILAYTEDEV | 44 |
| 11 | S100B (44-) | FLEEIKEQEV | 45 |
| 12 | S100B (74-) | FMAFVAMVT | 46 |
| 13 | ABCB5 (1078-) | LLDEATSAL | 47 |
| 14 | ABCB5 (700-) | VLNGTVHPV | 48 |
| 15 | EXTL1 (249-) | VLLSPRWEL | 49 |
| 16 | EXTL1 (13-) | FLWDAYFSS | 50 |
| 17 | EXTL1 (330-) | WLALSASWL | 51 |
| 18 | CPN1 (379-) | LLLPGIYTV | 52 |
| 19 | CPN1 (249-) | KLFQKLAKV | 53 |
| 20 | CPN1 (297-) | YLHTNCFEI | 54 |
| 21 | TSPAN10 (81-) | FLSNFPFSL | 55 |
| 22 | TSPAN10 (94-) | ALAIGLWGL | 56 |
| 23 | TSPAN10 (142-) | ALCENTCLL | 57 |
| 24 | GJB1 (155-) | LLYPGYAMV | 58 |
| 25 | GJB1 (5-) | GLYTLLSGV | 59 |
| 26 | GJB1 (147-) | AVFMYVFYL | 60 |
| 27 | MITF (378-) | LMDDTLSPV | 61 |
| 28 | MITF (142-) | LQMANTLPV | 62 |
| 29 | MITF (392-) | LLSSVSPGA | 63 |
| 30 | DUSP4 (362-) | SQFVFSFPV | 64 |
| 31 | DUSP4 (326-) | QLLQFESQV | 65 |
| 32 | DUSP4 (53-) | FLAHSAGYI | 66 |
| 33 | cyclin-A1 (227-) | FLDRFLSCM | 67 |
| 34 | cyclin-A1 (341-) | SLIAAAAFCLA | 68 |
| 35 | HERV-K-MEL (1-) | MLAVISCAV | 69 |
| 36 | LAGE-1 (1-) | MLMAQEALAFL | 70 |
| 37 | MAGE-A1 (278-) | KVLEYVIKV | 71 |

TABLE 1-continued

A2 peptides tested

| | Name | Sequence | SEQ ID NO. |
|---|---|---|---|
| 38 | MAGE-A2 (157-) | YLQLVFGIEV | 72 |
| 39 | MAGE-A3 (271-) | FLWGPRALV | 73 |
| 40 | MAGE-A3 (112-) | KVAELVHFL | 74 |
| 41 | MAGE-A4 (230-) | GVYDGREHTV | 75 |
| 42 | MAGE-A9 (223-) | ALSVMGVYV | 76 |
| 43 | MAGE-A10 (254-) | GLYDGMEHL | 77 |
| 44 | MAGE-A12 (271-) | FLWGPRALV | 78 |
| 45 | MAGE-C1 (959-) | ILFGISLREV | 79 |
| 46 | MAGE-C1 (1083-) | KVVEFLAML | 80 |
| 47 | LAGE-2 (1-) | MLMAQEALAFL | 81 |
| 48 | SSX-2 (41-) | KASEKIFYV | 82 |
| 49 | XAGE-1b (21-) | RQKKIRIQL | 83 |
| 50 | CEA (691-) | IMIGVLVGV | 84 |
| 51 | gp100 (154-) | KTWGQYWQV | 85 |
| 52 | gp100 (177-) | AMLGTHTMEV | 86 |
| 53 | gp100 (178-) | MLGTHTMEV | 87 |
| 54 | gp100 (209-) | ITDQVPFSV | 88 |
| 55 | gp100 (280-) | YLEPGPVTA | 89 |
| 56 | gp100 (457-) | LLDGTATLRL | 90 |
| 57 | gp100 (476-) | VLYRYGSFSV | 91 |
| 58 | gp100 (570-) | SLADTNSLAV | 92 |
| 59 | gp100 (619-) | RLMKQDFSV | 93 |
| 60 | gp100 (639-) | RLPRIFCSC | 94 |
| 61 | NY-BR-1 (904-) | SLSKILDTV | 95 |
| 62 | TRP-2 (180-) | SVYDFFVWL | 96 |
| 63 | TRP-2 (360-) | TLDSQVMSL | 97 |
| 64 | tyrosinase (1-) | MLLAVLYCL | 98 |
| 65 | tyrosinase (8-) | CLLWSFQTSA | 99 |
| 66 | tyrosinase (369-) | YMDGTMSQV | 100 |
| 67 | CD274 (15-) | LLNAFTVTV | 101 |
| 68 | CPSF (250-) | KVHPVIWSL | 102 |
| 69 | CPSF (1360-) | LMLQNALTTM | 103 |
| 70 | cyclin D1 (101-) | LLGATCMFV | 104 |
| 71 | IDO1 (199-) | ALLEIASCL | 105 |
| 72 | mdm-2 (53-) | VLFYLGQY | 106 |
| 73 | p53 (264-) | LLGRNSFEV | 107 |
| 74 | p53 (65-) | RMPEAAPPV | 108 |
| 75 | PRAME (100-) | VLDGLDVLL | 109 |
| 76 | PRAME (142-) | SLYSFPEPEA | 110 |
| 77 | PRAME (300-) | ALYVDSLFFL | 111 |
| 78 | PRAME (425-) | SLLQHLIGL | 112 |
| 79 | SOX10 (332-) | AWISKPPGV | 113 |
| 80 | SOX10 (331-) | SAWISKPPGV | 114 |
| 81 | survivin (95-) | ELTLGEFLKL | 115 |
| 82 | Telomerase (865-) | RLVDDFLLV | 116 |
| 83 | Wild type MART1 (27-35) | AAGIGILTV | 117 |
| 84 | Heteroclitic MART1 (26-35) | ELAGIGILTV | 118 |
| 85 | Wild type NY-ESO-1 (157-165) | SLLMWITQC | 119 |
| 86 | Heteroclitic NY-ESO-1 (157-165) | SLLMWITQV | 120 |
| 87 | HIV pol (476-484) | ILKEPVHGV | 121 |
| 88 | HTLV-1 tax (11-19) | LLFGYPVYV | 122 |
| 89 | No peptide exchange | | |

Cells and cDNAs

HEK293T cells were obtained from American Type Culture Collection. TILs isolated from an HLA-A2+ patient with metastatic melanoma were grown in vitro as reported previously[14]. Appropriate informed consent and institutional review board approval were obtained. All clonotypic TCR genes were reconstituted in Jurkat 76/CD8 cells or primary T cells as previously described. cDNAs were fused with puromycin resistance gene via internal ribosome entry site[15,16]. Transduced cells were isolated by puromycin selection. All cDNAs were cloned into pMX vector and transduced using 293GPG cell-based retrovirus system[16-19].

Flow Cytometry Analysis mAbs recognizing the following surface antigens were used: β2m (551337, BD BioSciences), His (ab72467, Abcam). Mouse isotype controls were from BD BioSciences. Surface molecular staining was carried out as described elsewhere[16,20].

Immunoblotting

For immunoblotting, cells were extracted in ice-cold Nonidet P-40 (NP-40) extraction buffer (20 mM Tris-HCl, pH 7.5, containing 1 mM EDTA, 150 mM NaCl, 2.5 mM sodium pyrophosphate, 1 mM β-glycerophosphate, 1% NP-40, 1 mM PMSF, and 1 μg/ml Aprotinin). Cell extracts were centrifuged at 10,000 g for 10 min at 4° C. and separated by Tris-Glycine SDS-PAGE followed by electrophoretic transfer to Immobilon-P membrane (Millipore). After blocking with 5% nonfat dry milk in Tris-buffered saline containing 0.1% Tween 20, the membranes were incubated with the indicated mouse anti-His mAb (sc-53073, Santa Cruz Biotechnology) at 4° C. overnight, washed and incubated with HRP-conjugated goat anti-mouse IgG (H+L) secondary antibody (Promega) at room temperature for 1 hr. The signal was detected by enhanced chemiluminescence (GE Healthcare).

Results and Discussion

Structure of Soluble Monomeric Peptide/HLA Class I (pHLA) Complexes

HLA class I molecules are heterodimers consisting of two polypeptide chains, α and β2-microglobulin (β2m), which are non-covalently linked. While the α chain is highly polymorphic, the β2m subunit is monomorphic. The HLA class I α1 and α2 domains constitute a groove for peptides of 8-10 amino acids in length. The α3 domain, which contains a transmembrane domain, binds β2m. While TCR on the surface of cytotoxic T cells recognizes the peptides presented by the HLA class I α1 and α2 domains to check antigenicity, the CD8 co-receptor binds the α2 and α3 domains to stabilize the interaction between the TCR and pHLA. Therefore, enhancement of the CD8 and HLA class I interaction leads to the improvement in the strength of the interaction between pHLA and cognate TCR.

It has been demonstrated that replacement of HLA class I α3 domain with mouse Kb α3 domain, named hereafter class I-Kb, enhances the interaction between the class I and CD8 by 10 times. Substitution of the Gln (Q) residue at position 115 of the α2 domain with a Glu (E) residue, named hereafter class $I^{Q115E}$, further improves the interaction by 1.5 times[21,22]. By fusing the extracellular domain of wild-type (wt) HLA class I with a Gly-Ser (GS) flexible linker followed by a 6×His tag, we have generated soluble class I-wt. Soluble class I-Kb and class $I^{Q115E}$-$K^b$ were similarly produced.

Nucleotide and amino acid sequences of soluble class I-wt, class I-$K^b$, and class $I^{Q115E}$-$K^b$ genes used in this study are listed below.

Production of Soluble Monomeric pHLA Complexes Using Mammalian Cells

HEK293T cells were initially transfected with β2m gene and subsequently with soluble HLA class I-$K^b$ or HLA class $I^{Q116E}$-$K^b$ gene using the pMX vector and 293GPG cell-based retrovirus system[16-19].

Enhanced β2m Expression by Gene Transduction

Flow cytometry analysis following β2m-specific mAb staining demonstrated enhanced β2m expression in HEK293T cells stably transfected with β2m gene along with a soluble form of HLA-A2-$K^b$ or A2$^{Q116E}$-$K^b$. HLA-A*02:01 (A2) gene, which is one of the most frequent HLA class I alleles, was used as a representative HLA class I gene. The same strategy was applied to generate HEK293T-derived cell lines stably expressing a soluble form of other class I genes.

Cellular Expression of Soluble Monomeric Peptide/HLA (pHLA) in HEK293T Transfectants Total cell lysates of HEK293T cells stably expressing soluble HLA-A2-$K^b$ or A2$^{Q116E}$-$K^b$ gene in conjunction with or without β2m gene were blotted with anti-His mAb as reported previously[23-25]. Cellular expression of soluble HLA-A2-$K^b$ and A2$^{Q116E}$-$K^b$ was demonstrated at the protein level.

Secretion of Soluble Monomeric pHLA Complexes into the Supernatant.

Supernatant of HEK293T cells transfected with soluble HLA-A2-$K^b$ or A2$^{Q116E}$-$K^b$ gene along with or without β2m gene was harvested and blotted with His-specific mAb. Indicated amounts of bacterially-expressed and 6×His-tagged HLA-A2/heteroclitic MART1$_{26-35}$ monomer (NIH tetramer core facility) were loaded as controls. Ten μl of each supernatant was loaded per lane without any concentration. Secretion of monomeric HLA-A2-$K^b$ and A2$^{Q116E}$-$K^b$ into the medium was confirmed.

Monomeric pHLA Complexes were Secreted Only when β2m was Overexpressed.

When HEK293T cells were transduced with soluble HLA-A2-$K^b$ or A2$^{Q116E}$-$K^b$ gene alone without β2m gene, secretion of soluble A2-$K^b$ and A2$^{Q116E}$-$K^b$ into the medium was not detectable. This suggests that the endogenous β2m expression level was not sufficient to enable the secretion of ectopically expressed soluble A2-$K^b$ and A2$^{Q115E}$-$K^b$.

Production of Monomeric pHLA Loaded with Peptide of Interest by In Vitro Peptide Exchange.

Figure 2:
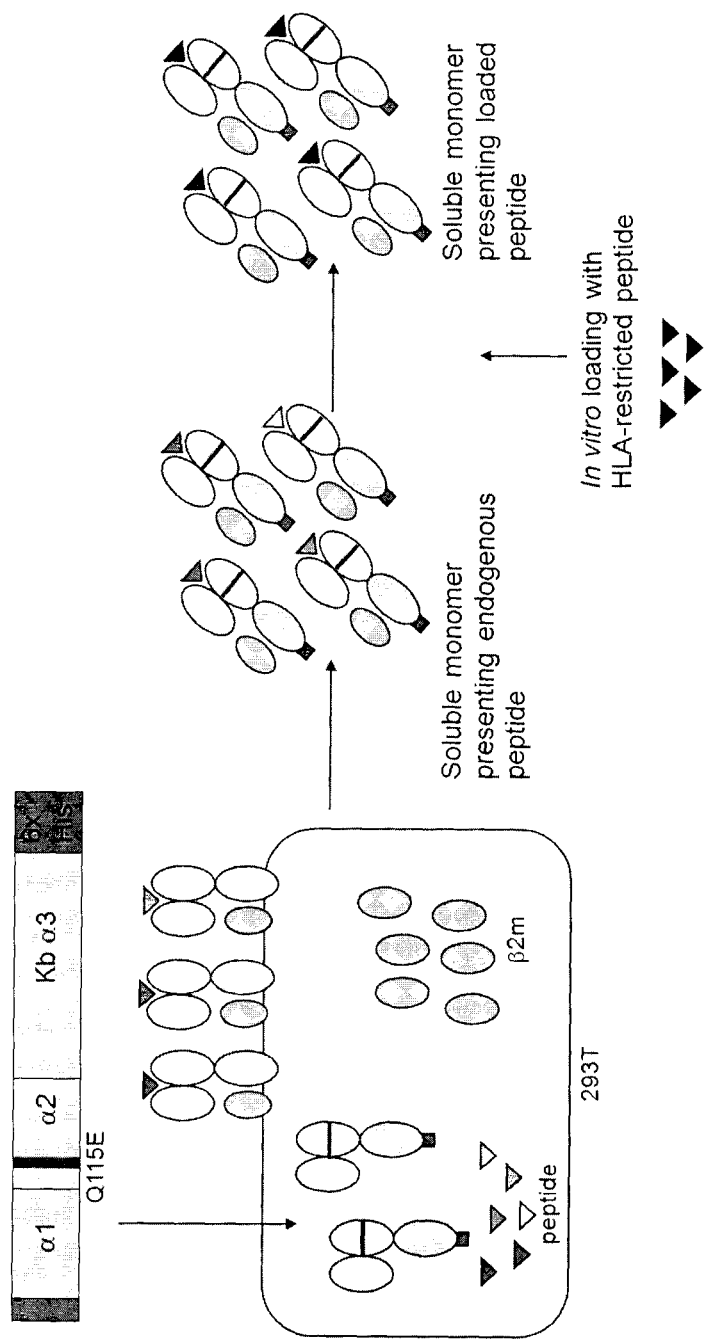
FIG. 2 shows production of monomeric pHLA presenting peptide of interest by in vitro peptide exchange.

Soluble HLA-A2-$K^b$ and A2$^{Q115E}$-$K^b$-containing supernatant produced by the HEK293T transfectants were simply mixed with the indicated concentration of A2-restricted peptide of interest at room temperature for in vitro peptide exchange (see FIG. 2).

Dimerization of Monomeric pHLA Complexes.

Soluble HLA classI$^{Q115E}$-$K^b$ monomer in the HEK293T conditioned medium was dimerized using anti-His mAb conjugated with fluorochrome such as phycoerythrin (PE) at at 2:1 molar ratio. Note that the soluble proteins were fused with a 6×His tag at the C-terminus.

Overall Protocol for Production of Dimeric pHLA Complexes to Stain Antigen-Specific T Cells.

Figure 3:
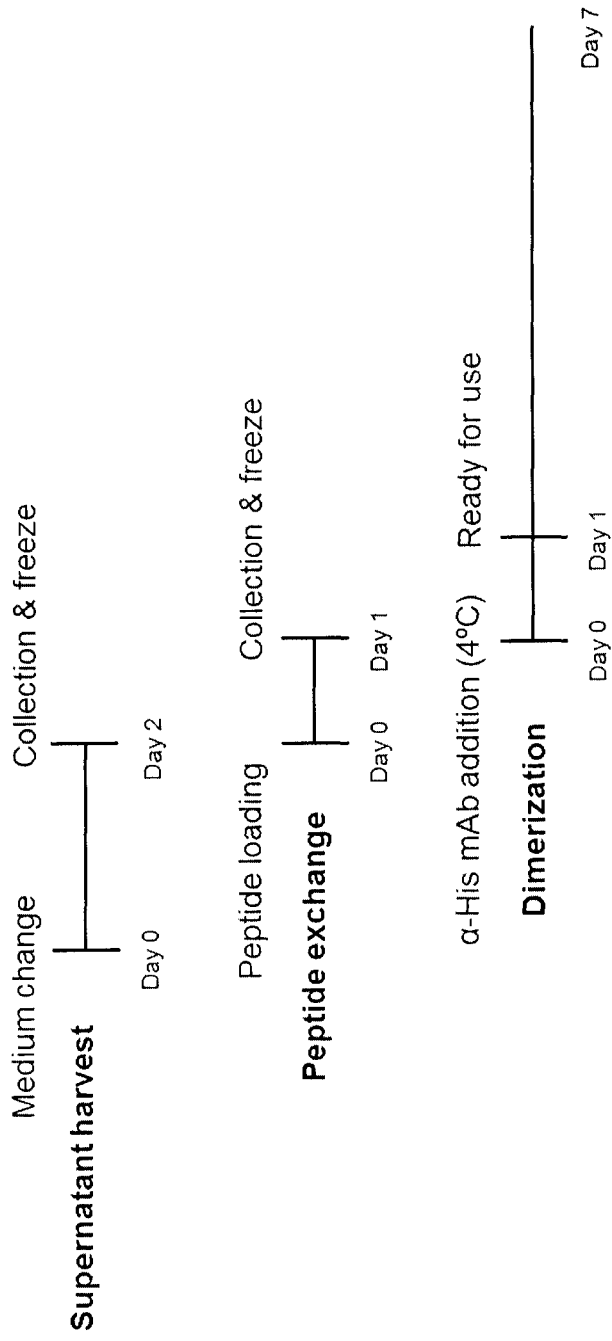
FIG. 3 shows a timeline chart of harvest, peptide loading, and dimerization of pHLA to stain antigen-specific T cells.

Stable HEK293T cell lines ectopically expressing soluble monomeric class $I^{Q115E}$-$K^b$ and β2m were established as described above. The stable cell lines were grown until confluent and medium was changed. After 48 hrs, the conditioned medium was harvested and immediately used or frozen until use. The supernatant was loaded with class I-restricted peptide of interest for 24 hrs at 37° C. for in vitro peptide exchange. The soluble monomeric class $I^{Q115E}$-$K^b$ loaded with the peptide was dimerized using fluorochrome-conjugated anti-His mAb for 24 hrs at 4° C. (see FIG. 3).

Peptide Exchange Occurs in the Supernatant by Simple Mixing.

Figure 4:
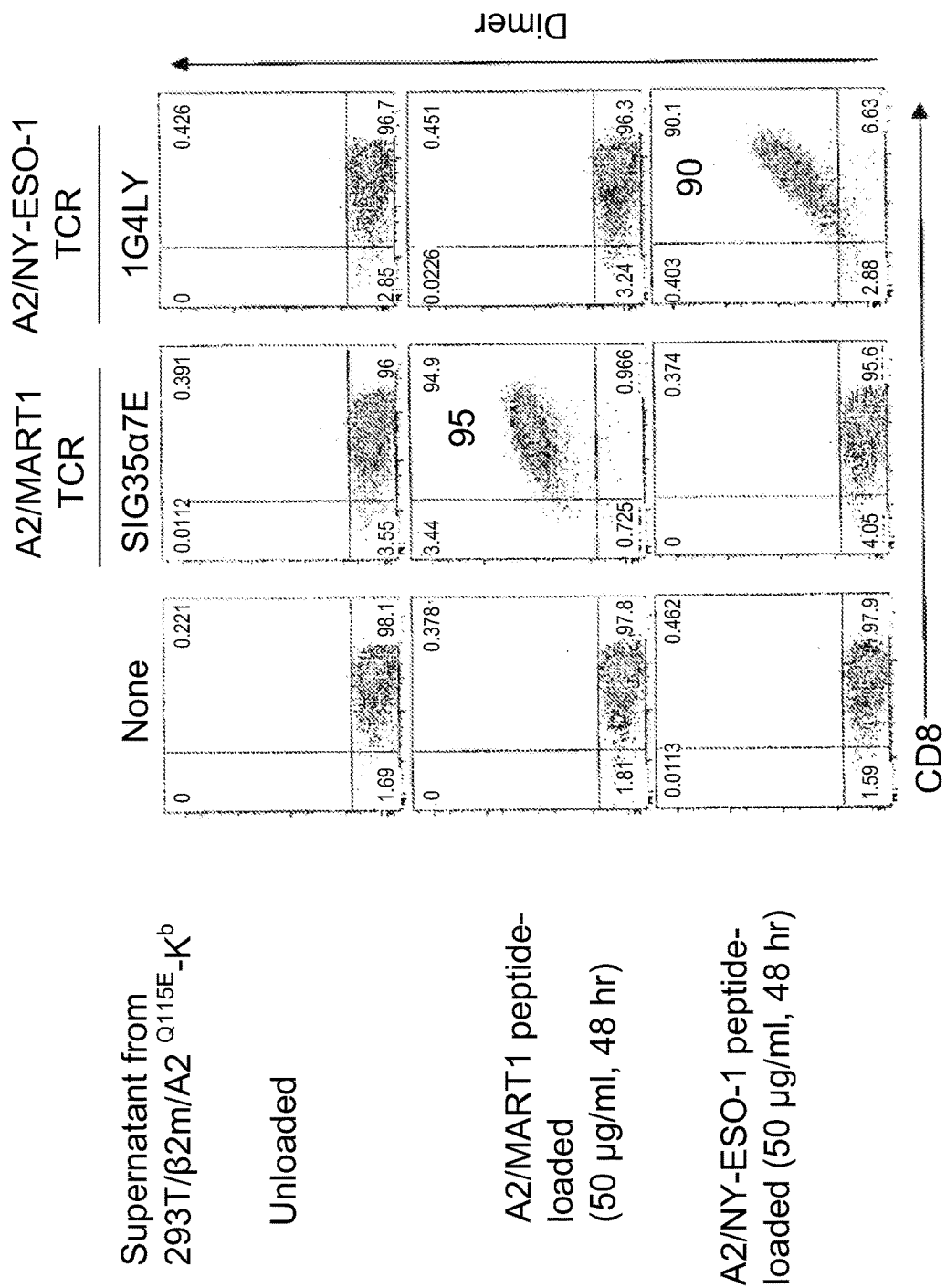
FIG. 4 shows staining data showing peptide exchange occurring in a supernatant sample.

Soluble A2$^{Q115E}$-$K^b$ monomer was loaded with A2/MART1$_{26-35}$ (ELAGIGILTV) or A2/NY-ESO-1$_{157-165}$ (SLLMWITQV) peptide by simple mixing, dimerized with PE-conjugated anti-His mAb, and used to stain human Jurkat 76/CD8 T cells expressing clonotypic cognate TCR (see FIG. 4). Jurkat 76/CD8 cells, lacking the endogenous TCR expression, stably express CD8α/β genes[26,27].

Soluble Monomeric A2$^{Q115E}$-$K^b$ Stains High Avidity Antigen-Specific T Cells.

Figure 5:
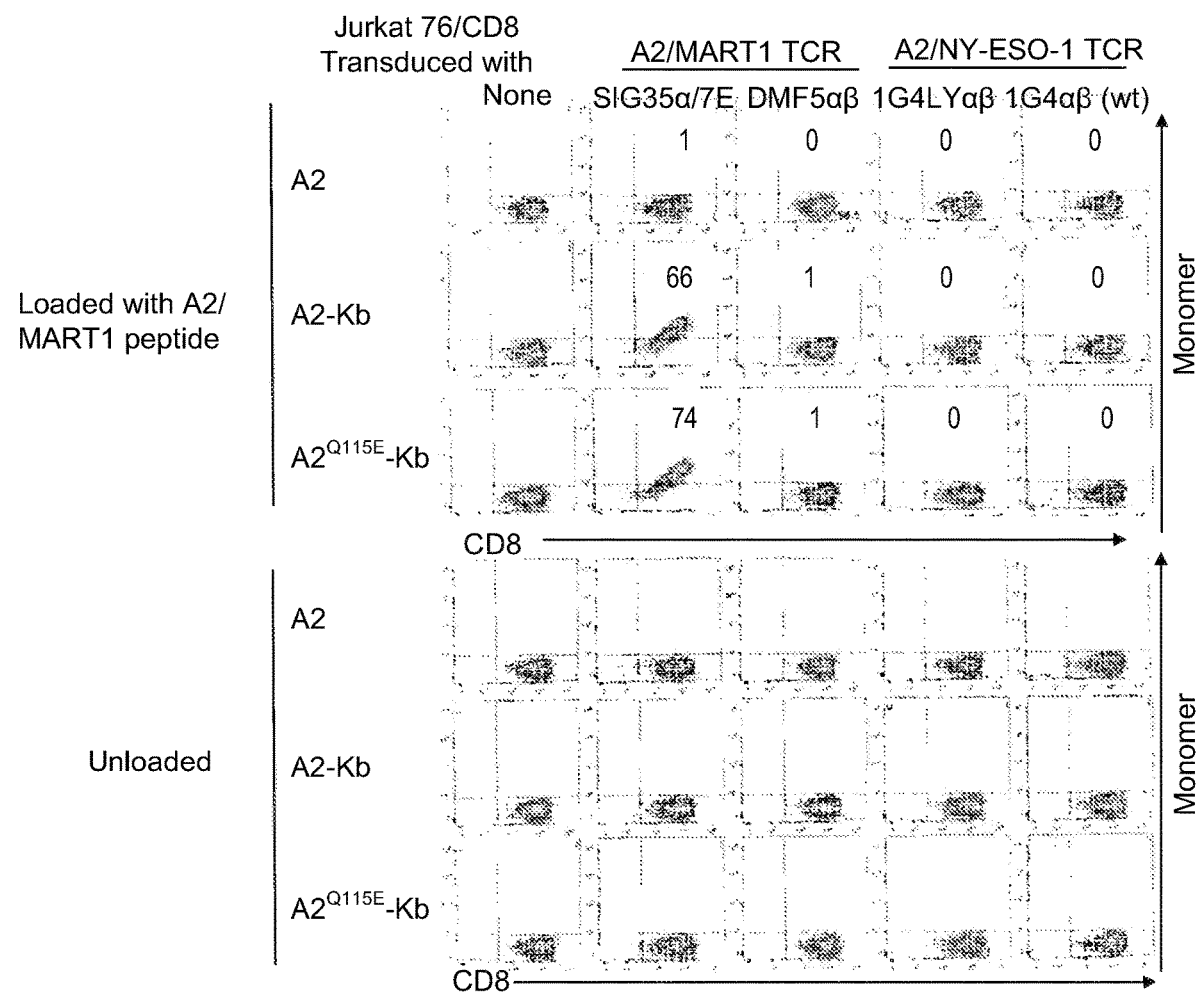
FIG. 5 shows staining data showing A2/MART1 monomer staining high avidity A2/MART1 T cells but not A2/NY-ESO-1 T cells.
Figure 6:
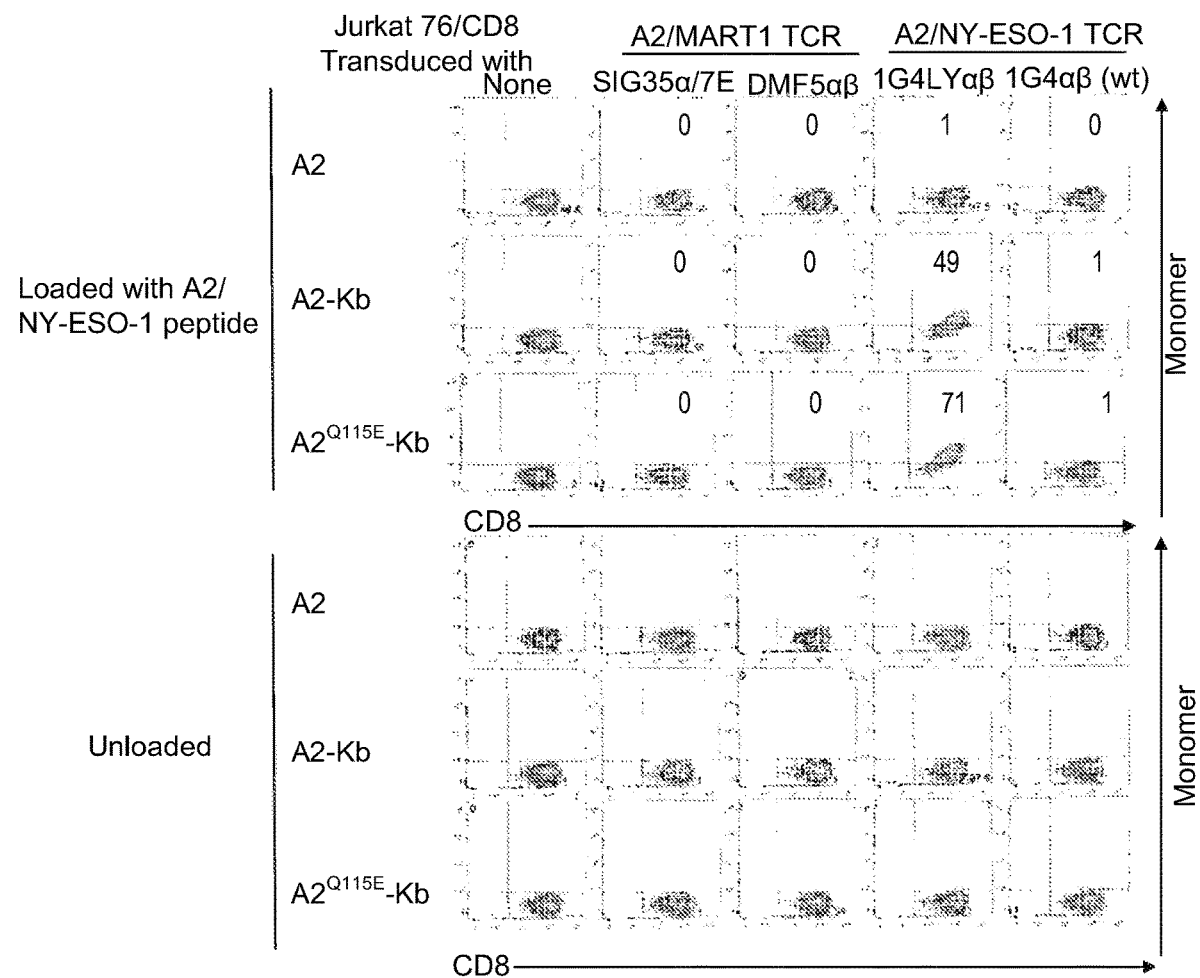
FIG. 6 shows staining data showing A2/NY-ESO-1 monomer staining high avidity A2/NY-ESO-1 T cells but not A2/MART1 T cells.

Soluble A2$^{Q115E}$-$K^b$ monomer was loaded with A2/MART1$_{26-35}$ or A2/NY-ESO-1$_{157-165}$ peptide by simple mixing and, without dimerization, directly used to stain Jurkat 76/CD8 T cells expressing clonotypic cognate TCR. Jurkat 76/CD8 cells expressing high but not low affinity TCRs were stained by monomeric soluble A2$^{Q115E}$-$K^b$ loaded with cognate peptide (see FIGS. 5 and 6)[27].

Soluble Dimeric A2$^{Q115E}$-Kb Stains Both High and Low Avidity Antigen-Specific T Cells.

Figure 7:
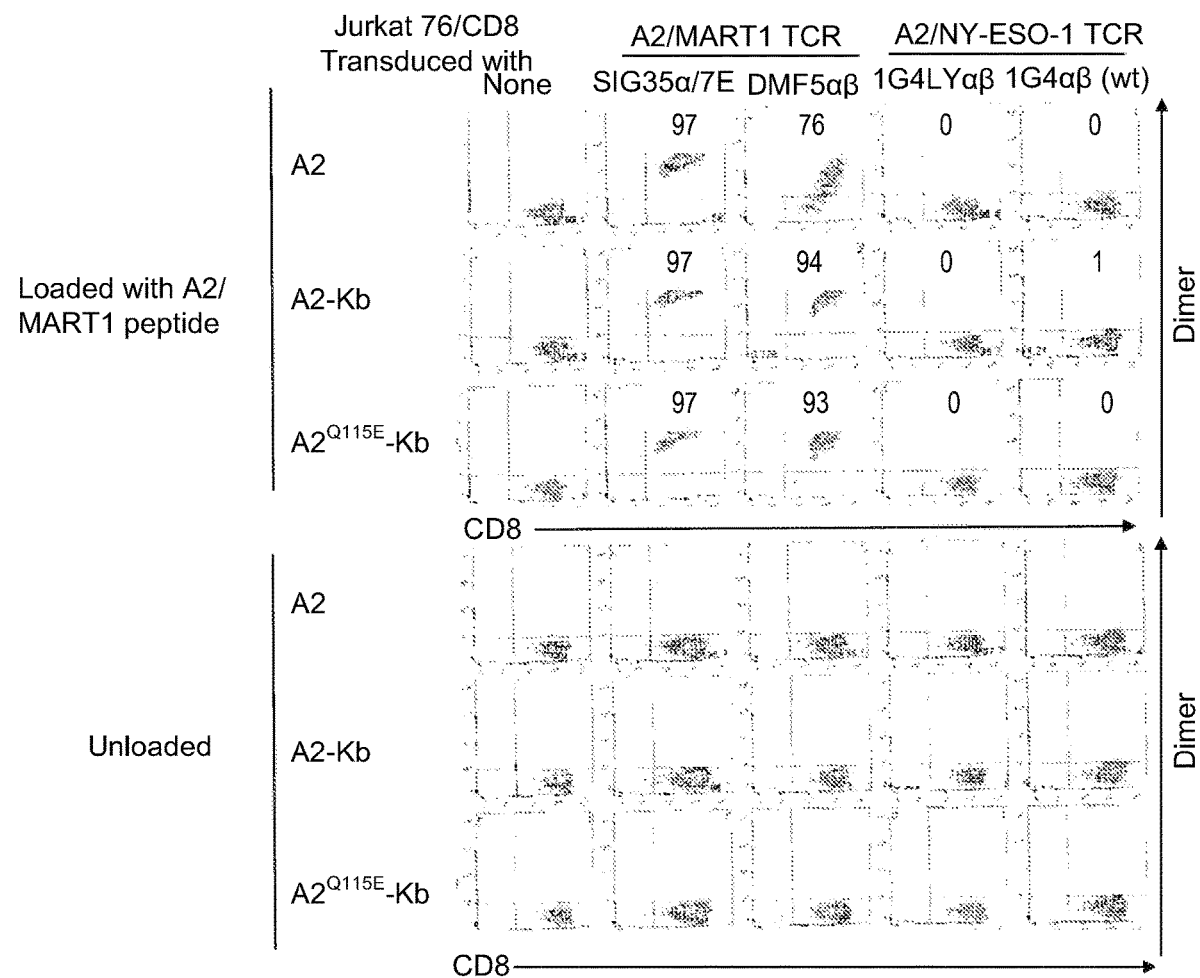
FIG. 7 shows staining data showing A2/MART1 dimer staining A2/MART1 T cells but not A2/NY-ESO-1 T cells.
Figure 8:
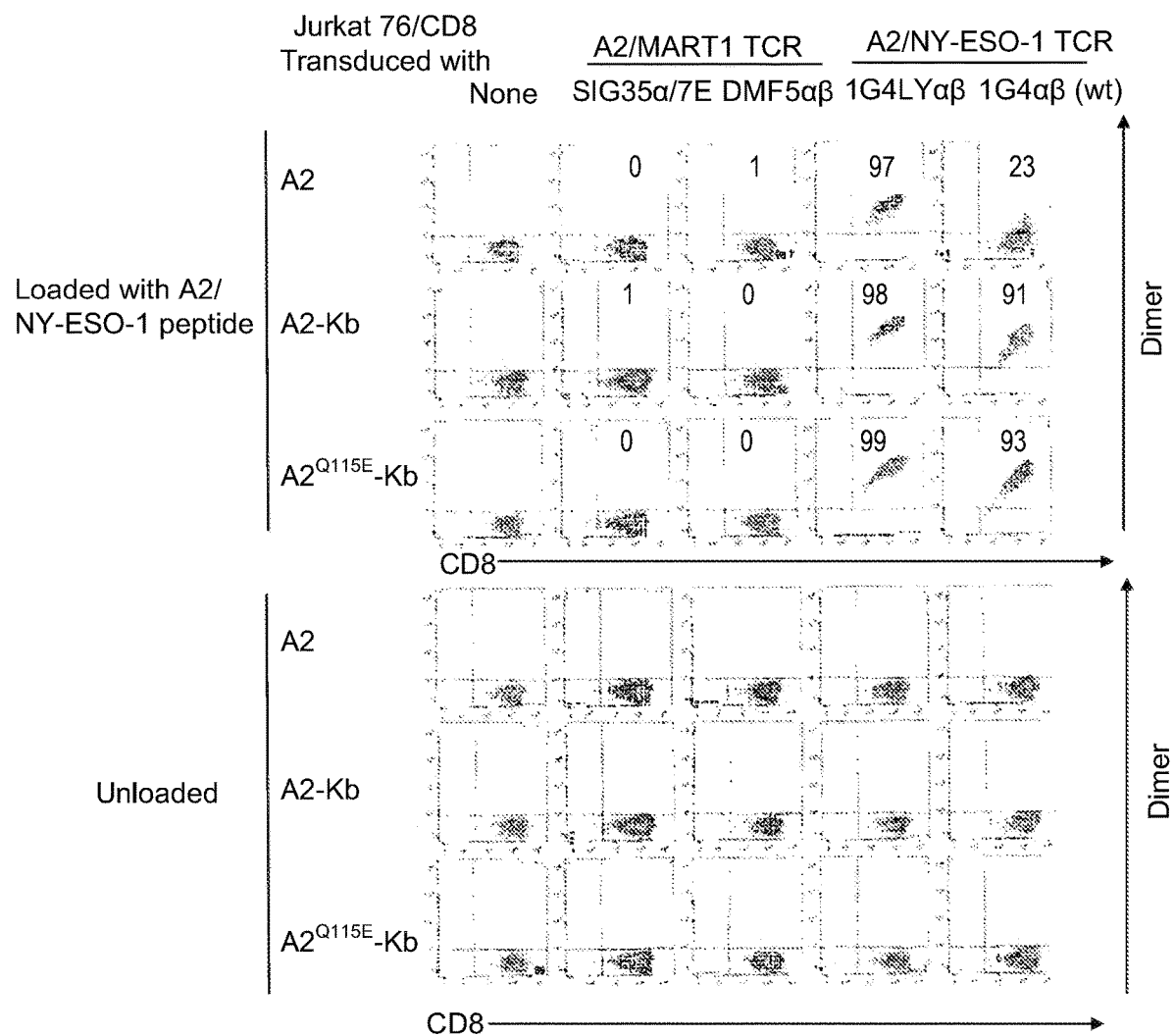
FIG. 8 shows staining data showing A2/NY-ESO-1 dimer staining A2/NY-ESO-1 T cells but not A2/MART1 T cells.

Soluble monomeric A2$^{Q115E}$-$K^b$ containing supernatant was loaded with A2/MART1$_{26-35}$ or A2/NY-ESO-1$_{157-165}$ peptide by simple mixing, dimerized with PE-conjugated anti-His mAb, and utilized to stain Jurkat 76/CD8 T cells expressing clonotypic cognate TCR (see FIGS. 7 and 8). Both high and low affinity TCRs expressed in Jurkat 76/CD8 cells were stained by soluble dimeric A2$^{Q115E}$-$K^b$ loaded with respective peptide[27].

Soluble Dimeric Class $I^{Q115E-Kb}$ Stains Low Affinity TCRs Better than Pentamer (ProImmune) or Tetramer (NIH)

Figure 9:
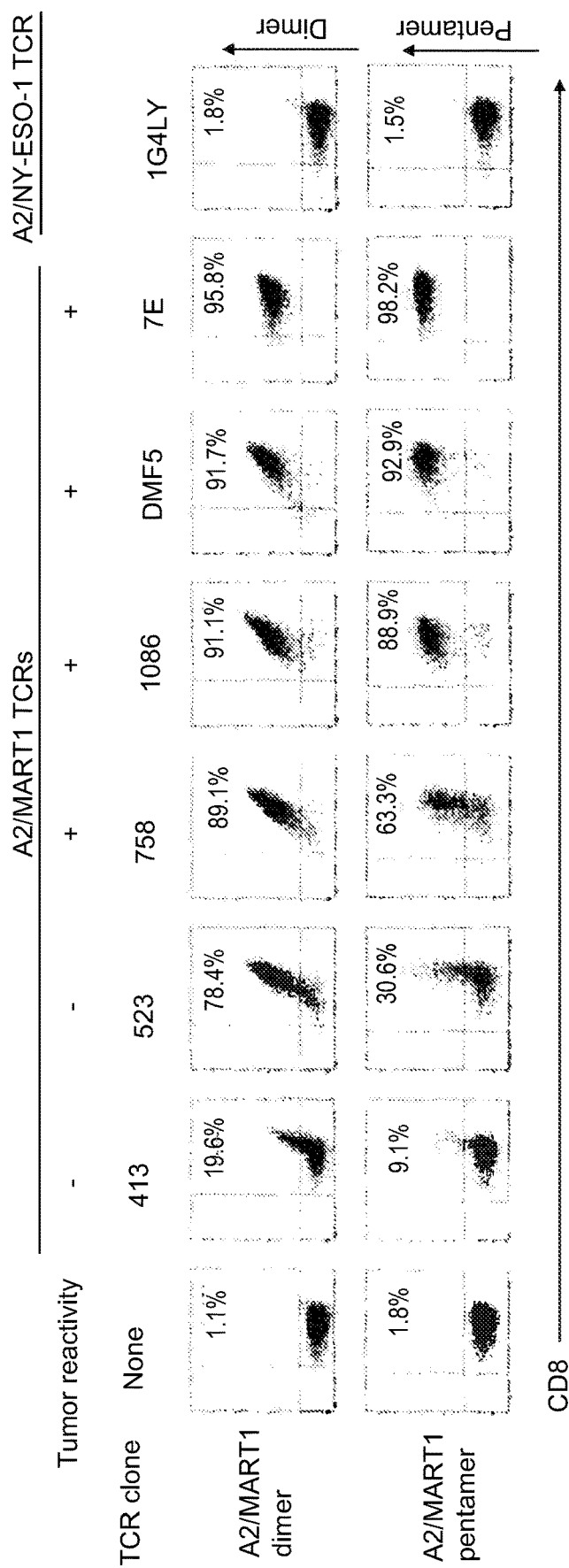
FIG. 9 shows staining data showing a dimer embodiment staining low affinity A2/MART1 TCRs better than a known Pentamer.
Figure 10:
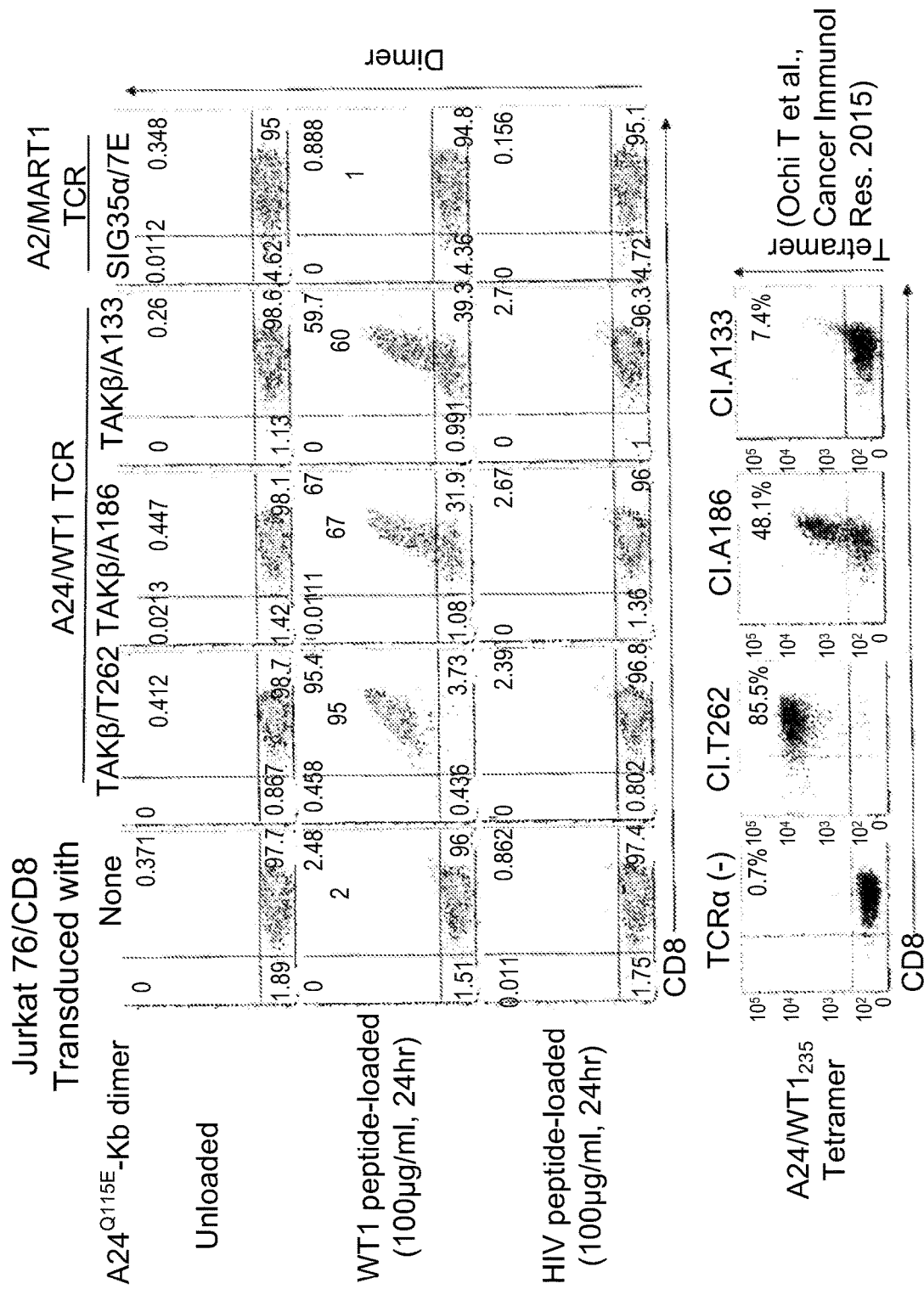
FIG. 10 shows staining data showing A24Q115E-Kb dimer staining low affinity A24/WT1 TCRs better than a prior art A24/WT1 tetramer.

PE-conjugated soluble dimeric A2$^{Q115E}$-$K^b$ and A24$^{Q115E}$-$K^b$ were loaded with A2/MART1$_{26-35}$ and A24/WT1$_{235-243}$ (CYTWNQMNL) peptides, respectively. The loaded dimers were employed to stain Jurkat 76/CD8 T cells expressing clonotypic cognate TCRs with various affinities[26,27]. Our dimer stained low affinity TCRs better than Pentamer (ProImmune) and NIH's tetramer (see FIGS. 9 and 10). Pentamer was used according to the protocol provided by the vendor (proimmune.com/ecommerce/page.php?page=protocols). Tetramer staining was performed according to the standard protocol as published elsewhere[26,27].

Soluble Dimeric HLA-$B^{Q115E}$-$K^b$ Works as Well.

Figure 11:
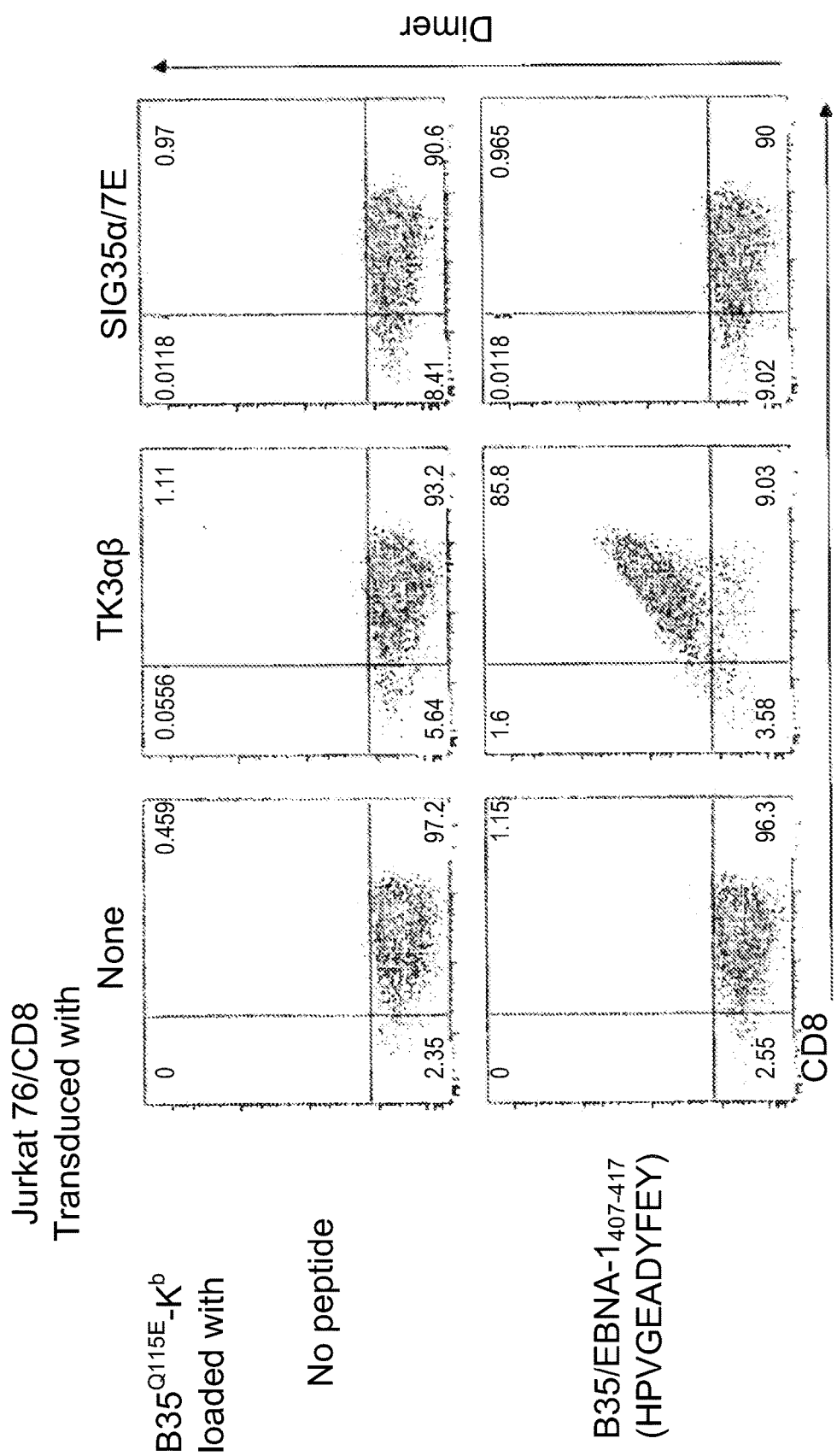
FIG. 11 shows staining data showing B35Q115E-Kb dimer stains B*35:01/EBNA-1$_{407-417}$ TCR (Clone TK3).
Figure 12:
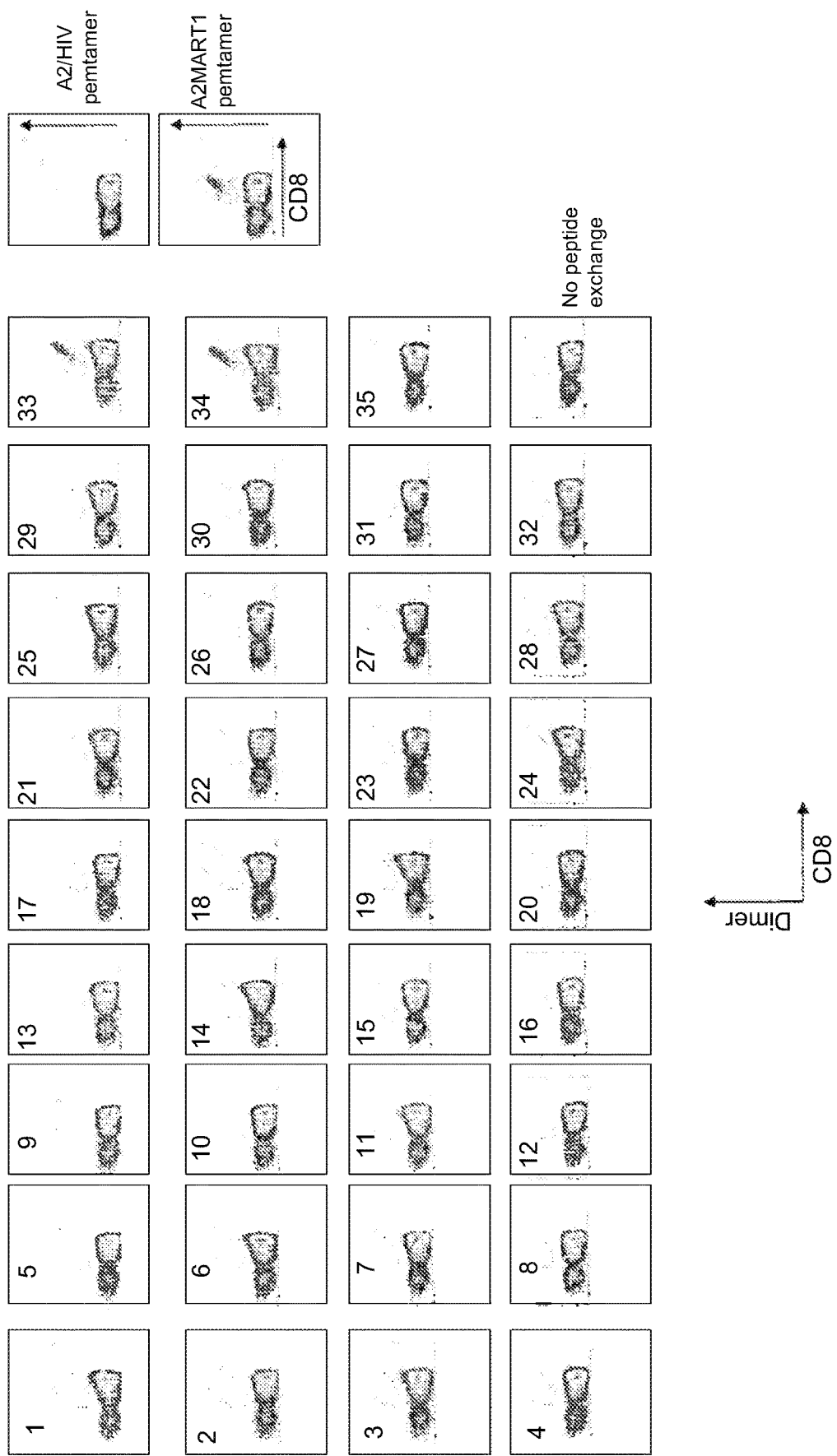
FIG. 12 shows staining data showing high throughput A2 dimer staining of TILs.

Soluble monomeric HLA-$B35^{Q115E}$-$K^b$ was loaded with B35/EBNA-$1_{407\text{-}417}$ (HPVGEADYFEY) peptide, dimerized with PE-conjugated anti-His mAb, and used to stain Jurkat 76/CD8 T cells expressing clonotypic cognate TCR (see FIG. 11).

Figure 13:
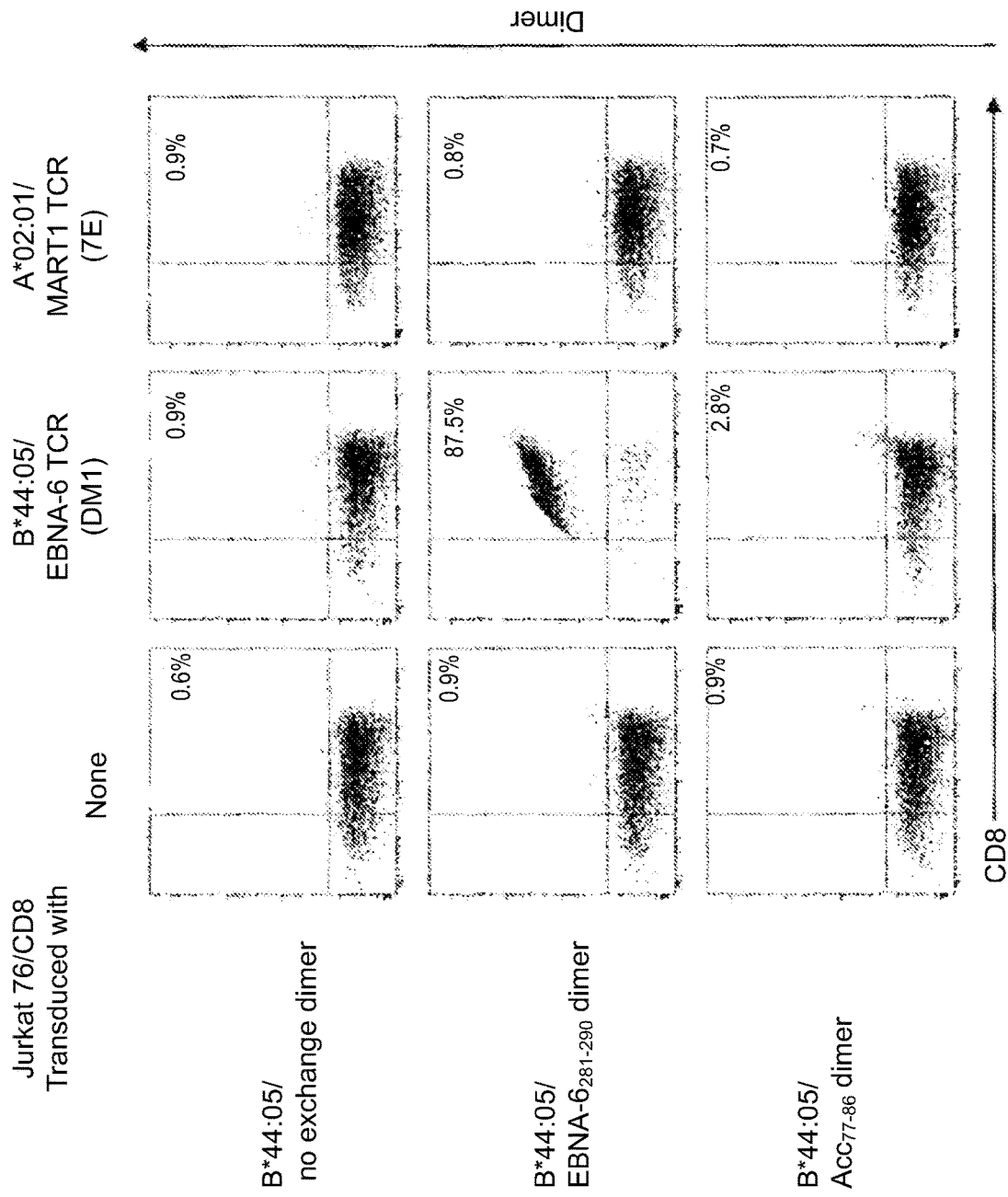
FIG. 13 shows B*44:05 dimer stains B*44:05/EBNA-6$_{281-290}$ TCR.

Soluble monomeric HLA-$B44^{Q115E}$-$K^b$ was loaded with B44/EBNA-$6_{281\text{-}290}$ (EENLLDFVRF), dimerized with PE-conjugated anti-His mAb, and used to stain Jurkat 76/CD8 T cells expressing clonotypic cognate TCR (FIG. 13).

Soluble Dimeric HLA-$C^{Q115E}$-$K^b$ Works as Well.

Figure 14:
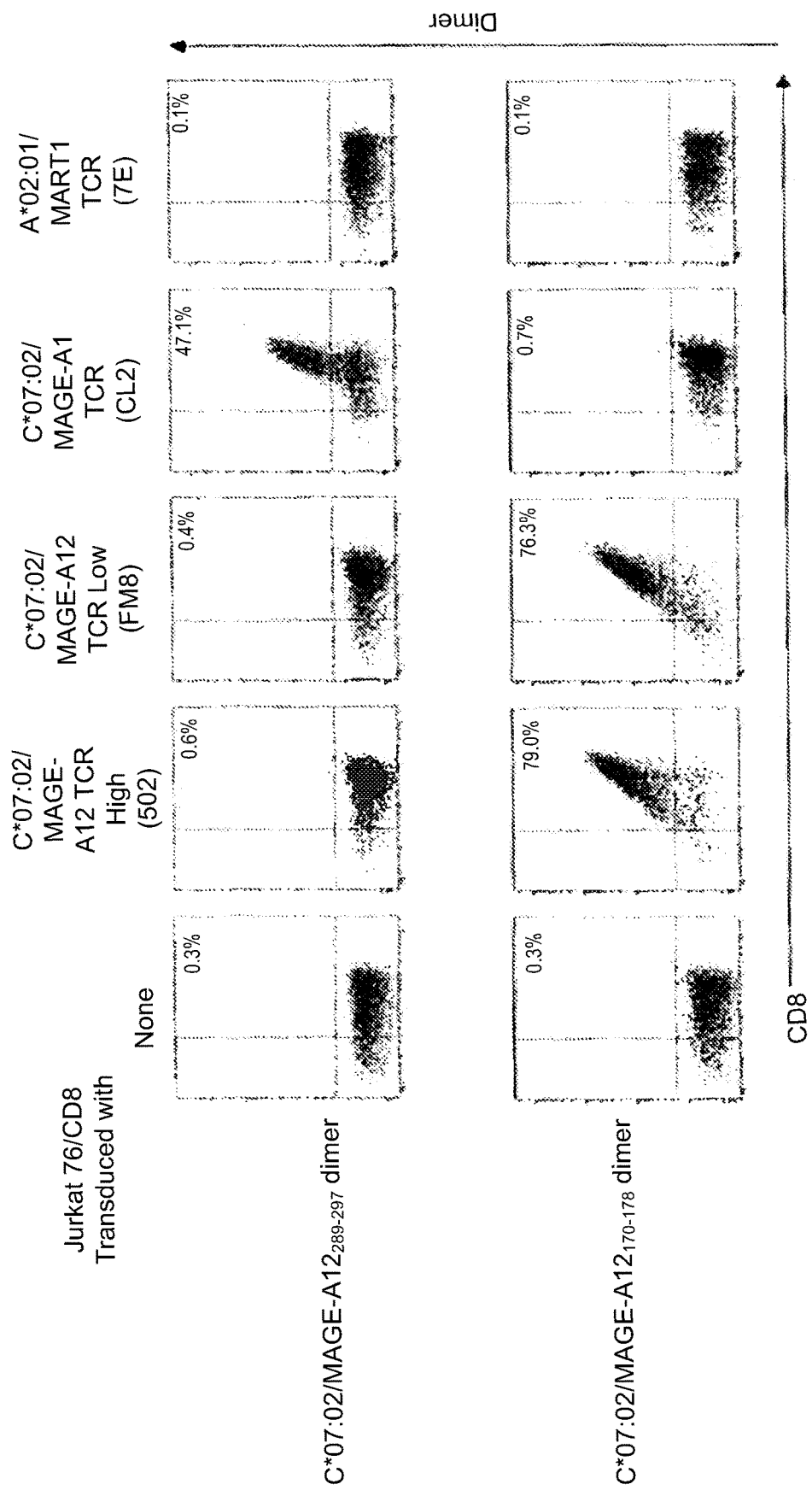
FIG. 14 shows C*07:02/MAGE-A1$_{289-297}$ and C*07:02/MAGE-A12$_{170-178}$ dimers stain respective TCRs.
Figure 16:
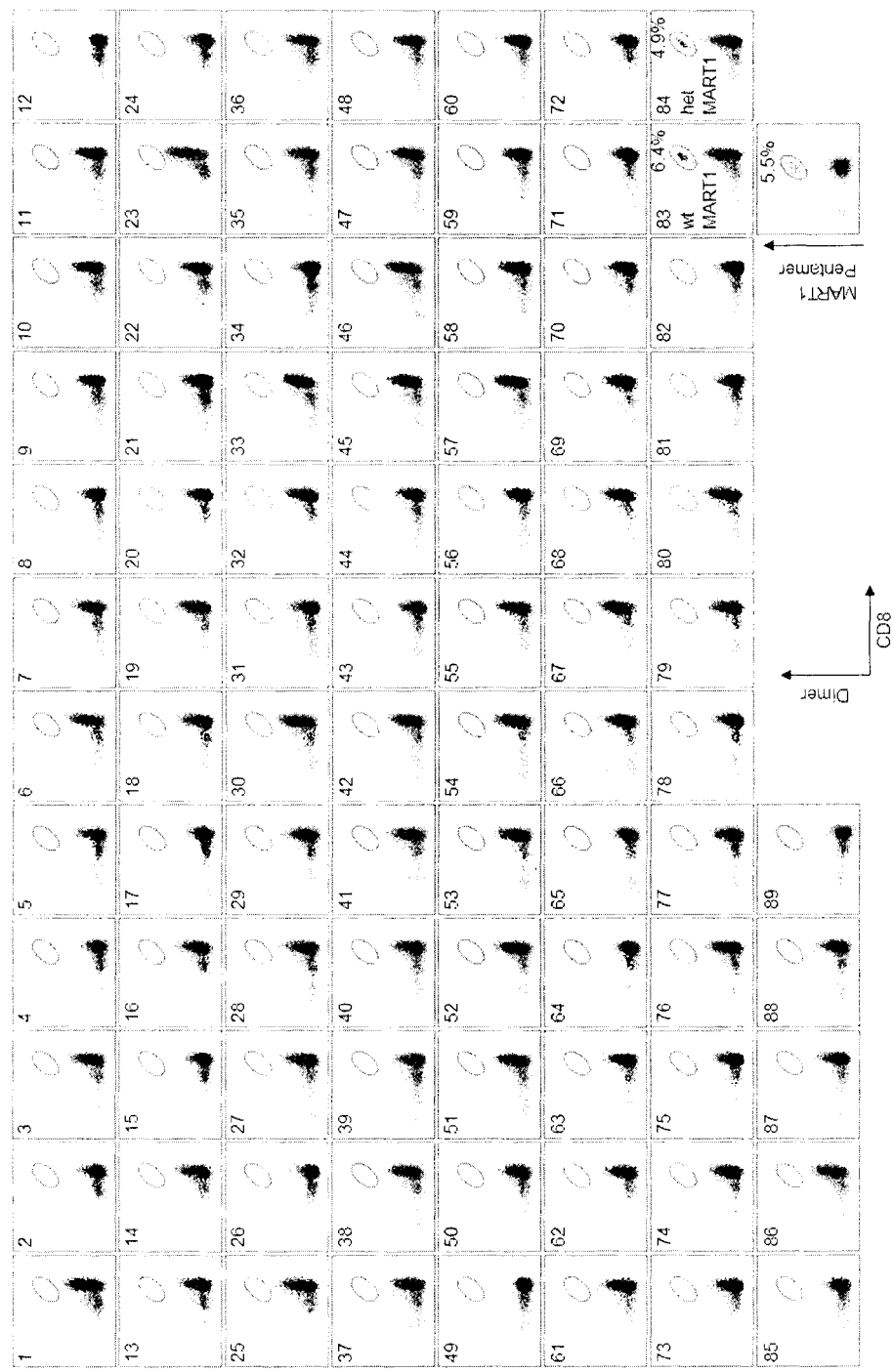
FIG. 16 shows high throughput A2 dimer staining of TILs (TIL: M25 TIL16 REP1 2E7 2016-9-15).
Figure 17:
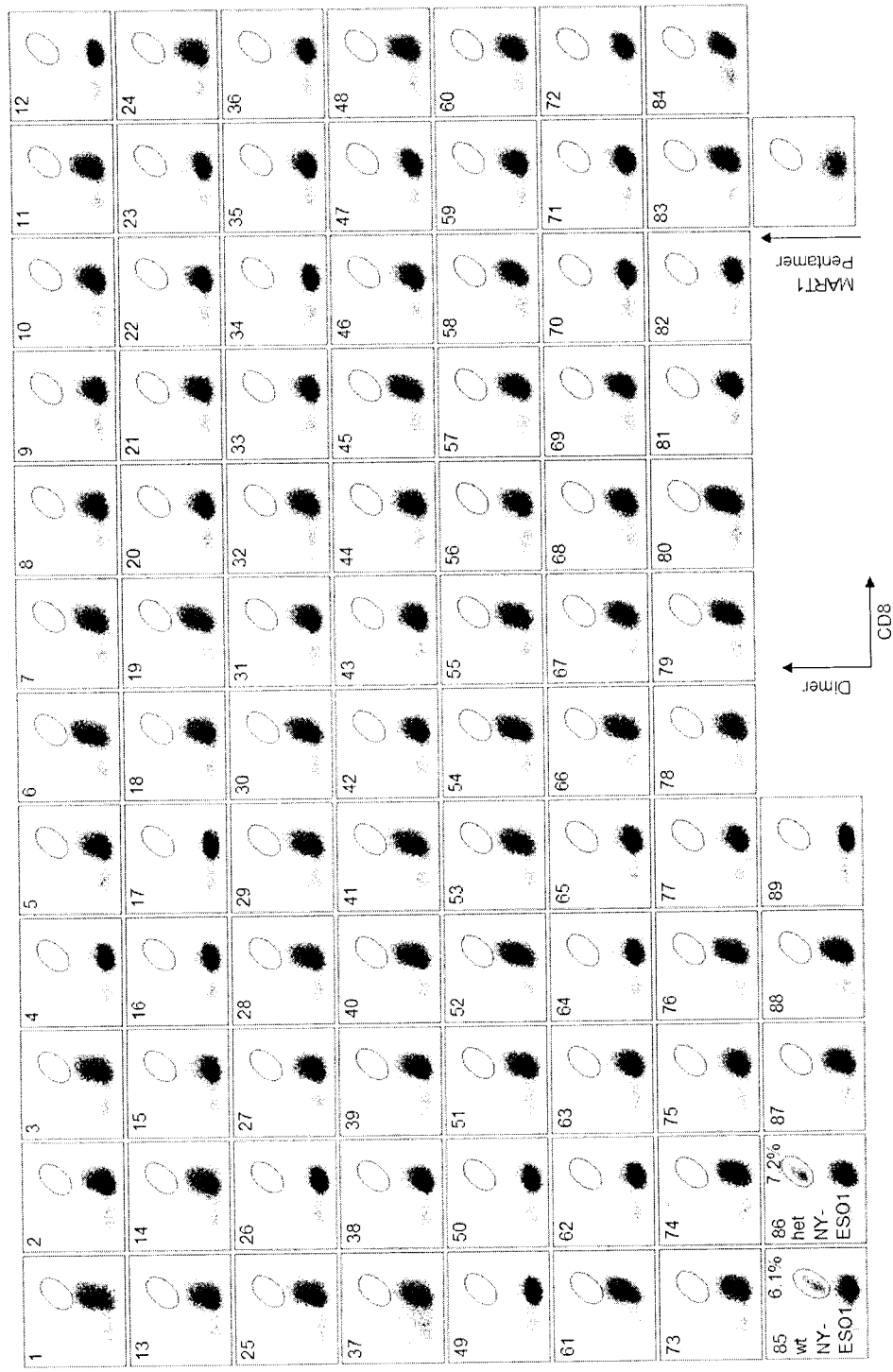
FIG. 17 shows high throughput A2 dimer staining of TILs (TIL: M31 TIL3 REP1A 2E7 2015-06-03).
Figure 18:
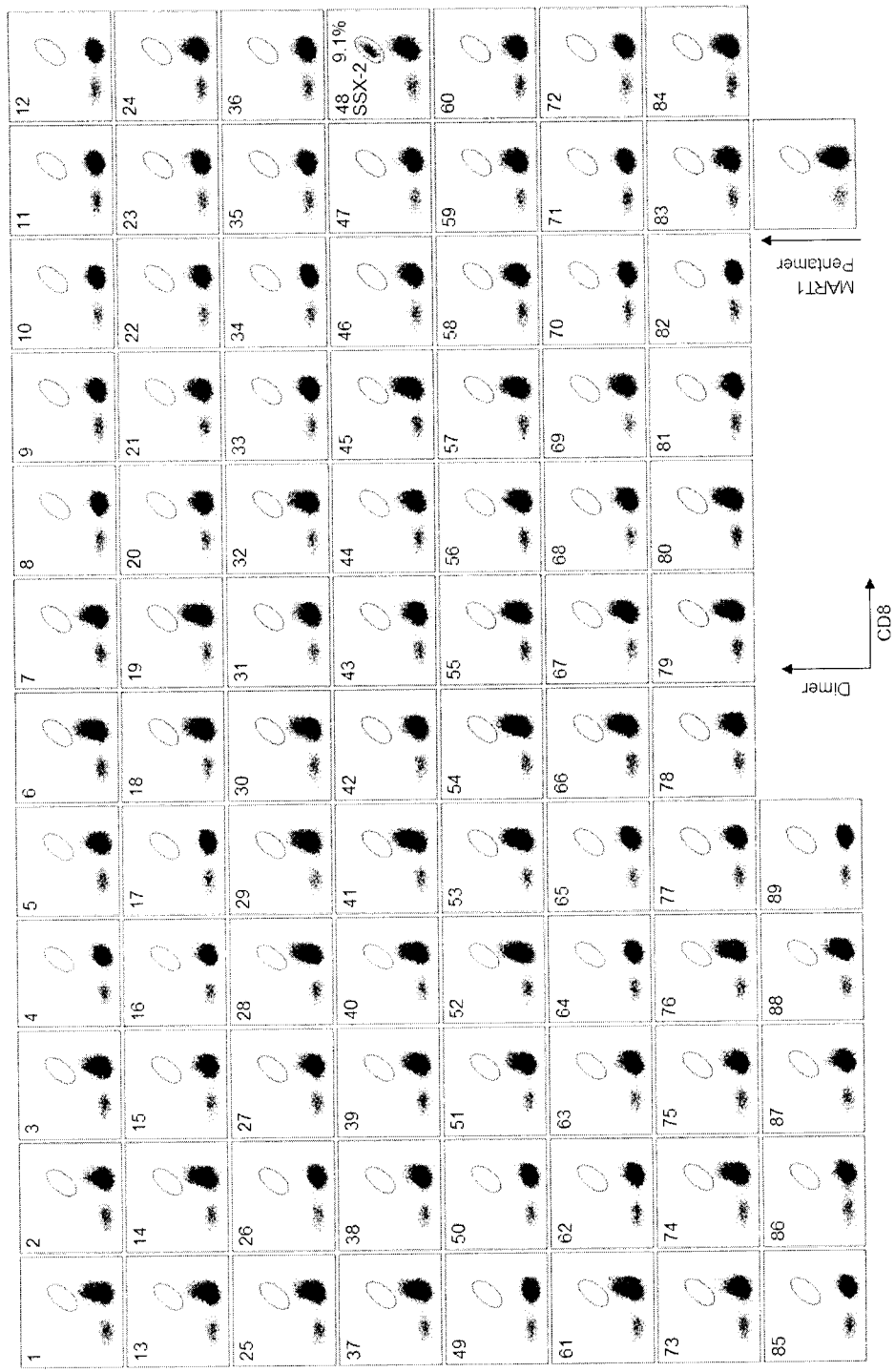
FIG. 18 shows high throughput A2 dimer staining of TILs (TIL: M37 TIL3 REP1B 2E7 2015-06-03).
Figure 19:
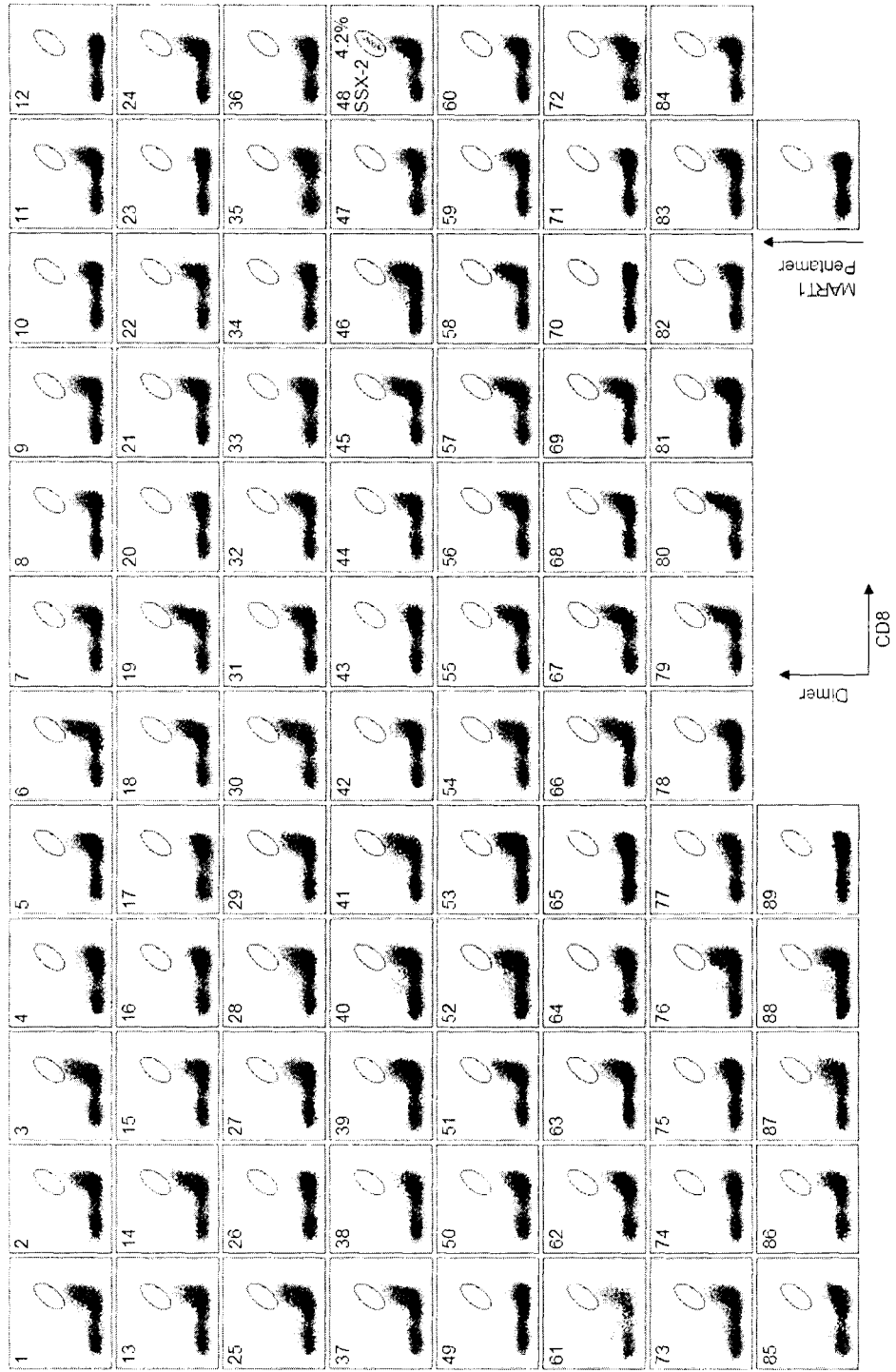
FIG. 19 shows high throughput A2 dimer staining of TILs (TIL: M40 TIL3 REP1A 2E7 2015-06-04).
Figure 20:
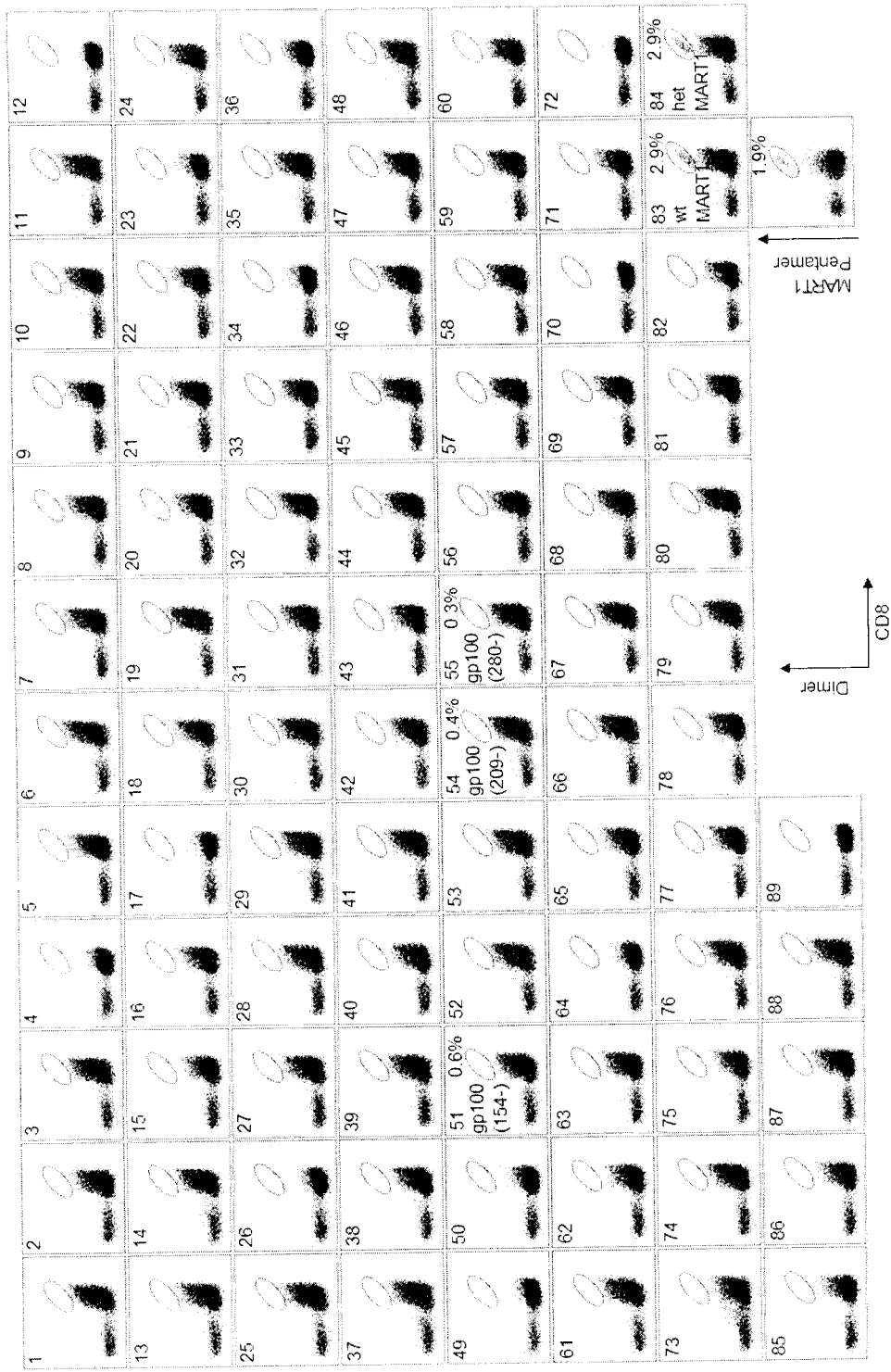
FIG. 20 shows high throughput A2 dimer staining of TILs (TIL: M66 YT REP1A D14 2E7 2012-02-01).
Figure 21:
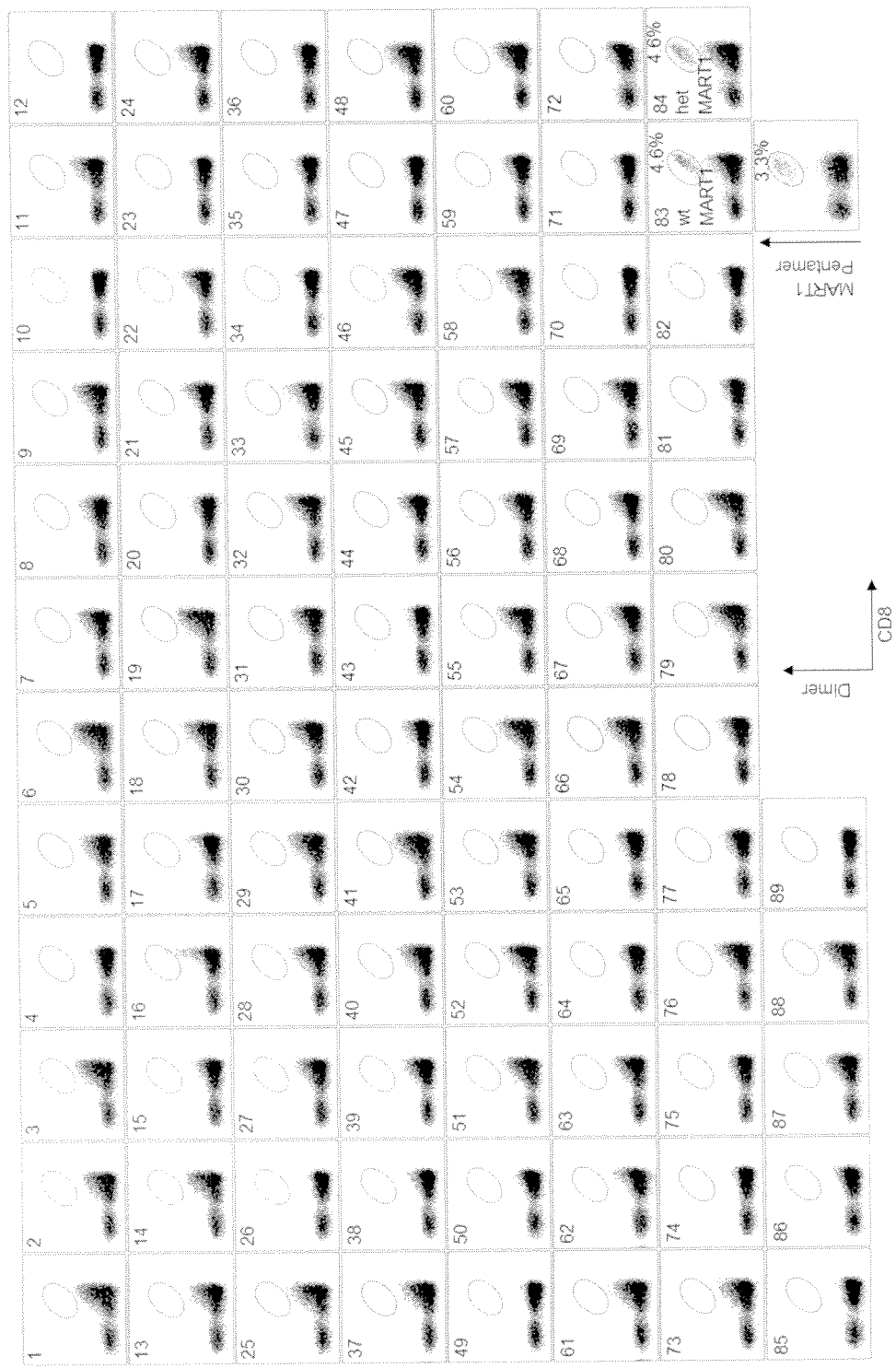
FIG. 21 shows high throughput A2 dimer staining of TILs (TIL: M96 YT REP1A 2E7 2015-06-04).
Figure 22:
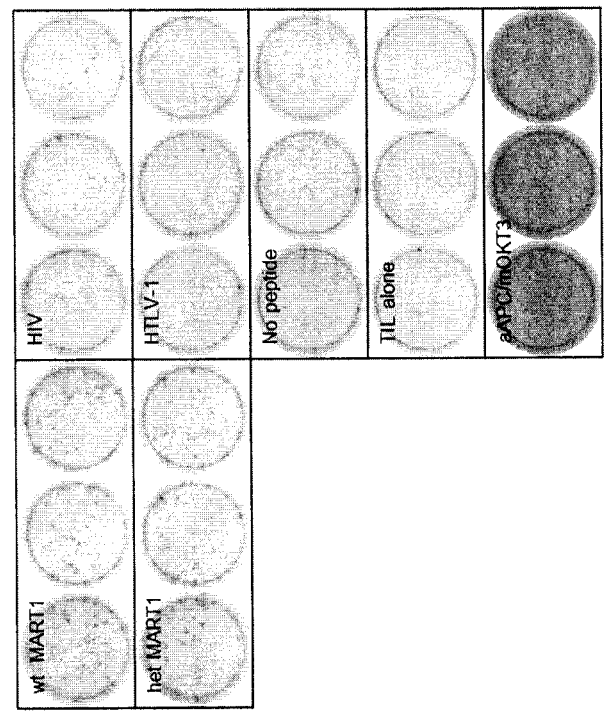
FIG. 22 shows IFN-γ ELISPOT assay (TIL: M25 TIL16 REP1 2E7 2016-9-15).
Figure 22:
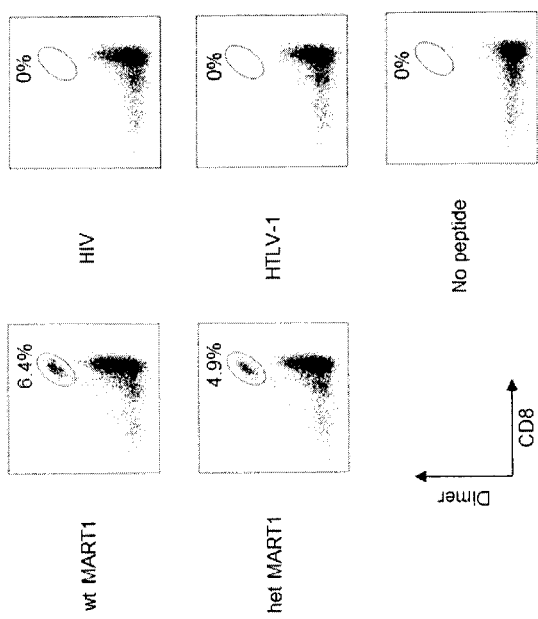
Figure 23:
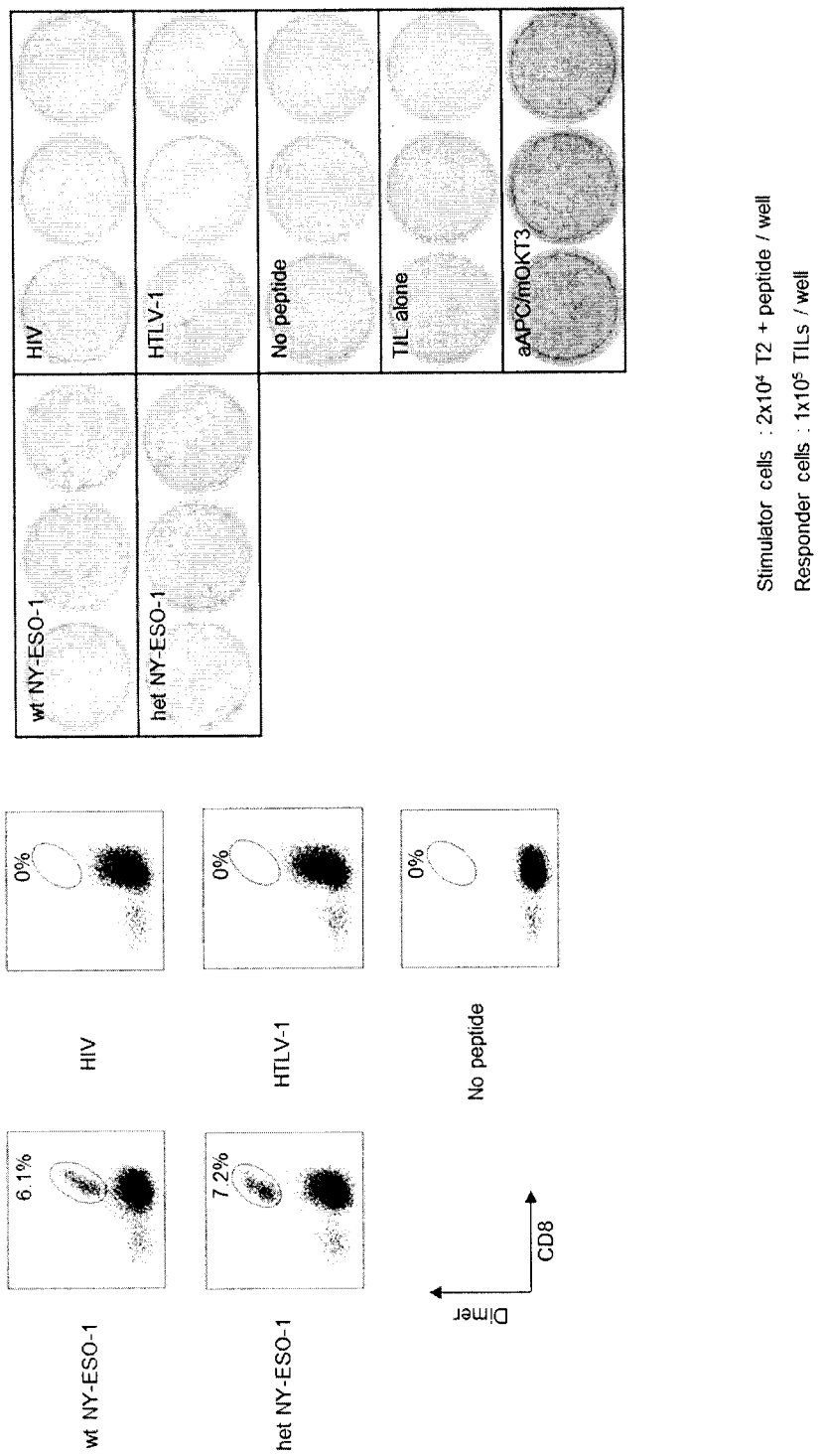
FIG. 23 shows IFN-γ ELISPOT assay (TIL: M31 TIL3 REP1A 2E7 2015-06-03).
Figure 24:
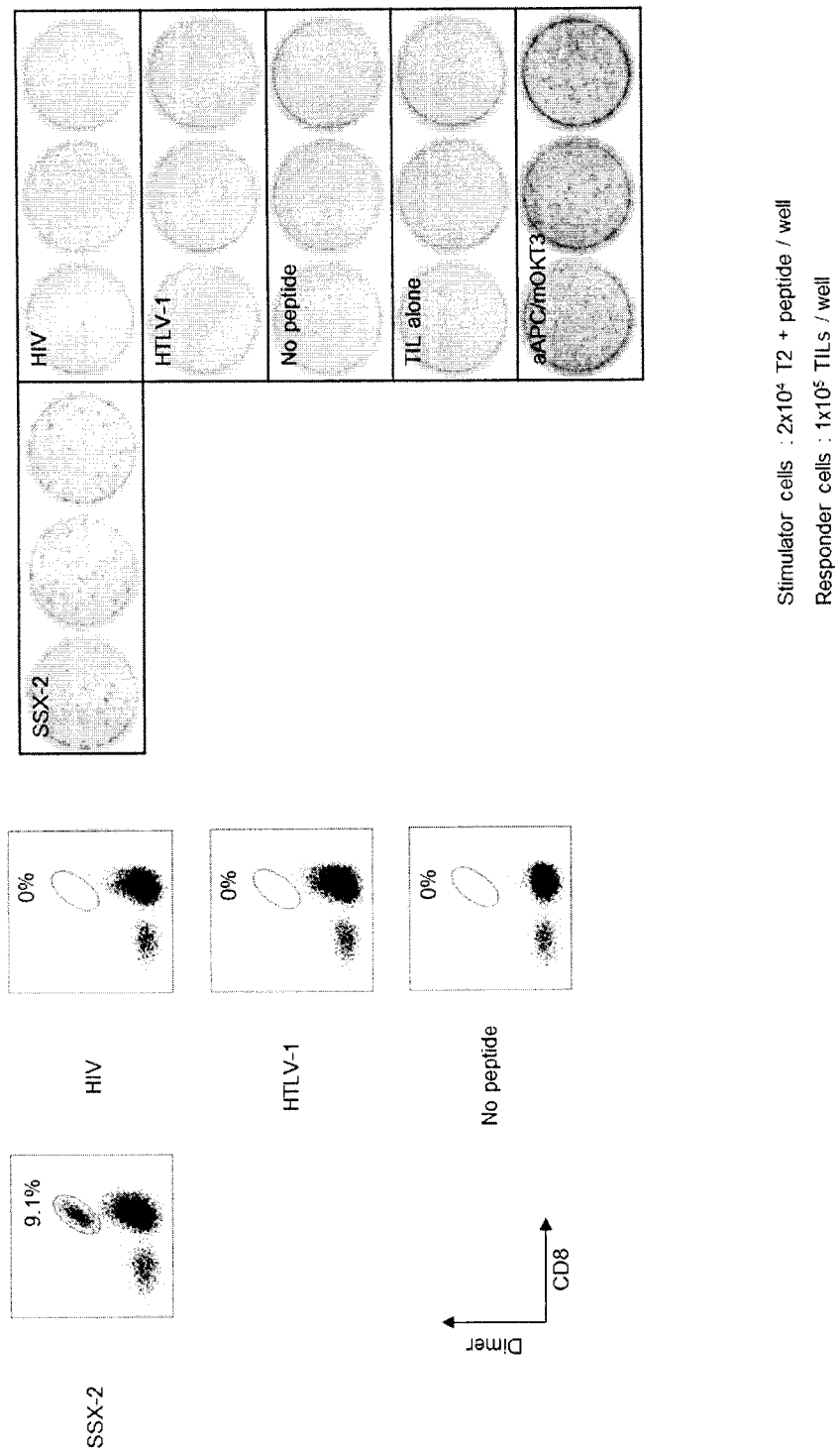
FIG. 24 shows IFN-γ ELISPOT assay (TIL: M37 TIL3 REP1B 2E7 2015-06-03).
Figure 25:
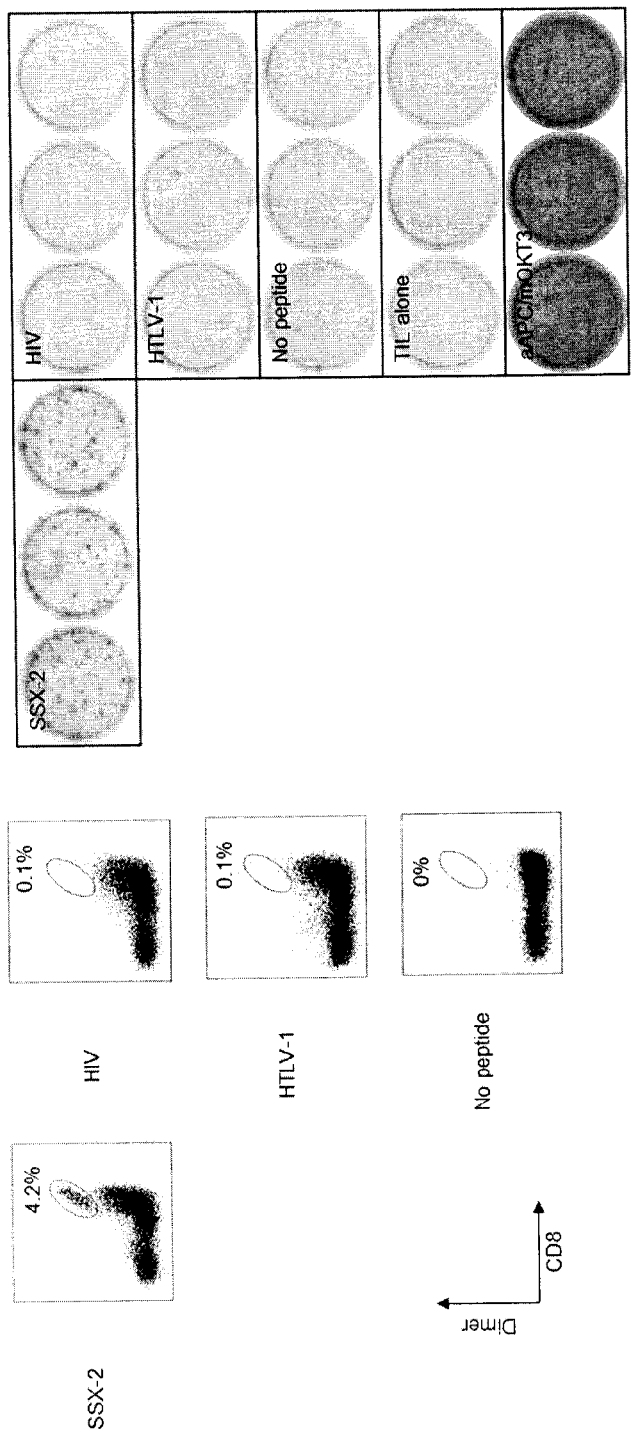
FIG. 25 shows IFN-γ ELISPOT assay (TIL: M40 TIL3 REP1A 2E7 2015-06-04).
Figure 26:
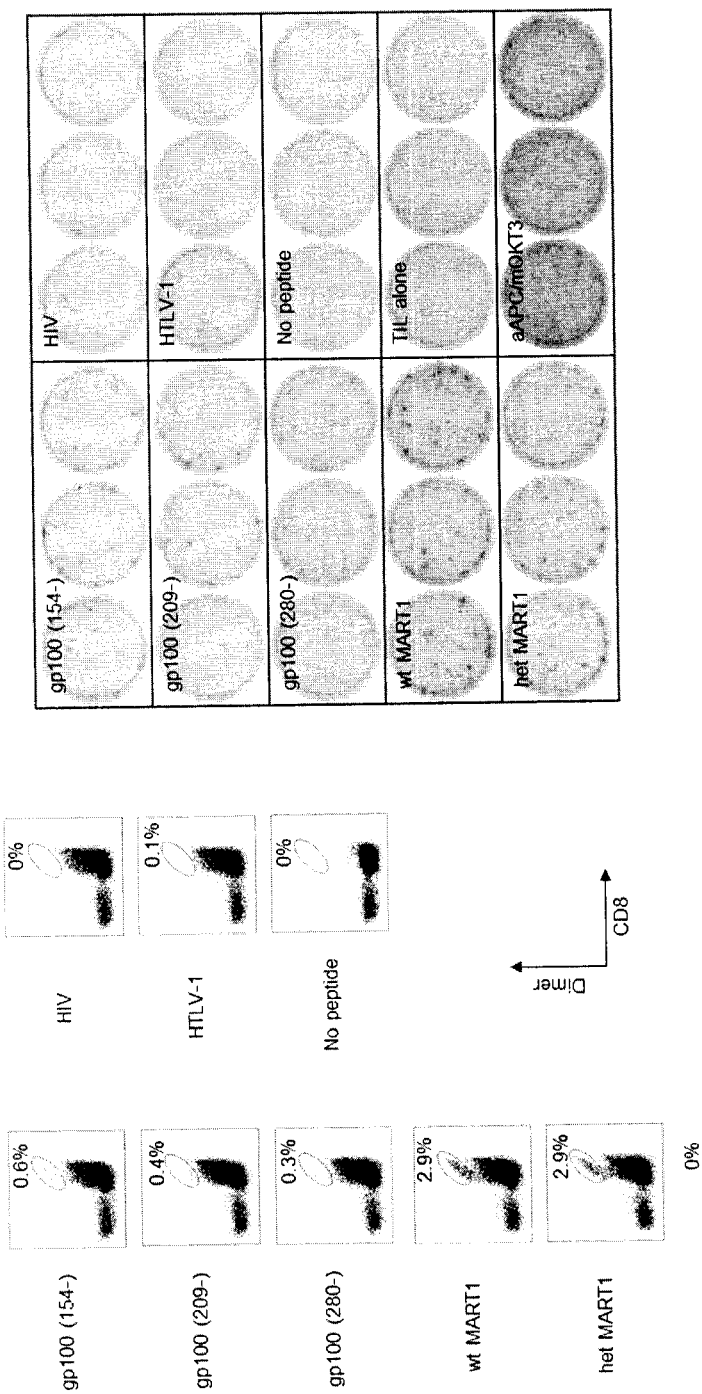
FIG. 26 shows IFN-γ ELISPOT assay (TIL: M66 YT REP1A D14 2E7 2012-02-01).
Figure 27:
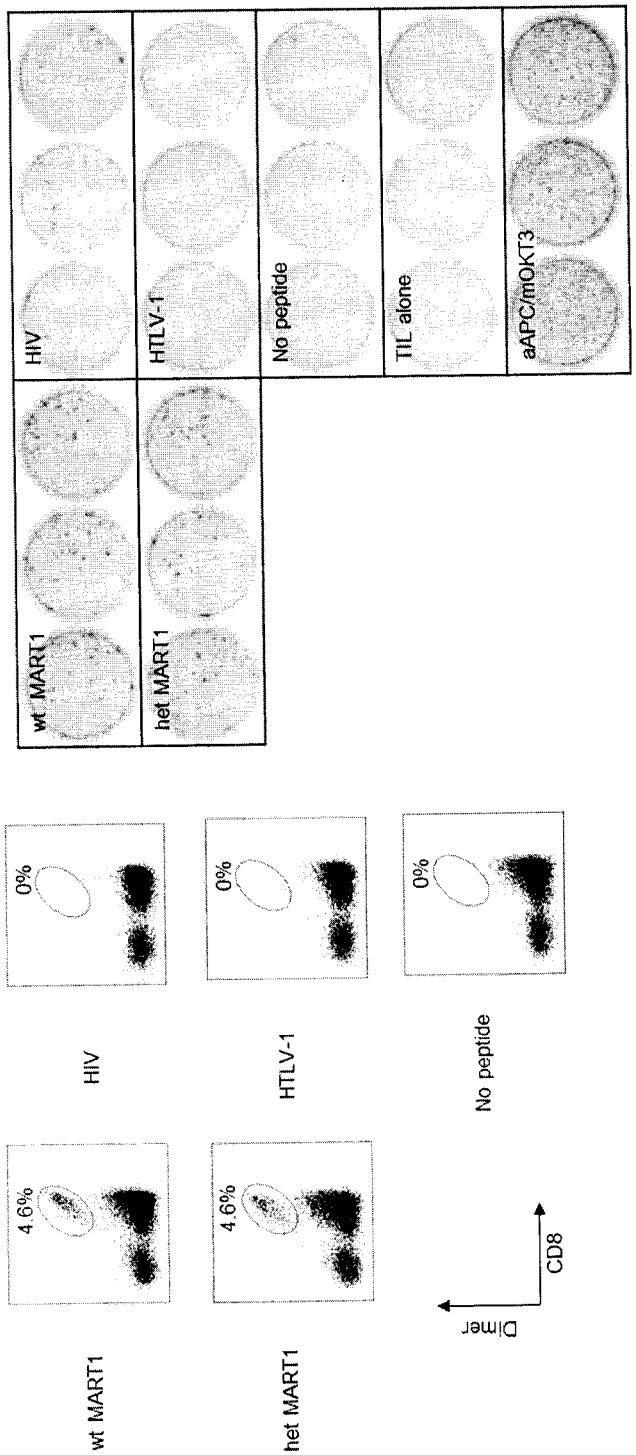
FIG. 27 shows IFN-γ ELISPOT assay (TIL: M96 YT REP1A 2E7 2015-06-04).

Soluble monomeric HLA-$C7^{Q115E}$-$K^b$ was loaded with C7/MAGE-$A1_{289\text{-}297}$ (RVRFFFPSL) peptide and C7/MAGE-$A12_{170\text{-}178}$ (VRIGHLYIL) peptide, dimerized with PE-conjugated anti-His mAb, and used to stain Jurkat 76/CD8 T cells expressing clonotypic cognate TCR (FIG. 14).

Staining of In Vitro Expanded Tumor-Infiltrating Lymphocytes with a Panel of Soluble A2 Dimers.

Peripheral T cells do not always reflect the immune response to the tumor taking place in cancer patients and antitumor cellular immunity in the periphery does not often correlate with prognosis. In contrast, tumor infiltrating lymphocytes (TILs) interact more closely with the tumor cells and are likely to reflect the tumor host interaction with higher fidelity. The use of TILs as a graft for adoptive cell transfer therapy to treat cancer has been pioneered by Rosenberg's group at the National Cancer Institute in the US[28].

It is believed that TILs are a polyclonal population of T cells with various antigen specificities[29]. To investigate the tumor specificity of TILs using our soluble dimer pHLA technology, TILs were isolated from nine HLA-A2+ patients with metastatic melanoma and grown in vitro as reported previously[14]. A large panel of 8-11 mer peptides derived from proteins highly expressed by autologous tumor cells were predicted using publicly available algorithms as reported previously (see Table 1)[18,23,30]. A library of soluble dimeric $A2^{Q118E}$-$K^b$ loaded with the predicted A2 peptides were produced as described above and used to stain the TILs (see FIG. 12 and FIG. 15-21). A2/HIV $pol_{478\text{-}484}$ and A2/$MART1_{28\text{-}35}$ Pentamers from ProImmune were utilized as a negative and positive control, respectively. The result showed that the in vitro grown TILs possessed reactivity to MART1, which is one of the well-established melanoma-associated antigen (uniprot.org/uniprot/Q16655).

Functional Assays of Dimer+ T Cells

Using ELISPOT assays, A2-restricted peptide-specific IFN-γ secretion was confirmed for all the 6 TIL samples for which dimer staining was positive. PVDF plates (Millipore, Bedford, Mass.) were coated with capture mAb (1 D1K; MABTECH, Mariemont, Ohio). TILs were incubated with $2\times10^4$ per well of T2 cells in the presence of each peptide for 20-24 hours at 37° C. The plates were washed and incubated with biotin-conjugated detection mAb (7-B6-1; MABTECH). HRP-conjugated SA (Jackson ImmunoResearch) was then added, and IFN-γ spots were developed. The reaction was stopped by rinsing thoroughly with cold tap water. ELISPOT plates were scanned and counted using an ImmunoSpot plate reader and ImmunoSpot version 5.0 software (Cellular Technology Limited, Shaker Heights, Ohio) (FIG. 22-27).

A summary of dimer staining and ELISPOT assays of TILs is shown in FIG. 28.

Enrichment of Dimer Positive TILs

Figure 29:
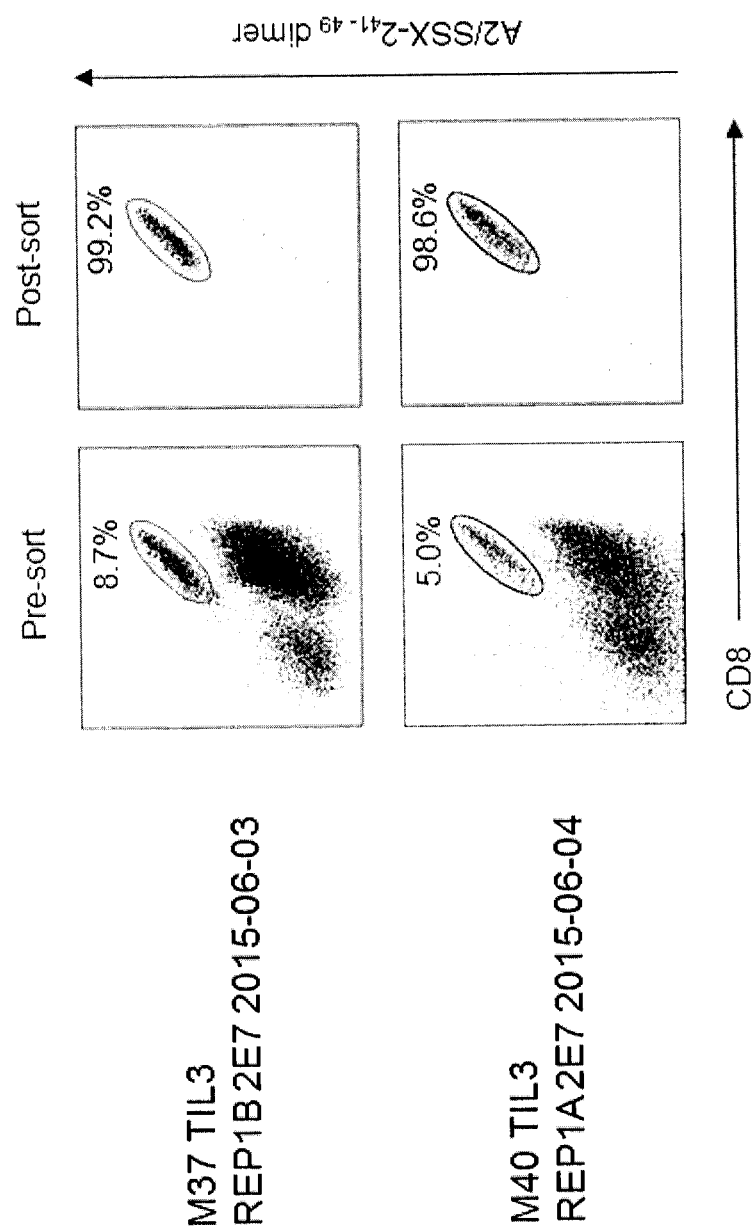
FIG. 29 shows Enrichment of dimer positive TILs.

Two TIL samples (M37 TIL3 REP1B 2E7 2015-06-03 and M40 TIL3 REP1A 2E7 2015-06-04) were stained with A2/SSX-$2_{41\text{-}49}$ dimer and A2/SSX-$2_{41\text{-}49}$ T cells were purified using flow-cytometry-guided sorting (FIG. 29).

Possible Advantages.

There are a number of possible advantages of the present methods. The present HLA class I molecules may represent a more natural folding and/or glycosylation of the protein. The present HLA molecules might be produced in relatively quick fashion (~2 days vs. 4-10 days using conventional methods). Peptides might be exchanged relatively simply in vitro. A simpler protocol resulting in a more natural product might also result in significant cost savings.

Sequences

Soluble a*02:01-Wt, Nucleotide Sequence (SEQ ID NO.1) and Amino Acid Sequence (SEQ ID NO.2)

Sequences are listed in the following order:

Signal peptide derived from Fibroin-L (in regular Arial font below)
HLA-A*02:01 α1 domain (underlined below)
HLA-A*02:01 α2 domain (in bold below)
HLA-A*02:01 α3 domain (in italics below)
Flexible GS linker (in bold and underlined below)
6×His tag (in bold and italics below)

SEQ ID NO. 1
ATGATGCGGCCCATCGTGCTGGTGCTGCTGTTTGCCACATCTGCCCT

GGCCGGAAGCCACAGCATGCGGTACTTTTTCACCAGCGTGTCCAGAC

CCGGCAGAGGCGAGCCCAGATTCATTGCCGTGGGCTACGTGGACGAC

ACCCAGTTCGTCAGATTCGACAGCGACGCCGCCAGCCAGCGGATGGA

ACCTAGAGCCCCTTGGATCGAGCAGGAAGGCCCCGAGTACTGGGACG

GCGAGACACGGAAAGTGAAGGCCCACAGCCAGACCCACAGAGTGGAT

CTGGGCACCCTGCGGGGCTACTACAATCAGTCTGAGGCCGGCTCCCA

CACCGTGCAGAGGATGTACGGCTGTGACGTGGGCAGCGACTGGCGGT

TCCTGAGAGGCTACCACCAGTACGCCTACGACGGCAAGGACTATATC

GCCCTGAAAGAGGACCTGCGGAGCTGGACAGCCGCCGATATGGCCGC

CCAGACCACCAAGCACAAATGGGAAGCCGCCCACGTGGCCGAGCAGC

TGAGAGCTTATCTGGAAGGCACCTGTGTGGAATGGCTGCGGAGATAC

*CTGGAAAACGGCAAAGAGACACTGCAG*CGCACGGACGCCCCCAAAAC

*GCATATGACTCACCACGCTGTCTCTGACCATGAAGCCACCCTGAGGT*

*GCTGGGCCCTGAGCTTCTACCCTGCGGAGATCACACTGACCTGGCAG*

*CGGGATGGGGAGGACCAGACCCAGGACACGGAGCTCGTGGAGACCAG*

-continued
```
GCCTGCAGGGGATGGAACCTTCCAGAAGTGGGCGGCTGTGGTGGTGC

CTTCTGGACAGGAGCAGAGATACACCTGCCATGTGCAGCATGAGGGT

TTGCCCAAGCCCCTCACCCTGAGATGGGAGCCGGCAGC

CACCACCACCATCACCATTGA
```

SEQ ID NO. 2
MMRPIVLVLLFATSALAGSHSMRYFFTSVSRPGRGEPRFIAVGYVDD

TQFVRFDSDAASQRMEPRAPWIEQEGPEYWDGETRKVKAHSQTHRVD

LGTLRGYYNQSEAGSHTVQRMYGCDVGSDWRFLRGYHQYAYDGKDYI

ALKEDLRSWTAADMAAQTTKHKWEAAHVAEQLRAYLEGTCVEWLRRY

LENGKETLQRTDAPKTHMTHHAVSDHEATLRCWALSFYPAEITLTWQ

RDGEDQTQDTELVETRPAGDGTFQKWAAVVVPSGQEQRYTCHVQHEG

LPKPLTLRWEPGSHHHHHH

Soluble A*02:01-K$^b$, Nucleotide Sequence (SEQ ID NO.3) and Amino Acid Sequence (SEQ ID NO.4)
Sequences are listed in the following order:
Signal peptide derived from Fibroin-L (in regular Arial font below)
HLA-A*02:01 α1 domain (underlined below)
HLA-A*02:01 α2 domain (in bold below)
Mouse K$^b$ α3 domain (in italics below)
Flexible GS linker (in bold and underlined below)
6×His tag (in bold and italics below)

SEQ ID NO. 3
```
ATGATGCGGCCCATCGTGCTGGTGCTGCTGTTTGCCACATCTGCCCT

GGCCGGAAGCCACAGCATGCGGTACTTTTTCACCAGCGTGTCCAGAC

CCGGCAGAGGCGAGCCCAGATTCATTGCCGTGGGCTACGTGGACGAC

ACCCAGTTCGTCAGATTCGACAGCGACGCCGCCAGCCAGCGGATGGA

ACCTAGAGCCCCTTGGATCGAGCAGGAAGGCCCCGAGTACTGGGACG

GCGAGACACGGAAAGTGAAGGCCCACAGCCAGACCCACAGAGTGGAT

CTGGGCACCCTGCGGGGCTACTACAATCAGTCTGAGGCCGGCTCCCA
```

-continued
```
CACCGTGCAGAGGATGTACGGCTGTGACGTGGGCAGCGACTGGCGGT

TCCTGAGAGGCTACCACCAGTACGCCTACGACGGCAAGGACTATATC

GCCCTGAAAGAGGACCTGCGGAGCTGGACAGCCGCCGATATGGCCGC

CCAGACCACCAAGCACAAATGGGAAGCCGCCCACGTGGCCGAGCAGC

TGAGAGCTTATCTGGAAGGCACCTGTGTGGAATGGCTGCGGAGATAC

CTGGAAAACGGCAAAGAGACACTGCAGCGCACAGATTCCCCAAAGGC

CCATGTGACCCATCACAGCAGACCTGAAGATAAAGTCACCCTGAGGT

GCTGGGCCCTGGGCTTCTACCCTGCTGACATCACCCTGACCTGGCAG

TTGAATGGGGAGGAGCTGATCCAGGACATGGAGCTTGTGGAGACCAG

GCCTGCAGGGGATGGAACCTTCCAGAAGTGGGCATCTGTGGTGGTGC

CTCTTGGGAAGGAGCAGTATTACACATGCCATGTGTACCATCAGGGG

CTGCCTGAGCCCCTCACCCTGAGATGGGAGCCGGCAGC

CACCACCACCATCACCATTGA
```

SEQ ID NO. 4
MMRPIVLVLLFATSALAGSHSMRYFFTSVSRPGRGEPRFIAVGYVDD

TQFVRFDSDAASQRMEPRAPWIEQEGPEYWDGETRKVKAHSQTHRVD

LGTLRGYYNQSEAGSHTVQRMYGCDVGSDWRFLRGYHQYAYDGKDYI

ALKEDLRSWTAADMAAQTTKHKWEAAHVAEQLRAYLEGTCVEWLRRY

LENGKETLQRTDSPKAHVTHHSRPEDKVTLRCWALGFYPADITLTWQ

LNGEELIQDMELVETRPAGDGTFQKWASVVVPLGKEQYYTCHVYHQG

LPEPLTLRWEPGSHHHHHH

Soluble A*02:01$^{Q115E}$-K$^b$, Nucleotide Sequence (SEQ ID NO.5) and Amino Acid Sequence (SEQ ID NO.6)
Sequences are listed in the following order:
Signal peptide derived from Fibroin-L (in regular Arial font below)
HLA-A*02:01 α1 domain (underlined below)
HLA-A*02:01 α2 domain with Q115E mutation (in bold below)
Mouse K$^b$ α3 domain (in italics below)
Flexible GS linker (in bold and underlined below)
6×His tag (in bold and italics below)

SEQ ID NO. 5
```
ATGATGGGCCCATCGTGCTGGTGCTGCTGTTTGCCACATCTGCCCTGGCCGGA

AGCCACAGCATGCGGTACTTTTTCACCAGCGTGTCCAGACCCGGCAGAGGCGAG

CCCAGATTCATTGCCGTGGGCTACGTGGACGACACCCAGTTCGTCAGATTCGAC

AGCGACGCCGCCAGCCAGCGGATGGAACCTAGAGCCCCTTGGATCGAGCAGGA

AGGCCCCGAGTACTGGGACGGCGAGACACGGAAAGTGAAGGCCCACAGCCAGA

CCCACAGAGTGGATCTGGGCACCCTGCGGGGCTACTACAATCAGTCTGAGGCCG

GCTCCCACACCGTGCAGAGGATGTACGGCTGTGACGTGGGCAGCGACTGGCG

GTTCCTGAGAGGCTACCACGAGTACGCCTACGACGGCAAGGACTATATCGCCC

TGAAAGAGGACCTGCGGAGCTGGACAGCCGCCGATATGGCCGCCCAGACCAC

CAAGCACAAATGGGAAGCCGCCCACGTGGCCGAGCAGCTGAGAGCTTATCTG

GAAGGCACCTGTGTGGAATGGCTGCGGAGATACCTGGAAAAGGGCAAAGAGA

CACTGCAGCGCACAGATTCCCCAAAGGCCCATGTGACCCATCACAGGAGACCTG
```

```
                                    -continued
AAGATAAAGTCACCCTGAGGTGCTGGGCCCTGGGCTTCTACCCTGCTGACATCA

CCCTGACCTGGCAGTTGAATGGGGAGGAGCTGATCCAGGACATGGAGCTTGTGG

AGACCAGGCCTGCAGGGGATGGAACCTTCCAGAAGTGGGCATCTGTGGTGGTG

CCTCTTGGGAAGGAGCAGTATTACACATGCCATGTGTACCATCAGGGGCTGCCT

GAGCCCCTCACCCTGAGATGGGAGCCGGGCAGCCACCACCACCATCACCATTGA
                                                        SEQ ID NO. 6
MMRPIVLVLLFATSALAGSHSMRYFFTSVSRPGRGEPRFIAVGYVDDTQFVRFDSDA

ASQRMEPRAPWIEQEGPEYWDGETRKVKAHSQTHRVDLGTLRGYYNQSEAGSHTV

QRMYGCDVGSDWRFLRGYHEYAYDGKDYIALKEDLRSWTAADMAAQTTKHKWEA

AHVAEQLRAYLECTCVEWLRRYLENGKETLQRTDSPKAHVTHHSRPEDKVTLRCW

ALGFYPADITLTWQLNGEELIQDMELVETRPAGDGTFQKWASVVVPLGKEQYYTCHV

YHQGLPEPLTLRWEPGSHHHHHHZ
```

Soluble A*24:02-Wt, Nucleotide Sequence (SEQ ID NO.7) and Amino Acid Sequence (SEQ ID NO.8)

Sequences are listed in the following order:

Signal peptide derived from Fibroin-L (in regular Arial font below)

HLA-A*24:02 α1 domain (underlined below)
HLA-A*24:02 α2 domain (in bold below)
HLA-A*24:02 α3 domain (in italics below)
Flexible GS linker (in bold and underlined below)
6×His tag (in bold and italics below)

```
                                                        SEQ ID NO. 7
ATGATGCGGCCCATCGTGCTGGTGCTGCTGTTTGCCACATCTGCCCTGGCCGGC

TCCCACTCCATGAGGTATTTCTCCACATCCGTGTCCCGGCCCGGCCGCGGGGAG

CCCCGCTTCATCGCCGTGGGCTACGTGGACGACACGCAGTTCGTGCGGTTCGAC

AGCGACGCCGCGAGCCAGAGGATGGAGCCGCGGGCGCCGTGGATAGAGCAGG

AGGGGCGGGAGTATTGGGACGAGGAGACAGGGAAAGTGAAGGCCCACTCACAG

ACTGACCGAGAGAACCTGCGGATCGCGCTCCGCTACTACAACCAGAGCGAGGCC

GGTTCTCACACCCTCCAGATGATGTTTGGCTGCGACGTGGGGTCGGACGGGCG

CTTCCTCCGCGGGTACCACCAGTACGCCTACGACGGCAAGGATTACATCGCCC

TGAAAGAGGACCTGCGCTCTTGGACCGCGGCGGACATGGCGGCTCAGATCACC

AAGCGCAAGTGGGAGGCGGCCCATGTGGCGGAGCAGCAGAGAGCCTACCTGG

AGGGCACGTGCGTGGACGGGCTCCGCAGATACCTGGAGAACGGGAAGGAGAC

GCTGCAGCGCACGGACCCCCCCAAGACACATATGACCCACCACCCCATCTCTGA

CCATGAGGCCACTCTGAGATGCTGGGCCCTGGGCTTCTACCCTGCGGAGATCAC

ACTGACCTGGCAGCGGGATGGGGAGGACCAGACCCAGGACACGGAGCTTGTGG

AGACCAGGCCTGCAGGGGATGGAACCTTCCAGAAGTGGGCAGCTGTGGTGGTA

CCTTCTGGAGAGGAGCAGAGATACACCTGCCATGTGCAGCATGAGGGTCTGCCC

AAGCCCCTCACCCTGAGATGGGAGCCGGGCAGCCACCACCACCATCACCATTGA
                                                        SEQ ID NO. 8
MMRPIVLVLLFATSALAGSHSMRYFSTSVSRPGRGEPRFIAVGYVDDTQFVRFDSDA

ASQRMEPRAPWIEQEGPEYWDEETGKVKAHSQTDRENLRIALRYYNQSEAGSHTLQ

MMFGCDVGSDGRFLRGYHQYAYDGKDYIALKEDLRSWTAADMAAQITKRKWEAA

HVAEQQRAYLEGTCVDGLRRYLENGKETLQRTDPPKTHMTHHPISDHEATLRCWAL

GFYPAEITLTWQRDGEDQTQDTELVETRPAGDGTFQKWAAVVVPSGEEQRYTCHV

QHEGLPKPLTLRWEPGSHHHHHHZ
```

Soluble A*24:02-K$^b$, Nucleotide Sequence (SEQ ID NO.9) and Amino Acid Sequence (SEQ ID NO.10)
Sequences are listed in the following order:
Signal peptide derived from Fibroin-L (in regular Arial font below)
HLA-A*24:02 α1 domain (underlined below)
HLA-A*24:02 α2 domain (in bold below)
Mouse K$^b$ α3 domain (in italics below)
Flexible GS linker (in bold and underlined below)
6×His tag (in bold and italics below)

SEQ ID NO. 9

ATGATGCGGCCCATCGTGCTGGTGCTGCTGTTTGCCACATCTGGGCTGGCGGGC

TCCCACTCCATGAGGTATTTCTCCACATCCGTGTCCCGGCCCGGCCGCGGGGAG

CCCCGCTTCATCGCCGTGGGCTACGTGGACGACACGCAGTTCGTGCGGTTCGAC

AGCGACGCCGCGAGCCAGAGGATGGAGCCGCGGGCGCCGTGGATAGAGCAGG

AGGGGCCGGAGTATTGGGACGAGGAGACAGGGAAAGTGAAGGCCCACTCACAG

ACTGACCGAGAGAACCTGCGGATCGCGCTCCGCTACTACAACCAGAGCGAGGCC

GGTTCTCACACCCTCCAGATGATGTTTGGCTGCGACGTGGGGTCGGACGGGCG

CTTCCTCCGCGGGTACCACCAGTACGCCTACGACGGCAAGGATTACATCGCCC

TGAAAGAGGACCTGCGCTCTTGGACCGCGGCGGACATGGCGGCTCAGATCACC

AAGCGCAAGTGGGAGGCGGCCCATGTGGCGGAGCAGCAGAGAGCCTACCTGG

AGGGCACGTGCGTGGACGGGCTCCGCAGATACCTGGAGAACGGGAAGGAGAC

GCTGCAGCGCACAGATTCCCCAAAGGCCCATGTGACCCATCACAGCAGACCTGA

AGATAAAGTCACCCTGAGGTGCTGGGCCCTGGGCTTCTACCCTGCTGACATCAC

CCTGACCTGGCAGTTGAATGGGGAGGAGCTGATCCAGGACATGGAGCTTGTGGA

GACCAGGCCTGCAGGGGATGGAACCTTCCAGAAGTGGGCATCTGTGGTGGTGC

CTCTTGGGAAGGAGCAGTATTACACATGCCATGTGTACCATCAGGGGCTGCCTG

AGCCCCTCACCCTGAGATGGGAGCCGGGCAGCCACCACCACCATCACCATTGA

SEQ ID NO. 10

MMRPIVLVLLFATSALAGSHSMRYFSTSVSRPGRGEPRFIAVGYVDDTQFVRFDSDA

ASQRMEPRAPWIEQEGPEYWDEETGKVKAHSQTDRENLRIALRYYNQSEAGSHTLQ

MMFGCDVGSDGRFLRGYHQYAYDGKDYIALKEDLRSWTAADMAAQITKRKWEAA

HVAEQQRAYLEGTCVDGLRRYLENGKETLQRTDSPKAHVTHHSRPEDKVTLRCWA

LGFYPADITLTWQLNGEELIQDMELVETRPAGDGTFQKWASVVVPLGKEQYYTCHVY

HQGLPEPLTLRWEPGSHHHHHH

Soluble a*24:02$^{Q115E}$-K$^b$, Nucleotide Sequence (SEQ ID NO.11) and Amino Acid Sequence (SEQ ID NO.12)
Sequences are listed in the following order:
Signal peptide derived from Fibroin-L (in regular Arial font below)
HLA-A*24:02 α1 domain (underlined below)
HLA-A*24:02 α2 domain with Q115E mutation (in bold below)
Mouse K$^b$ α3 domain (in italics below)
Flexible GS linker (in bold and underlined below)
6×His tag (in bold and italics below)

SEQ ID NO. 11

ATGATGCGGCCCATCGTGCTGGTGCTGCTGTTTGCCACATCTGCCCTGGCCGGC

TCCCACTCCATGAGGTATTTCTCCACATCCGTGTCCCGGCCCGGCCGCGGGGAG

CCCCGCTTCATCGCCGTGGGCTACGTGGACGACACGCAGTTCGTGCGGTTCGAC

AGCGACGCCGCGAGCCAGAGGATGGAGCCGCGGGCGCCGTGGATAGAGCAGG

AGGGGCCGGAGTATTGGGACGAGGAGACAGGGAAAGTGAAGGCCCACTCACAG

-continued

ACTGACCGAGAGAACCTGCGGATCGCGCTCCGCTACTACAACCAGAGCGAGGCC

GGTTCTCACACCCTCCAGATGATGTTTGGCTGCGACGTGGGGTCGGACGGGCG

CTTCCTCCGCGGGTACCACGAGTACGCCTACGACGGCAAGGATTACATCGCCC

TGAAAGAGGACCTGCGCTCTTGGACCGCGGCGGACATGGCGGCTCAGATCACC

AAGCGCAAGTGGGAGGCGGCCCATGTGGCGGAGCAGCAGAGAGCCTACCTGG

AGGGCACGTGCGTGGACGGGCTCCGCAGATACCTGGAGAACGGGAAGGAGAC

GCTGCAGCGCACAGATTCCCCAAAGGCCCATGTGACCCATCACAGCAGACCTGA

AGATAAAGTCACCCTGAGGTGCTGGGCCCTGGGCTTCTACCCTGCTGACATCAC

CCTGACCTGGCAGTTGAATGGGGAGGAGCTGATCCAGGACATGGAGCTTGTGGA

GACCAGGCCTGCAGGGGATGGAACCTTCCAGAAGTGGGCATCTGTGGTGGTGC

CTCTTGGGAAGGAGCAGTATTACACATGCCATGTGTACCATCAGGGGCTGCCTG

AGCCCCTCACCCTGAGATGGGAGCCG<u>GGCAGC</u>CACCACCACCATCACCATTGA

SEQ ID NO. 12

MMRPIVLVLLFATSALA<u>GSHSMRYFSTSVSRPGRGEPRFIAVGYVDDTQFVRFDSDA</u>

<u>ASQRMEPRAPWIEQEGPEYWDEETGKVKAHSQTDRENLRIALRYYNQSEA</u>GSHTLQ

MMFGCDVGSDGRFLRGYHEYAYDGKDYIALKEDLRSWTAADMAAQITKRKWEAA

HVAEQQRAYLEGTCVDGLRRYLENGKETLQ*RTDSPKAHVTHHSRPEDKVTLRCWA*

*LGFYPADITLTWQLNGEELIQDMELVETRPAGDGTFQKWASVVVPLGKEQYYTCHVY*

*HQGLPEPLTLRWEP*<u>GS</u>*HHHHHH*

Soluble B*35:01$^{Q115E}$-K$^b$, Nucleotide Sequence (SEQ ID NO.13) and Amino Acid Sequence (SEQ ID NO.14)
Sequences are listed in the following order:
Signal peptide derived from Fibroin-L (in regular Arial font below)
HLA-B*35:01 α1 domain (underlined below)

HLA-B*35:01 α2 domain with Q115E mutation (in bold below)
Mouse K$^b$ α3 domain (in italics below)
Flexible GS linker (in bold and underlined below)
6×His tag (in bold and italics below)

SEQ ID NO. 13

ATGATGCGGCCCATCGTGCTGGTGCTGCTGTTTGCCACATCTGCCCTGGCC<u>GGC</u>

<u>TCCCACTCCATGAGGTATTTCTACACCGCCATGTCCCGGCCCGGCCGCGGGGAG</u>

<u>CCCCGCTTCATCGCAGTGGGCTACGTGGACGACACCCAGTTCGTGAGGTTCGAC</u>

<u>AGCGACGCCGCGAGTCCGAGGACGGAGCCCCGGGCGCCATGGATAGAGCAGG</u>

<u>AGGGGCCGGAGTATTGGGACCGGAACACACAGATCTTCAAGACCAACACACAGA</u>

<u>CTTACCGAGAGAGCCTGCGGAACCTGCGCGGCTACTACAACCAGAGCGAGGCC</u>

GGGTCTCACATCATCCAGAGGATGTATGGCTGCGACCTGGGGCCCGACGGGCG

CCTCCTCCGCGGGCATGACCAGTCCGCCTACGACGGCAAGGATTACATCGCCC

TGAACGAGGACCTGAGCTCCTGGACCGCGGCGGACACCGCGGCTCAGATCAC

CCAGCGCAAGTGGGAGGCGGCCCGTGTGGCGGAGCAGCTGAGAGCCTACCTG

GAGGGCCTGTGCGTGGAGTGGCTCCGCAGATACCTGGAGAACGGGAAGGAGA

CGCTGCAGCGCGCGGACCCCCCAAAGACACACGTGACCCACCACCCCGTCTCT

*GACCATGAGGCCACCCTGAGGTGCTGGGCCCTGGGCTTCTACCCTGCGGAGAT*

*CACACTGACCTGGCAGCGGGATGGCCAGGACCAAACTCAGGACACTGAGCTTGT*

*GGAGACCAGACCAGCAGGAGATAGAACCTTCCAGAAGTGGGCAGCTGTGGTGGT*

-continued
```
GCCTTCTGGAGAAGAGCAGAGATACACATGCCATGTACAGCATGAGGGGCTGCC

CAAGCCCCTCACCCTGAGATGGGAGCCGGCAGCCACCACCACCATCACCATTGA
```

SEQ ID NO. 14
```
MMRPIVLVLLFATSALAGSHSMRYFYTAMSRPGRGEPRFIAVGYVDDTQFVRFDSDA

ASPRTEPRAPWIEQEGPEYWDRNTQIFKTNTQTYRESLRNLRGYYNQSEAGSHIIQR

MYGCDLGPDGRLLRGHDQSAYDGKDYIALNEDLSSWTAADTAAQITQRKWEAARV

AEQLRAYLEGLCVEWLRRYLENGKETLQRADPPKTHVTHHPVSDHEATLRCWALG

FYPAEITLTWQRDGEDQTQDTELVETRPAGDRTFQKWAAVVVPSGEEQRYTCHVQH

EGLPKPLTLRWEPGSHHHHHH
```

Soluble B*40:02$^{Q115E}$-Kb, Nucleotide Sequence (SEQ ID NO. 15) and Amino Acid Sequence (SEQ ID NO. 16)
Sequences are listed in the following order:
Signal peptide derived from Fibroin-L (in regular Arial font below)
HLA-B*40:02 α1 domain (underlined below)
HLA-B*40:02 α2 domain with Q115E mutation (in bold below)
Mouse K$^b$ α3 domain (in italics below)
Flexible GS linker (in bold and underlined below)
6×His tag (in bold and italics below)

Soluble B*44:05$^{Q115E}$-Kb, Nucleotide Sequence (SEQ ID NO. 17) and Amino Acid Sequence (SEQ ID NO. 18)
Sequences are listed in the following order:
Signal peptide derived from Fibroin-L (in regular Arial font below)
HLA-B*44:05 α1 domain (underlined below)
HLA-B*44:05 α2 domain with Q115E mutation (in bold below)
Mouse K$^b$ α3 domain (in italics below)
Flexible GS linker (in bold and underlined below)
6×His tag (in bold and italics below)

SEQ ID NO. 15
```
ATGATGCGGCCCATCGTGCTGGTGCTGCTGTTTGCCACATCTGCCCTGGCCGGC

TCCCACTCCATGAGGTATTTCTACACCGCCATGTCCCGGCCCGGCCGCGGGGAG

CCCCGCTTCATCGCAGTGGGCTACGTGGACGACACCCAGTTCGTGAGGTTCGAC

AGCGACGCCGCGAGTCCGAGGACGGAGCCCCGGGCGCCATGGATAGAGCAGG

AGGGGCCGGAGTATTGGGACCGGAACACACAGATCTTCAAGACCAACACACAGA

CTTACCGAGAGAGCCTGCGGAACCTGCGCGGCTACTACAACCAGAGCGAGGCC

GGGTCTCACATCATCCAGAGGATGTATGGCTGCGACCTGGGGCCCGACGGGCG

CCTCCTCCGCGGGCATGACCAGTCCGCCTACGACGGCAAGGATTACATCGCCC

TGAACGAGGACCTGAGCTCCTGGACCGCGGCGGACACCGCGGCTCAGATCAC

CCAGCGCAAGTGGGAGGCGGCCCGTGTGGCGGAGCAGCTGAGAGCCTACCTG

GAGGGCCTGTGCGTGGAGTGGCTCCGCAGATACCTGGAGAACGGGAAGGAGA

CGCTGCAGCGCACAGATTCCCCAAAGGCCCATGTGACCCATCACAGCAGACCTG

AAGATAAAGTCACCCTGAGGTGCTGGGCCCTGGGCTTCTACCCTGCTGACATCA

CCCTGACCTGGCAGTTGAATGGGGAGGAGCTGATCCAGGACATGGAGCTTGTGG

AGACCAGGCCTGCAGGGGATGGAACCTTCCAGAAGTGGGCATCTGTGGTGGTG

CCTCTTGGGAAGGAGCAGTATTACACATGCCATGTGTACCATCAGGGGCTGCCT

GAGCCCCTCACCCTGAGATGGGAGCCGGCAGCCACCACCACCATCACCATTGA
```

SEQ ID NO. 16
```
MMRPIVLVLLFATSALAGSHSMRYFHTSVSRPGRGEPRFITVGYVDDTLFVRFDSDAT

ASPRTEPRAPWIEQEGPEYWDRNTQIFKTNTQTYRESLRNLRGYYNQSEAGSHIIQR

MYGCDVGPDGRLLRGHNEYAYDGKDYIALNEDLRSWTAADTAAQITQRKWEAARV

AEQLRAYLEGECVEWLRRYLENGKETLQRTDSPKAHVTHHSRPEDKVTLRCWALG

FYPADITLTWQLNGEELIQDMELVETRPAGDGTFQKWASVVVPLGKEQYYTCHVYH

QGLPEPLTLRWEPGSHHHHHH
```

SEQ ID NO. 17

ATGATGCGGCCCATCGTGCTGGTGCTGCTGTTTGCCACATCTGCCCTGGCCGGC
TCCCACTCCATGAGGTATTTCTACACCGCCATGTCCCGGCCCGGCCGCGGGGAG
CCCCGCTTCATCGCAGTGGGCTACGTGGACGACACCCAGTTCGTGAGGTTCGAC
AGCGACGCCGCGAGTCCGAGGACGGAGCCCCGGGCGCCATGGATAGAGCAGG
AGGGGCCGGAGTATTGGGACCGGAACACACAGATCTTCAAGACCAACACACAGA
CTTACCGAGAGAGCCTGCGGAACCTGCGCGGCTACTACAACCAGAGCGAGGCC
GGGTCTCACATCATCCAGAGGATGTATGGCTGCGACCTGGGGCCCGACGGGCG
CCTCCTCCGCGGGCATGACGAGTCCGCCTACGACGGCAAGGATTACATCGCCC
TGAACGAGGACCTGAGCTCCTGGACCGCGGCGGACACCGCGGCTCAGATCAC
CCAGCGCAAGTGGGAGGCGGCCCGTGTGGCGGAGCAGCTGAGAGCCTACCTG
GAGGGCCTGTGCGTGGAGTGGCTCCGCAGATACCTGGAGAACGGGAAGGAGA
CGCTGCAGCGCACAGATTCCCCAAAGGCCCATGTGACCCATCACAGCAGACCTG
AAGATAAAGTCACCCTGAGGTGCTGGGCCCTGGGCTTCTACCCTGCTGACATCA
CCCTGACCTGGCAGTTGAATGGGGAGGAGCTGATCCAGGACATGGAGCTTGTGG
AGACCAGGCCTGCAGGGATGGAACCTTCCAGAAGTGGGCATCTGTGGTGGTG
CCTCTTGGGAAGGAGCAGTATTACACATGCCATGTGTACCATCAGGGGCTGCCT
GAGCCCCTCACCCTGAGATGGGAGCCGGGCAGCCACCACCACCATCACCATTGA

SEQ ID NO. 18

MMRPIVLVLLFATSALAGSHSMRYFYTAMSRPGRGEPRFIAVGYVDDTQFVRFDSDA
ASPRTEPRAPWIEQEGPEYWDRNTQIFKTNTQTYRESLRNLRGYYNQSEAGSHIIQR
MYGCDLGPDGRLLRGHDESAYDGKDYIALNEDLSSWTAADTAAQITQRKWEAARV
AEQLRAYLEGLCVEWLRRYLENGKETLQ*RTDSPKAHVTHHSRPEDKVTLRCWALGF*
*YPADITLTWQLNGEELIQDMELVETRPAGDGTFQKWASVVVPLGKEQYYTCHVYHQ*
*GLPEPLTLRWEP***GS*HHHHHH*

40

Soluble B*07:02$^{Q115E}$-Kb, Nucleotide Sequence (SEQ ID NO. 19) and Amino Acid Sequence (SEQ ID NO. 20)
Sequences are listed in the following order:
Signal peptide derived from Fibroin-L (in regular Arial font below)
HLA-B*07:02 α1 domain (underlined below)

HLA-B*07:02 α2 domain with Q115E mutation (in bold below)
Mouse K$^b$ α3 domain (in italics below)
Flexible GS linker (in bold and underlined below)
6×His tag (in bold and italics below)

SEQ ID NO. 19

ATGATGCGGCCCATCGTGCTGGTGCTGCTGTTTGCCACATCTGCCCTGGCCGGC
AGCCACAGCATGCGGTACTTTTACACCAGCGTGTCCAGACCCGGCAGAGGCGAG
CCCAGATTCATCAGCGTGGGCTACGTGGACGACACCCAGTTCGTCAGATTCGAC
AGCGACGCCGCCAGCCCCAGAGAGGAACCTAGAGCCCCTTGGATCGAGCAGGA
AGGCCCCGAGTACTGGGACCGGAACACCCAGATCTACAAGGCCGAGGCCCAGA
CCGACAGAGAGCCTGAGAAACCTGCGGGGCTACTACAACCAGAGCGAGGCC
GGCTCTCACACCCTGCAGTCTATGTACGGCTGCGACGTGGGCCCCGATGGCAG
ACTGCTGAGACGCCACGATGAGTACGCCTACGACGGCAAGGACTATATCGCCC
TGAACGAGGACCTGCGGAGCTGGACAGCCGCCGATACAGCCGCCCAGATCAC
CCAGAGAAAGTGGGAGGCCGCCAGAGAGGCCGAACAGAGAAGGGCCTATCTG
GAAGGCGAGTGCGTGGAATGGCTGCGGAGATACCTGGAAAATGGCAAGGACA

-continued

AGCTGGAACGCACAGATTCCCCAAAGGCCCATGTGACCCATCACAGCAGACCTG

AAGATAAAGTCACCCTGAGGTGCTGGGCCCTGGGCTTCTACCCTGCTGACATGA

CCCTGACCTGGCAGTTGAATGGGGAGGAGCTGATCCAGGACATGGAGCTTGTGG

AGACCAGGCCTGCAGGGGATGGAACCTTCCAGAAGTGGGCATCTGTGGTGGTG

CCTCTTGGGAAGGAGCAGTATTACACATGCCATGTGTACCATCAGGGGCTGCCT

GAGCCCCTCACCCTGAGATGGGAGCCGGGCAGCCACCACCACCATCACCATTGA

SEQ ID NO. 20

MMRPIVLVLLFATSALA<u>GSHSMRYFYTSVSRPGRGEPRFISVGYVDDTQFVRFDSDA</u>

<u>ASPREEPRAPWIEQEGPEYWDRNTQIYKAQAQTDRESLRNLRGYYNQSEA</u>GSHTLQ

SMYGCDVGPDGRLLRGHDEYAYDGKDYIALNEDLRSWTAADTAAQITQRKWEAAR

EAEQRRAYLEGECVEWLRRYLENGKDKLER*TDSPKAHVTHMSRPEDKVTLRCWAL*

*GFYPADITLTWQLNGEELIQDMELVETRPAGDGTFQKWASVVVPLGKEQYYTCHVY*

*HQGLPEPLTLRWEP*<u>GS</u>*HHHHHH*

Soluble B*08:01$^{Q115E}$-Kb, Nucleotide Sequence (SEQ ID NO. 21) and Amino Acid Sequence (SEQ ID NO. 22)

Sequences are listed in the following order:

Signal peptide derived from Fibroin-L (in regular Arial font below)

HLA-B*08:01 α1 domain (underlined below)

HLA-B*08:01 α2 domain with Q115E mutation (in bold below)

Mouse K$^b$ α3 domain (in italics below)

Flexible GS linker (in bold and underlined below)

6×His tag (in bold and italics below)

SEQ ID NO. 21

ATGATGCGGCCCATCGTGCTGGTGCTGCTGTTTGCCACATCTGCCCTGGCCGG<u>C</u>

<u>AGCCACAGCATGCGGTACTTTGACACCGCCATGAGCAGACCCGGCAGAGGCGA</u>

<u>GCCCAGATTCATCAGCGTGGGCTACGTGGACGACACCCAGTTCGTCAGATTCGA</u>

<u>CAGCGACGCCGCCAGCCCCAGAGAGGAACCTAGAGCCCCTTGGATCGAGCAGG</u>

<u>AAGGCCCCGAGTACTGGGACCGGAACACCCAGATCTTCAAGACCAATACCCAGA</u>

<u>CCGACAGAGAGAGCCTGCGGAACCTGCGGGGCTACTACAATCAGAGCGAGGCC</u>

GGCTCTCACACCCTGCAGTCTATGTACGGCTGCGACGTGGGCCCCGATGGCAG

ACTGCTGAGAGGCCACAACGAGTACGCCTACGACGGCAAGGACTATATCGCCC

TGAACGAGGACCTGCGGAGCTGGACAGCCGCCGATACAGCCGCCCAGATCAC

CCAGAGAAAGTGGGAGGCCGCCAGAGTGGCCGAGCAGGATAGAGCCTACCTG

GAAGGCACCTGTGTGGAATGGCTGCGGAGATACCTGGAAAATGGCAAGGACA

CCCTGGAA*CGCACAGATTCCCCAAAGGCCCATGTGACCCATCACAGCAGACCTG*

*AAGATAAAGTCACCCTGAGGTGCTGGGCCCTGGCTTCTACCCTGCTGACATCA*

*CCCTGACCTGGCAGTTGAATGGGAGGAGCTGATCCAGGACATGGAGCTTGTGG*

*AGACCAGGCCTGCAGGGGATGGAACCTTCCAGAAGTGGCCATCTGTGGTGGTG*

*CCTCTTGGGAAGGAGCAGTATTACACATGCCATGTGTACCATCAGGGGCTGCCT*

*GAGCCCCTCACCCTGAGATGGGAGCCG*<u>GGCAGC</u>*CACCACCACCATCACCAT*TGA

SEQ ID NO. 22

MMRPIVLVLLFATSALA<u>GSHSMRYFDTAMSRPGRGEPRFISVGYVDDTQFVRFDSDA</u>

<u>ASPREEPRAPWIEQEGPEYVVDRNTQIFKINTQTDRESLRNLRGYYNQSEA</u>GSHTLQ

SMYGCDVGPDGRLLRGHNEYAYDGKDYIALNEDLRSWTAADTAAQITQRKWEAAR

VAEQDRAYLEGTCVEWLRRYLENGKDTLER*TDSPKAHVTHHSRPEDKVTLRCWAL*

-continued

GFYPADITLTWQLNGEELIQDMELVETRPAGDGTFQKWASVVVPLGKEQYYTCHVY

HQGLPEPLTLRWEP<u>GSHHHHHH</u>

Soluble C*05:01$^{Q115E}$-Kb, Nucleotide Sequence (SEQ ID NO. 23) and Amino Acid Sequence (SEQ ID NO. 24)
Sequences are listed in the following order:
Signal peptide derived from Fibroin-L (in regular Arial font below)
HLA-C*05:01 α1 domain (underlined below)
HLA-C*05:01 α2 domain with Q115E mutation (in bold below)
Mouse K$^b$ α3 domain (in italics below)
Flexible GS linker (in bold and underlined below)
6×His tag (in bold and italics below)

Soluble C*07:01$^{Q115E}$-Kb, Nucleotide Sequence (SEQ ID NO. 25) and Amino Acid Sequence (SEQ ID NO. 26)
Sequences are listed in the following order:
Signal peptide derived from Fibroin-L (in regular Arial font below)
HLA-C*07:01 α1 domain (underlined below)
HLA-C*07:01 α2 domain with Q115E mutation (in bold below)
Mouse K$^b$ α3 domain (in italics below)
Flexible GS linker (in bold and underlined below)
6×His tag (in bold and italics below)

SEQ ID NO. 23

ATGATGCGGCCCATCGTGCTGGTGCTGCTGTTTGCCACAAGCGCCCTGGCC<u>TGC</u>

<u>TCTCACAGCATGCGCTATTTTTACACGGCAGTTAGTCGGCCTGGGAGGGGTGAG</u>

<u>CCGAGATTCATTGCTGTAGGCTACGTAGACGACACTCAATTTGTACAGTTCGACT</u>

<u>CAGACGCTGCTTCACCGCGAGGAGAGCCCAGGGCACCCTGGGTAGAACAAGAA</u>

<u>GGGCCCGAATACTGGGATCGAGAAACCCAGAAGTATAAGAGGCAAGCACAAACT</u>

<u>GATCGGGTCAACTTGAGAAAACTGCGAGGCTACTATAATCAAAGTGAGGCA</u>GGAT

CCCATACACTTCAGAGGATGTATGGCTGCGACCTTGGTCCAGATGGCCGGCTC

CTCAGAGGGTATAACGAATTTGCATACGACGGGAAGGATTACATAGCTCTCAAT

GAGGACCTTAGATCATGGACGGCAGCGGATAAGGCAGCCCAAATTACTCAAAG

GAAATGGGAGGCGGCCCGAGAAGCAGAGCAGAGAAGAGCCTACCTGGAAGGT

ACATGCGTGGAGTGGCTTCGGCGCTATCTCGAAAACGGTAAAAAGACATTGCA

ACGCACAGATTCCCCAAAGGCCCATGTGACCCATCACAGCAGACCTGAAGATAA

AGTCACCCTGAGGTGCTGGGGCCTGGGCTTCTACCCTGCTGACATCACCCTGAC

CTGGCAGTTGAATGGGAGGAGGTGATCCAGGACATGGAGCTTGTGGAGACCAG

GCCTGCAGGGATGGAACCTTCCAGAAGTGGGCATCTGTGGTGGTGCCTCTTGG

GAAGGAGCAGTATTACACATGCCATGTGTACCATCAGGGGCTGCCTGAGCCCCT

CACCCTGAGATGGGAGCCG<u>GGCAGC</u>CACCACCACCATCACCATTGA

SEQ ID NO. 24

MMRPIVLVLLFATSALA<u>CSHSMRYFYTAVSRPGRGEPRFIAVGYVDDTQFVQFDSDA</u>

<u>ASPRGEPRAPWVEQEGPEYWDRETQKYKRQAQTDRVNLRKLRGYYNQSEA</u>GSHT

LQRMYGCDLGPDGRLLRGYNEFAYDGKDYIALNEDLRSWTAADKAAQITQRKWEA

AREAEQRRAYLEGTCVEWLRRYLENGKKTLQRTDSPKAHVTHHSRPEDKVTLRCW

ALGFYPADITLTWQLNGEELIQDMELVETRPAGDGTFQKWASVVVPLGKEQYYTCHV

YHQGLPEPLTLRWEP<u>GSHHHHHH</u>

SEQ ID NO. 25

ATGATGCGGCCCATCGTGCTGGTGCTGCTGTTTGCCACAAGCGCCCTGGCCTGC

AGCCACAGCATGCGGTACTTTGACACCGCCGTGTCCAGACCCGGAAGAGGCGA

GCCCAGATTCATCAGCGTGGGCTACGTGGACGACACCGAGTTCGTCAGATTCGA

CAGCGACGCCGCCAGCCCCAGAGGCGAACCTAGAGCACCTTGGGTGGAACAGG

AAGGCCCCGAGTACTGGGACAGAGAGACACAGAACTACAAGGGGCAGGCCCAG

GCCGACAGAGTGTCCCTGAGAAACCTGCGGGGCTACTACAACCAGAGCGAGGA

CGGCAGCCACACCCTGCAGAGAATGTACGGCTGTGACCTGGGCCCCGATGGC

AGACTGCTGAGAGGCTACGATGAGAGCGCCTACGACGGCAAGGACTATATCGC

CCTGAACGAGGACCTGCGGAGCTGGACAGCCGCCGATACAGCCGCCCAGATC

ACCCAGAGAAAACTGGAAGCCGCCAGAGCCGCCGAGCAGCTGAGAGCTTATC

TGGAAGGCACCTGTGTGGAATGGCTGCGGAGATACCTGGAAAACGGCAAAGA

GACACTGCAG*CGCACAGATTCCCCAAAGGCCCATGTGACCCATCACAGCAGACC*

*TGAAGATAAAGTCACCCTGAGGTGCTGGGCCCTGGGCTTCTACCCTGCTGACAT*

*CACCCTGACCTGGCAGTTGAATGGGGAGGAGCTGATCCAGGACATGGAGCTTGT*

*GGAGACCAGGCCTGCAGGGGATGGAACCTTCCAGAAGTGGGCATCTGTGGTGG*

*TGCCTCTTGGGAAGGAGCAGTATTACACATGCCATGTGTACCATCAGGGGCTGC*

*CTGAGCCCCTCACCCTGAGATGGGAGCCGGG*CAGCCACCACCACCATCACCAT

TGA

SEQ ID NO. 26

MMRPIVLVLLFATSALACSHSMRYFDTAVSRPGRGEPRFISVGYVDDTQFVRFDSDA

ASPRGEPRAPWVEQGPEYWDRETQNYKRQAQADRVSLRNLRGYYNQSEDGSHT

LQRMYGCDLGPDGRLLRGYDESAYDGKDYIALNEDLRSWTAADTAAQITQRKLEA

ARAAEQLRAYLEGTCVEWLRRYLENGKETLQ*RTDSPKAHVTHHSRPEDKVTLRCW*

*ALGFYPADITLTWQLNGEELIQDMELVETRPAGDGTFQKWASVVVPLGKEQYYTCHV*

*YHQGLPEPLTLRWEP*GSHHHHHH*

Soluble C*07:02$^{Q115E}$-Kb, Nucleotide Sequence (SEQ ID NO. 27) and Amino Acid Sequence (SEQ ID NO. 28)
Sequences are listed in the following order:
Signal peptide derived from Fibroin-L (in regular Arial font below)
HLA-C*07:02 α1 domain (underlined below)

HLA-C*07:02 α2 domain with Q115E mutation (in bold below)
Mouse K$^b$ α3 domain (in italics below)
Flexible GS linker (in bold and underlined below)
6×His tag (in bold and italics below)

SEQ ID NO. 27

ATGATGCGGCCCATCGTGCTGGTGCTGCTGTTTGCCACATCTGCCCTGGCCTGC

AGCCACAGCATGCGGTACTTTACACCGCCGTGTCCAGACCCGGAAGAGGCGA

GCCCAGATTCATCAGCGTGGGCTACGTGGACGACACCAGTTCGTCAGATTCGA

CAGCGACGCCGCCAGCCCCAGAGGCGAACCTAGAGCACCTTGGGTGGAACAGG

AAGGCCCGGAGTACTGGGACAGAGAGACACAGAAGTACAAGCGGCAGGCCCAG

GCCGACAGAGTGTCCCTGAGAAACCTGCGGGGCTACTACAACCAGAGCGAGGA

CGGCAGCCACACCCTGCAGAGAATGAGCGGCTGTGACCTGGGCCCCGATGGC

AGACTGCTGAGAGGCTACGATGAGAGCGCCTACGACGGCAAGGACTATATCGC

CCTGAACGAGGACCTGCGGAGCTGGACAGCCGCCGATACAGCCGCCCAGATC

ACCCAGAGAAAACTGGAAGCCGCCAGAGCCGCCGAGCAGCTGAGAGCTTATC

-continued

TGGAAGGCACCTGTGTGGAATGGCTGCGGAGATACCTGGAAAACGGCAAAGA

GACACTGCAGCGCACAGATTCCCCAAAGGCCCATGTGACCCATCACAGCAGACC

TGAAGATAAAGTCACCCTGAGGTGCTGGGCCCTGGGCTTCTACCCTGCTGACAT

CACCCTGACCTGGCAGTTGAATGGGGAGGAGCTGATCCAGGACATGGAGCTTGT

GGAGACCAGGCCTGCAGGGGATGGAACCTTCCAGAAGTGGGCATCTGTGGTGG

TGCCTCTTGGGAAGGAGCAGTATTACACATGCCATGTGTACCATCAGGGGCTGC

CTGAGCCCCTCACCCTGAGATGGGAGCCGGGCAGCCACCACCACCATCACCATTGA

SEQ ID NO. 28

MMRPIVLVLLFATSALA<u>CSHSMRYFDTAVSRPGRGEPRFISVGYVDDTQFVRFDSDA</u>

<u>ASPRGEPRAPWVEQEGPEYWDRETQKYKRQAQADRVSLRNLRGYYNQSED</u>GSHT

LQRMSGCDLGPDGRLLRGYDESAYDGKDYIALNEDLRSWTAADTAAQITQRKLEA

ARAAEQLRAYLEGTCVEWLRRYLENGKETLQ*RTDSPKAHVTHHSRPEDKVTLRCW*

*ALGFYPADITLTWQLNGEELIQDMELVETRPAGDGTFQKWASVVVPLGKEQYYTCHV*

*YHQGLPEPLTLRWEP*GS_HHHHHH_Z

Soluble C*16:01$^{Q115E}$-K$^b$, Nucleotide Sequence (SEQ ID NO. 29) and Amino Acid Sequence (SEQ ID NO. 30)

Sequences are listed in the following order:
Signal peptide derived from Fibroin-L (in regular Arial font below)
HLA-C*16:01 α1 domain (underlined below)
HLA-C*16:01 α2 domain with Q115E mutation (in bold below)
Mouse K$^b$ α3 domain (in italics below)
Flexible GS linker (in bold and underlined below)
6×His tag (in bold and italics below)

SEQ ID NO. 29

ATGATGAGGCCCATCGTGCTGGTGCTGCTGTTCGCCACATCTGCCCTGGCC<u>TGC</u>

<u>AGCCACAGCATGCGGTACTTTTACACCGCCGTGTCCAGACCCGGCAGAGGCGAG</u>

<u>CCTAGATTCATTGCCGTGGGCTACGTGGACGACACCCAGTTCGTCAGATTCGACA</u>

<u>GCGACGCCGCCAGCCCCAGAGGGGAACCTAGAGCACCTTGGGTGGAACAGGAA</u>

<u>GGCCCCGAGTACTGGGACAGAGAGACACAGAAGTACAAGCGGCAGGCCCAGAC</u>

<u>CGACCGGGTGTCCCTGAGAAACCTGCGGGGCTACTACAACCAGAGCGAGGCC</u>G

GCTCTCACACCCTGCAGTGGATGTACGGCTGCGACCTGGGCCCTGATGGCAGA

CTGCTGAGAGGCTACGACGAGTCCGCCTACGACGGCAAGGACTATATCGCCGT

GAACGAGGACCTGCGGAGCTGGACAGCCGCCGATACAGCCGCCCAGATCACC

CAGAGAAAGTGGGAAGCCGCCAGAGCCGCCGAGCAGCAGAGAGCTTATCTGG

AAGGCACCTGTGTGGAATGGCTGCGGAGATACCTGGAAAACGGCAAAGAGAC

ACTGCAGCGCACAGATTCCCCAAAGGCCCATGTGACCCATGACAGCAGACCTGA

AGATAAAGTCACCCTGAGGTGCTGGGCGCTGGGCTTCTACCCTGCTGACATCAC

CCTGACCTGGCAGTTGAATGGGGAGGAGCTGATCCAGGAGATGGAGCTTGTGGA

GACCAGGCCTGCAGGGGATGGAACCTTCCAGAAGTGGGCATCTGTGGTGGTGC

CTCTTGGGAAGGAGCAGTATTACACATGCCATGTGTACCATCAGGGGCTGCCTG

AGCCCCTCACCCTGAGATGGGAGCC<u>GGCAGC</u>CACCACCACCATCACCATTGA

SEQ ID NO. 30

MMRPIVLVLLFATSALA<u>CSHSMRYFYTAVSRPGRGEPRFIAVGYVDDTQFVRFDSDA</u>

<u>ASPRGEPRAPWVEQEGPEYWDRETQKYKRQAQTDRVSLRNLRGYYNQSEA</u>GSHT

LQWMYGCDLGPDGRLLRGYDESAYDGKDYIALNEDLRSWTAADTAAQITQRKWE

AARAAEQQRAYLEGTCVEWLRRYLENGKETLQ*RTDSPKAHVTHHSRPEDKVTLRC*

-continued
```
WALGFYPADITLTWQLNGEELIQDMELVETRPAGDGTFQKWASVVVPLGKEQYYTC

HVYHQGLPEPLTLRWEPGSHHHHHHZ
```

As with the sequences noted above, the present application may similarly be directed to the following sequences:

Soluble B*35:01-Wt, Nucleotide Sequence (SEQ ID NO.31) and Amino Acid Sequence (SEQ ID NO.32)

Sequences are listed in the following order:

Signal peptide derived from Fibroin-L (in regular Arial font below)

HLA-B*35:01 α1 domain (underlined below)
HLA-B*35:01 α2 domain (in bold below)
HLA-B*35:01 α3 domain (in italics below)
Flexible GS linker (in bold and underlined below)
6×His tag (in bold and italics below)

```
                                          SEQ ID NO. 31
ATGATGCGCCCATCGTGCTGGTGCTGCTGTTTGCCACATCTGCCCTGGCCGGC

TCCCACTCCATGAGGTATTTCTACACCGCCATGTCCCGGCCCGGCCGCGGGAG

CCCCGCTTCATCGCAGTGGGCTACGTGGACGACACCCAGTTCGTGAGGTTCGAC

AGCGACGCCGCGAGTCCGAGGACGGAGCCCCGGGCGCCATGGATAGAGCAGG

AGGGGCCGGAGTATTGGGACCGGAACACACAGATCTTCAAGACCAACACACAGA

CTTACCGAGAGAGCCTGCGGAACCTGCGCGGCTACTACAACCAGAGCGAGGCC

GGGTCTCACATCATCCAGAGGATGTATGGCTGCGACCTGGGCCCCGACGGGCG

CCTCCTCCGCGGGCATGACCAGTCCGCCTACGACGGCAAGGATTACATCGCCC

TGAACGAGGACCTGAGCTCCTGGACCGCGGCGGACACCGCGGCTCAGATCAC

CCAGCGCAAGTGGGAGGCGGCCCGTGTGGCGGAGCAGCTGAGAGCCTACCTG

GAGGGCCTGTGCGTGGAGTGGCTCCGCAGATACCTGGAGAACGGGAAGGAGA

CGCTGCAGCGCGCGGACCCCCCAAAGACACACGTGACCCACCACCCCGTCTCT

GACCATGAGGCCACCCTGAGGTGCTGGGCCCTGGGCTTCTACCCTGCGGAGAT

CACACTGACCTGGCAGCGGGATGGCGAGGACCAAACTCAGGACACTGAGCTTGT

GGTCTGGAGAAGAGCAGAGATACACATGCCATGTAGAGCATGAGGGGCTGCC

CAAGCCCCTCACCCTGAGATGGGAGCCGGGCAGCCACCACCACCATCACCATTGA

SEQ ID NO. 32
MMRPIVLVLLFATSALAGSHSMRYFYTAMSRPGRGEPRFIAVGYVDDTQFVRFDSDA

ASPRTEPRAPWIEQEGPEYWDRNTQIFKTNTQTYRESLRNLRGYYNQSEAGSHIIQR

MYGCDLGPDGRLLRGHDQSAYDGKDYIALNEDLSSWTAADTAAQITQRKWEAARV

AEQLRAYLEGLCVEWLRRYLENGKETLQRADPPKTHVTHHPVSDHEATLRCWALG

FYPAEITLTWQRDGEDQTQDTELVETRPAGDRTFQKWAAVVVPSGEEQRYTCHVQH

EGLPKPLTLRWEPGSHHHHHHZ
```

Soluble B*35:01-Kb, Nucleotide Sequence (SEQ ID NO.33) and Amino Acid Sequence (SEQ ID NO.34)

Sequences are listed in the following order:

Signal peptide derived from Fibroin-L (in regular Arial font below)

HLA-B*35:01 α1 domain (underlined below)
HLA-B*35:01 α2 domain (in bold below)
Mouse K$^b$ α3 domain (in italics below)
Flexible GS linker (in bold and underlined below)
6×His tag (in bold and italics below)

SEQ ID NO. 33

ATGATGCGGCCCATCGTGCTGGTGCTGCTGTTTGCCACATCTGCCCTGGCCGGC

TCCCACTCCATGAGGTATTTCTACACCGCCATGTCCCGGCCCGGCCGCGGGGAG

CCCCGCTTCATCGCAGTGGGCTACGTGGACGACACCCAGTTCGTGAGGTTCGAC

AGCGACGCCGCGAGTCCGAGGACGGAGCCCCGGGCGCCATGGATAGAGCAGG

AGGGGCCGGAGTATTGGGACCGGAACACACAGATCTTCAAGACCAACACAGA

CTTACCGAGAGAGGCTGGGGAACCTGCGCGGCTACTACAACCAGACCGAGGCC

GGGTCTCACATCATCCAGAGGATGTATGGCTGCGACCTGGGGCCCGAGGGGCG

CCTCCTCCGCGGGCATGACCAGTCCGCCTACGACGGCAAGGATTACATCGCCC

TGAACGAGGACCTGAGCTCCTGGACCGCGGCGGACACCGCGGCTCAGATCAC

CCAGCGCAAGTGGGAGGCGGCCCGTGTGGCGGAGCAGCTGAGAGCCTACCTG

GAGGGCCTGTGCGTGGAGTGGCTCCGCAGATACCTGGAGAACGGGAAGGAGA

CGCTGCAGCGCACAGATTCCCCAAAGGCCCATGTGACCCATGACAGCAGAGCTG

AAGATAAAGTCACCCTGAGGTGCTGGGCCCTGGGCTTCTACCCTGCTGACATCA

CCCTGACCTGGCAGTTGAATGGGGAGGAGCTGATCCAGGACATGGAGCTTGTGG

AGACCAGGCCTGCAGGGGATGGAACCTTCCAGAAGTGGGCATCTGTGGTGGTG

CCTCTTGGGAAGGAGCAGTATTACACATGCCATGTGTACCATCAGGGGCTGCCT

GAGCCCCTCACCCTGAGATGGGAGCCGGGCAGCCACCACCACCATCACCATTGA

SEQ ID NO. 34

MMRPIVLVLLFATSALAGSHSMRYFYTAMSRPGRGEPRFIAVGYVDDTQFVRFDSDA

ASPRTEPRAPWIEQEGPEYWDRNTQIFKTNTQTYRESLNLRGYYNQSEAGSHIIQR

MYGCDLGPDGRLLRGHDQSAYDGKDYIALNEDLSSWTAADTAAQITQRKWEAARV

AEQLRAYLEGLCVEWLRRYLENGKLTLQRTDSPKAHVTHHSRPEDKVTLRCWALG

FYPADITLTWQLNGEELIQDMELVETRPAGDGTFQKWASVVVPLGKEQYYTCHVYH

QGLPEPLTLRWEPGSHHHHHH*

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCES

1. Wooldridge L, Lissina A, Cole D K, van den Berg H A, Price D A, Sewell A K. Tricks with tetramers: how to get the most from multimeric peptide-MHC. *Immunology*. 2009; 126(2): 147-164.
2. Dolton G, Tungatt K, Lloyd A, Bianchi V, Theaker S M, Trimby A, Holland C J, Donia M, Godkin A J, Cole D K, Straten P T, Peakman M, Svane I M, Sewell A K. More tricks with tetramers: a practical guide to staining T cells with peptide-MHC multimers. *Immunology*. 2015; 146 (1):11-22.
3. Rossjohn J, Gras S, Miles J J, Turner S J, Godfrey D I, McCluskey J. T cell antigen receptor recognition of antigen-presenting molecules. *Annu Rev Immunol*. 2015; 33:169-200.
4. Marrack P, Scott-Browne J P, Dai S, Gapin L, Kappler J W. Evolutionarily conserved amino acids that control TCR-MHC interaction. *Annu Rev Immunol*. 2008; 26:171-203.
5. Altman J D, Moss P A, Goulder P J, Barouch D H, McHeyzer-Williams M G, Bell J I, McMichael A J, Davis M M. Phenotypic analysis of antigen-specific T lymphocytes. *Science*. 1996; 274(5284):94-96.
6. Klenerman P, Cerundolo V, Dunbar P R. Tracking T cells with tetramers: new tales from new tools. *Nat Rev Immunol*. 2002; 2(4):263-272.
7. Janeway C. Immunobiology: the immune system in health and disease (ed 6th). New York: Garland Science; 2005.
8. Migueles S A, Sabbaghian M S, Shupert W L, Bettinotti M P, Marincola F M, Martino L, Hallahan C W, Selig S M, Schwartz D, Sullivan J, Connors M. HLA B*5701 is highly associated with restriction of virus replication in a subgroup of HIV-infected long term nonprogressors. *Proc Natl Acad Sci USA*. 2000; 97(6):2709-2714.
9. Kawase T, Akatsuka Y, Torikai H, Morishima S, Oka A, Tsujimura A, Miyazaki M, Tsujimura K, Miyamura K, Ogawa S, Inoko H, Morishima Y, Kodera Y, Kuzushima K, Takahashi T. Alternative splicing due to an intronic SNP in HMSD generates a novel minor histocompatibility antigen. *Blood*. 2007; 110(3):1055-1063.
10. Rodenko B, Toebes M, Hadrup S R, van Esch W J, Molenaar A M, Schumacher T N, Ovaa H. Generation of peptide-MHC class I complexes through UV-mediated ligand exchange. *Nat Protoc*. 2006; 1(3):1120-1132.
11. Bakker A H, Hoppes R, Linnemann C, Toebes M, Rodenko B, Berkers C R, Hadrup S R, van Esch W J, Heemskerk M H, Ovaa H, Schumacher T N. Conditional MHC class I ligands and peptide exchange technology for the human MHC gene products HLA-A1, -A3, -A11, and -B7. *Proc Natl Acad Sci USA.* 2008; 105(10):3825-3830.
12. Saini S K, Schuster H, Ramnarayan V R, Rammensee H G, Stevanovic S, Springer S. Dipeptides catalyze rapid peptide exchange on MHC class I molecules. *Proc Natl Acad Sci USA.* 2015; 112(1):202-207.
13. Laugel B, van den Berg H A, Gostick E, Cole D K, Wooldridge L, Boulter J, Milicic A, Price D A, Sewell A K. Different T cell receptor affinity thresholds and CD8 coreceptor dependence govern cytotoxic T lymphocyte activation and tetramer binding properties. *J Biol Chem.* 2007; 282(33):23799-23810.
14. Nguyen L T, Yen P H, Nie J, Liadis N, Ghazarian D, Al-Habeeb A, Easson A, Leong W, Lipa J, McCready D, Reedijk M, Hogg D, Joshua A M, Quirt I, Messner H, Shaw P, Crump M, Sharon E, Ohashi P S. Expansion and characterization of human melanoma tumor-infiltrating lymphocytes (TILs). *PLoS One.* 2010; 5(11):e13940.
15. Kagoya Y, Nakatsugawa M, Yamashita Y, Ochi T, Guo T, Anczurowski M, Saso K, Butler M O, Arrowsmith C H, Hirano N. BET bromodomain inhibition enhances T cell persistence and function in adoptive immunotherapy models. *J Clin Invest.* 2016; 126(9):3479-3494.
16. Hirano N, Butler M O, Xia Z, Ansen S, von Bergwelt-Baildon M S, Neuberg D, Freeman G J, Nadler L M. Engagement of CD83 ligand induces prolonged expansion of CD8+ T cells and preferential enrichment for antigen specificity. *Blood.* 2006; 107(4):1528-1536.
17. Butler M O, Lee J S, Ansen S, Neuberg D, Hodi F S, Murray A P, Drury L, Berezovskaya A, Mulligan R C, Nadler L M, Hirano N. Long-lived antitumor CD8+ lymphocytes for adoptive therapy generated using an artificial antigen-presenting cell. *Clin Cancer Res.* 2007; 13(6):1857-1867.
18. Hirano N, Butler M O, Xia Z, Berezovskaya A, Murray A P, Ansen S, Kojima S, Nadler L M. Identification of an immunogenic CD8+ T-cell epitope derived from gamma-globin, a putative tumor-associated antigen for juvenile myelomonocytic leukemia. *Blood.* 2006; 108(8):2662-2668.
19. Imataki O, Ansen S, Tanaka M, Butler M O, Berezovskaya A, Milstein M I, Kuzushima K, Nadler L M, Hirano N. IL-21 can supplement suboptimal Lck-independent MAPK activation in a STAT-3-dependent manner in human CD8(+) T cells. *J Immunol.* 2012; 188(4):1609-1619.
20. Butler M O, Ansen S, Tanaka M, Imataki O, Berezovskaya A, Mooney M M, Metzler G, Milstein M I, Nadler L M, Hirano N. A panel of human cell-based artificial APC enables the expansion of long-lived antigen-specific CD4+ T cells restricted by prevalent HLA-D R alleles. *Int Immunol.* 2010; 22(11):863-873.
21. Wooldridge L, Clement M, Lissina A, Edwards E S, Ladell K, Ekeruche J, Hewitt R E, Laugel B, Gostick E, Cole D K, Debets R, Berrevoets C, Miles J J, Burrows S R, Price D A, Sewell A K. MHC class I molecules with Superenhanced CD8 binding properties bypass the requirement for cognate TCR recognition and nonspecifically activate CTLs. *J Immunol.* 2010; 184(7):3357-3366.
22. Wooldridge L, Lissina A, Vernazza J, Gostick E, Laugel B, Hutchinson S L, Mirza F, Dunbar P R, Boulter J M, Glick M, Cerundolo V, van den Berg H A, Price D A, Sewell A K. Enhanced immunogenicity of CTL antigens through mutation of the CD8 binding MHC class I invariant region. *Eur J Immunol.* 2007; 37(5):1323-1333.
23. Hirano N, Butler M O, Von Bergwelt-Baildon M S, Maecker B, Schultze J L, O'Connor K C, Schur P H, Kojima S, Guinan E C, Nadler L M. Autoantibodies frequently detected in patients with aplastic anemia. *Blood.* 2003; 102(13):4567-4575.
24. Hirano N, Butler M O, Xia Z, Berezovskaya A, Murray A P, Ansen S, Nadler L M. Efficient presentation of naturally processed HLA class I peptides by artificial antigen-presenting cells for the generation of effective antitumor responses. *Clin Cancer Res.* 2006; 12(10): 2967-2975.
25. Tanaka M, Butler M O, Ansen S, Imataki O, Berezovskaya A, Nadler L M, Hirano N. Induction of HLA-DP4-restricted anti-survivin Th1 and Th2 responses using an artificial antigen-presenting cell. *Clin Cancer Res.* 2011; 17(16):5392-5401.
26. Ochi T, Nakatsugawa M, Chamoto K, Tanaka S, Yamashita Y, Guo T, Fujiwara H, Yasukawa M, Butler M O, Hirano N. Optimization of T-cell Reactivity by Exploiting TCR Chain Centricity for the Purpose of Safe and Effective Antitumor TCR Gene Therapy. *Cancer Immunol Res.* 2015; 3(9):1070-1081.
27. Nakatsugawa M, Yamashita Y, Ochi T, Tanaka S, Chamoto K, Guo T, Butler M O, Hirano N. Specific roles of each TCR hemichain in generating functional chain-centric TCR. *J Immunol.* 2015; 194(7):3487-3500.
28. Feldman S A, Assadipour Y, Kriley I, Goff S L, Rosenberg S A. Adoptive Cell Therapy—Tumor-Infiltrating Lymphocytes, T-Cell Receptors, and Chimeric Antigen Receptors. *Semin Oncol.* 2015; 42(4):626-639.
29. Robbins P F, Lu Y C, E I-Gamil M, Li Y F, Gross C, Gartner J, Lin J C, Teer J K, Cliften P, Tycksen E, Samuels Y, Rosenberg S A. Mining exomic sequencing data to identify mutated antigens recognized by adoptively transferred tumor-reactive T cells. *Nat Med.* 2013; 19(6):747-752.
30. Parker K C, Bednarek M A, Coligan J E. Scheme for ranking potential HLA-A2 binding peptides based on independent binding of individual peptide side-chains. *J Immunol.* 1994; 152(1): 163-175.

The invention claimed is:

1. A method of producing an HLA class I molecule complexed to a pre-selected peptide comprising
incubating, in vitro, a mammalian derived soluble HLA class I molecule complexed to an existing peptide with the pre-selected peptide,
wherein the pre-selected peptide is at a concentration sufficient to replace the existing peptide to produce the soluble HLA class I molecule complexed to the pre-selected peptide; and
wherein the soluble HLA class I molecule comprises α1, α2, α3 and β2m domains, and wherein:
(a) the soluble HLA class I molecule is HLA-A and comprises the α1, α2 and α3 domains of any of SEQ ID NOs. 2, 4, 6, 8, 10, and 12;
(b) the soluble HLA class I molecule is HLA-B and comprises the α1, α2 and α3 domains of any of SEQ ID NOs. 14, 16, 18, 20, and 22;
(c) the soluble HLA class I molecule is HLA-C and comprises the α1, α2 and α3 domains of any of SEQ ID NOs. 24, 26, 28, and 30; or
(d) the soluble HLA class I molecule comprises the amino acid sequence set forth in SEQ ID NO. 2, 4, 6, 8, 10, 12, 14, 16, 18, 20, 22, 24, 26, 28, or 30 with a β2m domain.

2. The method of claim 1, wherein the soluble HLA class I molecule complexed to the existing peptide is produced by a mammalian cell transfected with a soluble HLA class I molecule, wherein the β2m domain may be endogenous or exogenous, preferably exogenous and encoded on a second vector.

3. The method of claim 2, wherein the soluble HLA class I molecule comprises a signal peptide directing secretion of the HLA class I molecule outside of the mammalian cell.

4. The method of claim 3, wherein the soluble HLA class I molecule complexed to the existing peptide is provided in the supernatant of a culture of the mammalian cells.

5. The method of claim 1, wherein the soluble HLA class I molecule is HLA-A and comprises the α1, α2 and α3 domains of any of SEQ ID NOs. 2, 4, 6, 8, 10, and 12.

6. The method of claim 1, wherein the soluble HLA class I molecule is HLA-B and comprises the α1, α2 and α3 domains of any of SEQ ID NOs. 14, 16, 18, 20, and 22.

7. The method of claim 1, wherein the soluble HLA class I molecule is HLA-C and comprises the α1, α2 and α3 domains of any of SEQ ID NOs. 24, 26, 28, and 30.

8. The method of claim 1, wherein the α2 domain of the soluble HLA class I molecule comprises a Glu at position 115.

9. The method of claim 1, wherein the soluble HLA class I molecule comprises the amino acid sequence set forth in SEQ ID NO. 2, 4, 6, 8, 10, 12, 14, 16, 18, 20, 22, 24, 26, 28, or 30 with a β2m domain.

10. The method of claim 1, further comprising multimerizing the soluble HLA class I molecules, preferably into one of dimers, trimers, tetramers and pentamers.

11. The method of claim 10, wherein the soluble HLA class I molecules are dimerized using an antibody that recognizes a tag on the soluble HLA class I molecule.

12. The method of claim 11, wherein the tag comprises a 6×His tag linked to the C' end of the α3 domain, preferably connected by a flexible linker.

13. The method of claim 1, wherein the pre-selected peptide comprises a portion of A polypeptide selected from the group consisting of a WT1 polypeptide, a MIA polypeptide, an ALX1 polypeptide, a GAPDHS polypeptide, an S100B polypeptide, an ABCB5 polypeptide, an EXTL1 polypeptide, a CPN1 polypeptide, a TSPAN10 polypeptide, a GJB1 polypeptide, an MITF polypeptide, a DUSP4 polypeptide, a cyclin-A1 polypeptide, an HERV-K-MEL polypeptide, an LAGE-1 polypeptide, a MAGE polypeptide, an LAGE-2 polypeptide, an SSX-2 polypeptide, an XAGE-1b polypeptide, a CEA polypeptide, a gp100 polypeptide, an NY-BR-1 polypeptide, a TRP-2 polypeptide, a tyrosinase polypeptide, a CD274 polypeptide, a CPSF polypeptide, a cyclin D1 polypeptide, an IDO1 polypeptide, an mdm-2 polypeptide, a p53 polypeptide, a PRAME polypeptide, a SOX10 polypeptide, a survivin polypeptide, a telomerase polypeptide, a wild-type MART1 polypeptide, a heteroclitic MART1 polypeptide, a wild-type NY-ESO-1 polypeptide, a heteroclitic NY-ESO-1 polypeptide, an HIV pol polypeptide, and an HTLV-1 tax polypeptide.

14. The method of claim 1, wherein the pre-selected peptide comprises an amino acid sequence selected from the amino acid sequences set forth in SEQ ID NOs: 35-122.

15. A method of screening a population of T-cells for an antigen-specific TCR that recognizes a pre-selected peptide antigen, comprising producing a mammalian-derived soluble HLA class I molecule complexed to the pre-selected peptides according to claim 1; and screening the population of T-cells for antigen-specific T-cells that bind the mammalian-derived HLA class I molecule complexed to the pre-selected peptides.

16. A method of treating a disease or condition in a subject in need thereof comprising administering to the subject an antigen-specific T-cell identified according to the method of claim 15.

17. An immune cell comprising a heterologous TCR, wherein the heterologous TCR is identified according to the method of claim 15.

18. A method of treating a disease or condition in a subject in need thereof, comprising administering to the subject the immune cell of claim 17.

19. The method of claim 12, wherein the flexible linker comprises a GS linker.

* * * * *